United States Patent
Honda et al.

(10) Patent No.: US 10,300,137 B2
(45) Date of Patent: May 28, 2019

(54) COMPOSITIONS AND METHODS FOR INDUCTION OF TH17 CELLS

(71) Applicants: RIKEN, Wako-shi, Saitama (JP); The University of Tokyo, Tokyo (JP); School Corporation, Azabu Veterinary Medicine Educational Institution, Sagamihara-shi, Kanagawa (JP)

(72) Inventors: Kenya Honda, Wako (JP); Koji Atarashi, Wako (JP); Masahira Hattori, Tokyo (JP); Hidetoshi Morita, Sagamihara (JP)

(73) Assignees: RIKEN, Wako-Shi, Saitama (JP); The University of Tokyo, Tokyo (JP); School Corporation, Azabu Veterinary Medicine Educational Institution, Sagamihara-shi, Kanagawa (JP)

( * ) Notice: Subject to any disclaimer, the term of this patent is extended or adjusted under 35 U.S.C. 154(b) by 0 days.

(21) Appl. No.: 15/302,755

(22) PCT Filed: Apr. 10, 2015

(86) PCT No.: PCT/JP2015/061771
§ 371 (c)(1),
(2) Date: Oct. 7, 2016

(87) PCT Pub. No.: WO2015/156419
PCT Pub. Date: Oct. 15, 2015

(65) Prior Publication Data
US 2017/0028061 A1 Feb. 2, 2017

Related U.S. Application Data

(60) Provisional application No. 61/978,182, filed on Apr. 10, 2014.

(51) Int. Cl.
| | |
|---|---|
| *A01N 63/00* | (2006.01) |
| *A61K 39/39* | (2006.01) |
| *A61K 35/74* | (2015.01) |
| *A61K 35/741* | (2015.01) |
| *A61K 35/742* | (2015.01) |
| *A61K 35/745* | (2015.01) |
| *A61K 39/00* | (2006.01) |

(52) U.S. Cl.
CPC .............. *A61K 39/39* (2013.01); *A61K 35/74* (2013.01); *A61K 35/741* (2013.01); *A61K 35/742* (2013.01); *A61K 35/745* (2013.01); *A61K 2039/52* (2013.01); *A61K 2039/542* (2013.01); *A61K 2039/57* (2013.01)

(58) Field of Classification Search
CPC ...................................................... A61K 39/39
See application file for complete search history.

(56) References Cited

U.S. PATENT DOCUMENTS

| | | | |
|---|---|---|---|
| 2003/0092754 A1 | 5/2003 | Nishimuta et al. | |
| 2008/0131556 A1* | 6/2008 | De Simone ............ | A21D 8/042 426/20 |
| 2011/0311617 A1 | 12/2011 | Shirakawa et al. | |
| 2013/0149339 A1 | 6/2013 | Honda et al. | |
| 2013/0266539 A1* | 10/2013 | Borody ................ | A61K 35/741 424/93.3 |
| 2014/0357499 A1* | 12/2014 | Gordon ................ | C12Q 1/6869 506/2 |

FOREIGN PATENT DOCUMENTS

| | | |
|---|---|---|
| EP | 0 640 349 A1 | 3/1995 |
| JP | 59-128333 A | 7/1984 |
| JP | 2011-32170 A | 2/2011 |
| WO | WO 99/019459 A1 | 4/1999 |
| WO | WO 2004/017962 A2 | 3/2004 |
| WO | WO 2011/079282 A1 | 6/2011 |
| WO | WO 2011/135194 A2 | 11/2011 |
| WO | WO 2013/080561 A1 | 6/2013 |

OTHER PUBLICATIONS

Fonty et al (Applied and Environmental Microbiology vol. 73, No. 20, pp. 6391-6403) (Year: 2007).*
PCT/JP2015/061771, dated Jul. 14, 2015, International Search Report and Written Opinion.
Asahara, Preventive Effect of Probiotic Bifidobacteria against Shiga Toxin-Producing *Escherichia Coli* and *Salmonella* Infections. Bioscience Micro. 2010;29:11-21.
Atarashi et al., ATP drives lamina propria T(H)17 cell differentiation. Nature. Oct. 9, 2008;455(7214):808-12. doi: 10.1038/nature07240.
Barnes et al., Regulatory T cells reinforce intestinal homeostasis. Immunity. Sep. 18, 2009;31(3):401-11. doi: 10.1016/j.immuni.2009.08.011.
Bouskra et al., Lymphoid tissue genesis induced by commensals through NOD1 regulates intestinal homeostasis. Nature. Nov. 27, 2008;456(7221):507-10. doi: 10.1038/nature07450.
Cebra, Influences of microbiota on intestinal immune system development. Am J Clin Nutr. May 1999;69(5):1046S-1051S.
Curotto De Lafaille et al., Natural and adaptive Foxp3+ regulatory T cells: more of the same or a division of labor? Immunity. May 2009;30(5):626-35. doi: 10.1016/j.immuni.2009.05.002.

(Continued)

*Primary Examiner* — Albert M Navarro
(74) *Attorney, Agent, or Firm* — Wolf, Greenfield & Sacks, P.C.

(57) ABSTRACT

Strains of human-derived bacteria have been obtained from complex fecal samples and shown to induce accumulation of Th17 cells in the intestine and promote immune functions. Pharmaceutical compositions containing these bacteria can be used as anti-infectives and as adjuvants in mucosal vaccines.

14 Claims, 5 Drawing Sheets
Specification includes a Sequence Listing.

(56) References Cited

OTHER PUBLICATIONS

Eun et al., Induction of bacterial antigen-specific colitis by a simplified human microbiota consortium in gnotobiotic interleukin-$10^{-/-}$ mice. Infect Immun. Jun. 2014;82(6):2239-46. doi: 10.1128/IAI.01513-13.

Gaboriau-Routhiau et al., The key role of segmented filamentous bacteria in the coordinated maturation of gut helper T cell responses. Immunity. Oct. 16, 2009;31(4):677-89. doi: 10.1016/j.immuni.2009.08.020.

Garrett et al., Communicable ulcerative colitis induced by T-bet deficiency in the innate immune system. Cell. Oct. 5, 2007;131(1):33-45.

Ivanov et al., Induction of intestinal Th17 cells by segmented filamentous bacteria. Cell. Oct. 30, 2009;139(3):485-98. doi: 10.1016/j.cell.2009.09.033.

Ivanov et al., The orphan nuclear receptor RORgammat directs the differentiation program of proinflammatory IL-$17^+$ T helper cells. Cell. Sep. 22, 2006;126(6):1121-33.

Korn et al., IL-17 and Th17 Cells. Annu Rev Immunol. 2009;27:485-517. doi: 10.1146/annurev.immunol.021908.132710.

Lycke, Recent progress in mucosal vaccine development: potential and limitations. Nat Rev Immunol. Jul. 25, 2012;12(8):592-605. doi: 10.1038/nri3251.

MacPherson et al., Interactions between commensal intestinal bacteria and the immune system. Nat Rev Immunol. Jun. 2004;4(6):478-85.

Miossec et al., Interleukin-17 and type 17 helper T cells. N Engl J Med. Aug. 27, 2009;361(9):888-98. doi: 10.1056/NEJMra0707449.

Qin et al., A human gut microbial gene catalogue established by metagenomic sequencing. Nature. Mar. 4, 2010;464(7285):59-65. doi: 10.1038/nature08821.

Round et al., The gut microbiota shapes intestinal immune responses during health and disease. Nat Rev Immunol. May 2009;9(5):313-23. doi:10.1038/nri2515. Review. Erratum in: Nat Rev Immunol. Aug. 2009;9(8):600.

Salzman et al., Enteric defensins are essential regulators of intestinal microbial ecology. Nat Immunol. Jan. 2010;11(1):76-83. doi:10.1038/ni.1825.

Sanos et al., RORgammat and commensal microflora are required for the differentiation of mucosal interleukin 22-producing NKp$46^+$ cells. Nat Immunol. Jan. 2009;10(1):83-91. doi: 10.1038/ni.1684.

Yokote et al., NKT cell-dependent amelioration of a mouse model of multiple sclerosis by altering gut flora. Am J Pathol. Dec. 2008;173(6):1714-23. doi: 10.2353/ajpath.2008.080622.

Atarashi et al., Regulation of Th17 cell differentiation by intestinal commensal bacteria. Benef Microbes. Nov. 2010;1(4):327-34. doi: 10.3920/BM2010.0026.

Atarashi et al., Th17 cell induction by adhesion of microbes to intestinal epithelial cells. Cell. Oct. 8, 2015;163(2):367-80. doi: 10.1016/j.cell.2015.08.058. Epub Sep. 24, 2015.

Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom.2008.09.009.

Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.

EP 15776630.4, dated Nov. 20, 2017, Partial Supplementary European Search Report.

EP 15776630.4, dated Feb. 26, 2018, Extended European Search Report.

\* cited by examiner

US 10,300,137 B2

COMPOSITIONS AND METHODS FOR INDUCTION OF TH17 CELLS

RELATED APPLICATIONS

This application is a national stage filing under 35 U.S.C. § 371 of international application number PCT/JP2015/061771, filed Apr. 10, 2015, which claims the benefit under 35 U.S.C. § 119(e) of U.S. provisional application Ser. No. 61/978,182, filed Apr. 10, 2014, each of which is incorporated by reference herein in its entirety.

TECHNICAL FIELD

The subject matter described herein relates to a composition of human-derived bacteria that induces proliferation of T helper 17 (Th17) cells and which comprises, as an active component, human-derived bacteria, preferably (a) one or more bacteria isolated and cultured from the ampicillin-resistant bacterial fraction of a fecal sample or, (b) a culture supernatant of one or more bacteria of (a). It also relates to a method for inducing proliferation of Th17 cells. The composition, which comprises any of (a)-(b) above, is referred to as a bacterial composition. Moreover, the subject matter relates to a method for treating or preventing at least one disease or condition that is responsive to induction of Th17 cells, such as infectious diseases, by oral administration of the bacterial composition alone or in combination with an antigen to an individual in need thereof.

BACKGROUND

Hundreds of species of commensal microorganisms are harbored in the gastrointestinal tracts of mammals, where they interact with the host immune system. Research using germ-free (GF) animals has shown that the commensal microorganisms influence the development of the mucosal immune system, such as histogenesis of Peyer's patches (PPs) and isolated lymphoid follicles (ILFs), secretion of antimicrobial peptides from the epithelium, and accumulation of unique lymphocytes in mucosal tissues, including immunoglobulin A-producing plasma cells, intraepithelial lymphocytes, IL-17-producing CD4-positive T cells (Th 17), and IL-22-producing NK-like cells (Non-Patent Literature (NPL) 1 to 7). Consequently, the presence of intestinal bacteria enhances protective functions of the mucous membranes, enabling the host to mount robust immune responses against pathogenic microbes invading the body. On the other hand, the mucosal immune system maintains unresponsiveness to dietary antigens and harmless microbes (NPL Document 3). Abnormality in the regulation of cross-talk between commensal bacteria and the immune system (intestinal dysbiosis) may lead to overly robust or insufficiently robust immune responses to environmental antigens and to commensal and pathogenic microbes, resulting in disease (NPL 8 to 10). Better approaches to enabling the body to mount an effective immune response to invading pathogenic microbes are needed.

PRIOR ART DOCUMENTS

Non Patent Literature

[NPL 1] J. J. Cebra, "Am J Clin Nutr", May, 1999, 69, 1046S
[NPL 2] A. J. Macpherson, N. L. Harris, "Nat Rev Immunol", June 2004, 4, 478
[NPL 3] J. L. Round, S. K. Mazmanian, "Nat Rev Immunol", May 2009, 9, 313
[NPL 4] D. Bouskra et al., "Nature", Nov. 27, 2008, 456, 507
[NPL 5] K. Atarashi et al., "Nature", Oct. 9, 2008, 455, 808
[NPL 6] I. I. Ivanov et al., "Cell Host Microbe", Oct. 16, 2008, 4, 337
[NPL 7] S. L. Sanos et al., "Nat Immunol", January 2009, 10, 83
[NPL 8] M. A. Curotto de Lafaille, J. J. Lafaille, "Immunity", May 2009, 30, 626
[NPL 9] M. J. Barnes, F. Powrie, "Immunity", Sep. 18, 2009, 31, 401
[NPL 10] W. S. Garrett et al., "Cell", Oct. 5, 2007, 131, 33
[NPL 11] I. I. Ivanov, et al., "Cell", Oct. 30, 2009, 139, 485
[NPL 12] V. Gaboriau-Routhiau et al., "Immunity", Oct. 16, 2009, 31, 677
[NPL 13] N. H. Salzman et al., "Nat Immunol", January 2010, 11, 76.
[NPL 14] J. Quin et al., "Nature", Mar. 4, 2010, 464, 59
[NPL 15] T. Korn et al., "Annu Rev Immunol", April 2009, 27, 485
[NPL 16] P. Miossec et al., "N Engl N Med", Aug. 27, 2009, 361, 888
[NPL 17] I. I. Ivanov et al., "Cell", Sep. 22, 2006, 126, 1121
[NPL 18] Lycke N, "Nature Reviews Immunology", August 2012, 12, 605

SUMMARY OF INVENTION

The present compositions and methods have been made in view of the above-described problems in the art. As described herein, although most bacterial species among the more than a thousand species present in the human microbiota do not have the ability to stimulate Th17 cells, the inventors have obtained, from humans, a few bacterial species that have the ability to cause a robust induction of Th17 cells, by modifying fecal samples derived from humans with various antibiotic treatments, applying methods to isolate pure strains in vitro, and developing culturing methods to manufacture bacterial compositions containing the strains that are suitable for use as pharmaceuticals and as food ingredients. Moreover, the inventors have shown that inoculating animals with the in vitro cultured species also leads to a robust accumulation of Th17 cells.

Described herein are methods of obtaining and culturing intestinal commensal bacteria, isolated from humans, which induce, preferably strongly induce, the proliferation, accumulation, or proliferation and accumulation of Th17 cells. Described are compositions, also referred to as bacterial compositions, that comprise, as an active component, (a) one or more of (at least one, a) certain species of bacteria provided herein (Table 1) or bacteria that contain DNA comprising a nucleotide sequence having at least 97% homology (e.g., 97% homology, 98% homology, 99% homology or 100% homology) with sequences provided herein; (b) a culture supernatant of one or more (at least one, a) such bacteria; or (c) a combination of (a) and (b) and induce the proliferation and/or accumulation of T helper 17 cells (Th17 cells).

More Specifically:

One embodiment is a composition (referred to as a bacterial composition) that induces proliferation, accumulation or both proliferation and accumulation of Th17 cells, the composition comprising, as an active component, (a) at least one (a, one or more) organism selected from the group consisting of: *Clostridium symbiosum, Clostridium hathewayi, Clostridium citroniae, Clostridium bolteae,*

*Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*; (b) a culture supernatant of at least one (a, one or more) bacteria of (a); or (c) a combination of at least one (a, one or more) bacteria of (a) and a culture surpernatant of at least one (a, one or more) bacteria of (a).

One embodiment is a composition that induces proliferation and/or accumulation of Th17 cells, the composition comprising, as an active component, (a) the ampicillin-resistant bacterial fraction of a fecal sample; (b) a culture supernatant of one or more bacteria of (a); or a combination of (a) and (b).

In some embodiments, the active component is one or more of *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*; and a culture supernatant of one or more bacteria described/listed herein. In some embodiments, the active component is a culture supernatant of one or more of the bacteria described/listed herein. In some embodiments, the one or more bacteria or one or more culture supernatant derived from the bacteria is three or more. In some embodiments, the one or more bacteria or one or more culture supernatant derived from the bacteria is five or more. In some embodiments, the one or more bacteria or one or more culture supernatant derived from the bacteria is 10 or more. In some embodiments, the one or more bacteria or one or more culture supernatant derived from the bacteria is 15 or more. In some embodiments, the one or more bacteria or one or more culture supernatant derived from the bacteria is 20.

A bacterial composition as described herein comprises at least one of the following: one bacteria as described herein; at least one culture supernatant obtained from culture in which one (or more) of the bacteria was present (grown or maintained) or a fraction of such a supernatant. It can comprise a combination of any of the foregoing. The term composition/bacterial composition refers to all such combinations.

The bacteria in the composition that induces proliferation and/or accumulation of Th17 cells can be, for example, *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve* or any bacteria (such as human-derived bacteria) that contain DNA comprising at least 97% homology (e.g., 97%, 98%, 99% or 100% homology) with sequences provided herein, such as, but not limited to, the nucleotide sequences designated with SEQ ID Nos. 1-20, which are listed at the pages following the last Example and in the Sequence Listing. In specific embodiments, the bacteria contain DNA comprising a nucleotide sequence that has at least 97%, at least 98% or at least 99% homology with one or more DNA sequence designated with SEQ ID Nos. 1-20. Alternatively, the bacteria contain DNA comprising a nucleotide sequence that has at least 97% (97%, 98%, 99%, 100%) homology with DNA of one or more of the following: *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacteriumdesmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*.

In one embodiment, the composition induces Th17 cells that are transcription factor RORgt-positive T cells or IL-17-producing Th17 cells. In another embodiment, the composition promotes a protective immune response at a mucosal surface.

One embodiment is a pharmaceutical composition that induces proliferation, accumulation or both proliferation and/or accumulation of Th17 cells and promotes immune function. The pharmaceutical composition comprises a bacterial composition described herein and a pharmaceutically acceptable component, such as a carrier, a solvent or a diluent. In specific embodiments, such a pharmaceutical composition comprises (a) (1) at least one (a, one or more) species of bacteria listed in Table 1 or as described herein, (2) a culture supernatant of at least one (a, one or more) such bacteria, or (3) a combination of at least one (a, one or more) species of bacteria listed in Table 1 or as described herein and at least one (a, one or more) culture supernatant of at least one (a, one or more) such bacteria and (b) a pharmaceutically acceptable component, such as carrier, a solvent or a diluent. In specific embodiments, (a) above is at least one organism or substance selected from the group consisting of: *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*, and a culture supernatant of one or more of the bacteria. In some embodiments, (a)(2) above is a culture supernatant of at least one (a, one or more) of the bacteria. In some embodiments, the at least one organism or substances is two or more or three or more. In some embodiments, the at least one organism or substances is four or more or five or more. In some embodiments, the at least one organism or substances is 10 or more. In some embodiments, the at least one organism or substances is 15 or more. In some embodiments, the at least one organism or substances is 20. In further embodiments, (a)(1) above is bacteria (such as human-derived bacteria) that contain DNA comprising at least 97% homology (e.g., 97%, 98%, 99% or 100% homology) with sequences provided herein, such as, but not limited to, the nucleotide sequences designated with SEQ ID Nos. 1-20 herein and listed, for example, at the pages following the last Example and in the Sequence Listing. In specific embodiments of the pharmaceutical composition, the bacteria contain DNA comprising a nucleotide sequence that has at least 97%, at least 98%, at least 99% or at least 100% homology with one or more DNA sequence designated with SEQ ID Nos. 1-20.

The pharmaceutical composition induces the proliferation and/or accumulation of T helper cells (Th17 cells) and promotes immune function.

Also provided is a method of inducing proliferation, accumulation or both proliferation and accumulation of Th17 cells in an individual (e.g., an individual in need thereof, such as an individual in need of induction of proliferation and/or accumulation of Th17 cells). The method comprises administering to the individual a bacterial composition described herein or a pharmaceutical composition comprising a bacterial composition described herein. In the method at least one organism or substance selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve*; a culture supernatant of one or more of the bacteria or one or more component of the culture supernatant; or a combination of any number of the foregoing is administered to an individual (also referred to as an individual in need thereof) who can be a healthy individual or an individual in need of prevention, reduction or treatment of a condition or disease. For example, the bacterial compositions described may be administered to an individual in need of treatment, reduction in the severity of or prevention of a disease or condition such as an infectious disease.

Optionally, administration of the bacterial composition may be in combination with, or preceeded by, a course of one or more antibiotics.

Optionally, administration of the bacterial composition may be in combination with administration of at least one prebiotic substance that preferentially favors the growth of the species in the bacterial composition over the growth of other human commensal bacterial species. In one embodiment, the prebiotic substance(s) is, for example, a nondigestible oligosaccharide.

In a further embodiment, the bacterial composition can be used as an adjuvant to improve the efficacy of a mucosal vaccine formulation. For example, the bacterial composition can be used as an adjuvant to a vaccine for the prophylaxis or treatment of an infectious disease or cancer. In some embodiments, a method for prophylaxis or treatment is provided, the method comprising administering the bacterial composition or pharmaceutical composition as a vaccine adjuvant. The bacterial composition or pharmaceutical composition may be administered as an adjuvant with existing mucosal vaccines.

In a further embodiment, the bacterial composition comprises, as an active component, at least one organism selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve* wherein the organism comprises an expression vector that contains a heterologous gene, also referred to as a vector expressing a heterologous protein or peptide, such as an antigen.

Assessment of the extent of induction of proliferation or accumulation of Th17 cells that results from administration of a composition described herein can be carried out by a variety of approaches such as by measurement of the number of Th17 cells prior and after administration, or by measurement of Th17 activity, such as expression of at least one of RORgt, IL-17A, IL-17F, IL-22, IL-23, IL-23R, CD161, and CCR6 after the administering relative to the expression of at least one of RORgt, IL-17A, IL-17F, IL-22, IL-23, IL-23R, CD161, and CCR6 determined prior to the administering colonization of an individual with the bacterial composition. The results of such assessments are used as an index of the induction of proliferation or accumulation of Th17 cells in the individual.

In one embodiment, administration of a composition described herein causes induction of the Th17 cells that are transcription factor RORgt-positive Th17 cells or IL-17-producing Th17 cells.

The composition described herein can be administered by a variety of routes and in one embodiment, is administered orally to an individual in need thereof, such as a patient in need thereof. The composition may be administered in a number of oral forms, such as in a dry powder, a lyophilisate, or dissolved in a liquid formulation, in enteric capsules, in sachets, or in a food matrix, such as yogurt, or a drink.

Also provided is a method of monitoring a subject's response to treatment with the bacterial compositions of the invention, comprising: (a) obtaining a (at least one; one or more) sample, such as a fecal sample or a colonic biopsy sample, from a patient before treatment with a bacterial composition described herein; (b) obtaining, a (at least one; one or more) corresponding sample from the patient after treatment with a bacterial composition described herein; and (c) determining and comparing the percentage or absolute counts of at least one bacterial species selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve* in the sample obtained in (a) with the percentage or absolute counts of the same at least one bacterial species in the sample obtained in (b), wherein a higher value in the sample obtained in (b) (after treatment with the bacterial composition) than in the sample obtained in (a) (before treatment) indicates that the subject has responded favorably to treatment (e.g. is a positive indicator of enhanced immune response in the subject). In some embodiments, the method further comprises (d) further administering the bacterial composition to the patient or ceasing administration of the bacterial composition to the patient based on the comparison in (c).

Also provided is a method of obtaining Th17-inducing bacterial compositions, comprising (a) treating a subject with the antibiotic ampicillin, or an antibiotic with a similar spectrum, for example an aminopenicillin family member such as amoxicillin, penicillin, or benzylpenicillin; (b)

obtaining (at least one) sample, such as a fecal sample or an intestinal biopsy sample from the subject (the "ampicillin-resistant bacterial fraction of a fecal sample"); (c) culturing the sample from (b) and isolating pure bacterial strains from the resulting colonies. In a preferred embodiment the subject in (a) is an ex-germ-free animal that has been colonized with a fecal sample obtained from a human donor. In a preferred embodiment, the isolation of pure bacterial strains of (c) is performed by serial dilutions of cecal content samples cultured by plating under a strictly anaerobic condition. In another embodiment, the method comprises (a) obtaining a (at least one; one or more) sample, such as a fecal sample or an intestinal biopsy from a subject; (b) treating the sample of (a) with ampicillin; (c) culturing the ampicillin-treated sample of (b) and isolating pure bacterial strains.

Also provided is a method of inhibiting Th17-inducing bacterial compositions to treat autoimmune and inflammatory diseases in an individual, the method comprising administering an antibiotic, such as vancomycin and/or metronidazole to the individual.

EFFECTS OF INVENTION

The compositions described herein are excellent at inducing the proliferation or accumulation of T helper 17 cells (Th17 cells). Immunity in an individual can be promoted through administration of the subject composition, such as through ingestion of the bacterial composition in a food or beverage or as a dietary supplement or through administration of a pharmaceutical composition comprising the bacterial composition. The subject composition can be used, for example, to prevent or treat infectious diseases, as well as in combination with mucosal vaccines to prevent diseases caused by microorganisms or the like. In addition, if a food or beverage, such as a health food, comprises the subject composition, healthy individuals can ingest the composition easily and routinely. As a result, it is possible to induce the proliferation and/or accumulation of Th17 cells and thereby improve immune functions.

The compositions described herein provide for a potent, long-lasting, patient-friendly, and benign treatment alternative for infectious diseases. For example, infectious disease is often managed with antibiotics that may lead to antibiotic-resistance and/or opportunistic infection; systemic vaccines require extensive purification due to their injectable nature, which risks spreading blood-borne infections and are not practical for mass vaccination; existing mucosal vaccines fail to achieve sufficiently strong immune responses and are often not as stable as a live attenuated formulation.

The compositions described herein, used in combination with a mucosal vaccine antigen, can also have an effect of increasing the immune response against the antigen, or extending the duration of the immune response against the antigen, or enabling a reduction of the dose and frequency of administration of the antigen (for example, reducing the number of booster injections of antigen-containing composition) required to achieve protection, or increasing the proportion of patients achieving seroconversion, or eliciting optimal immune responses in patients in which other vaccination strategies are not effective (for example, young or aging populations).

Figure 1A:
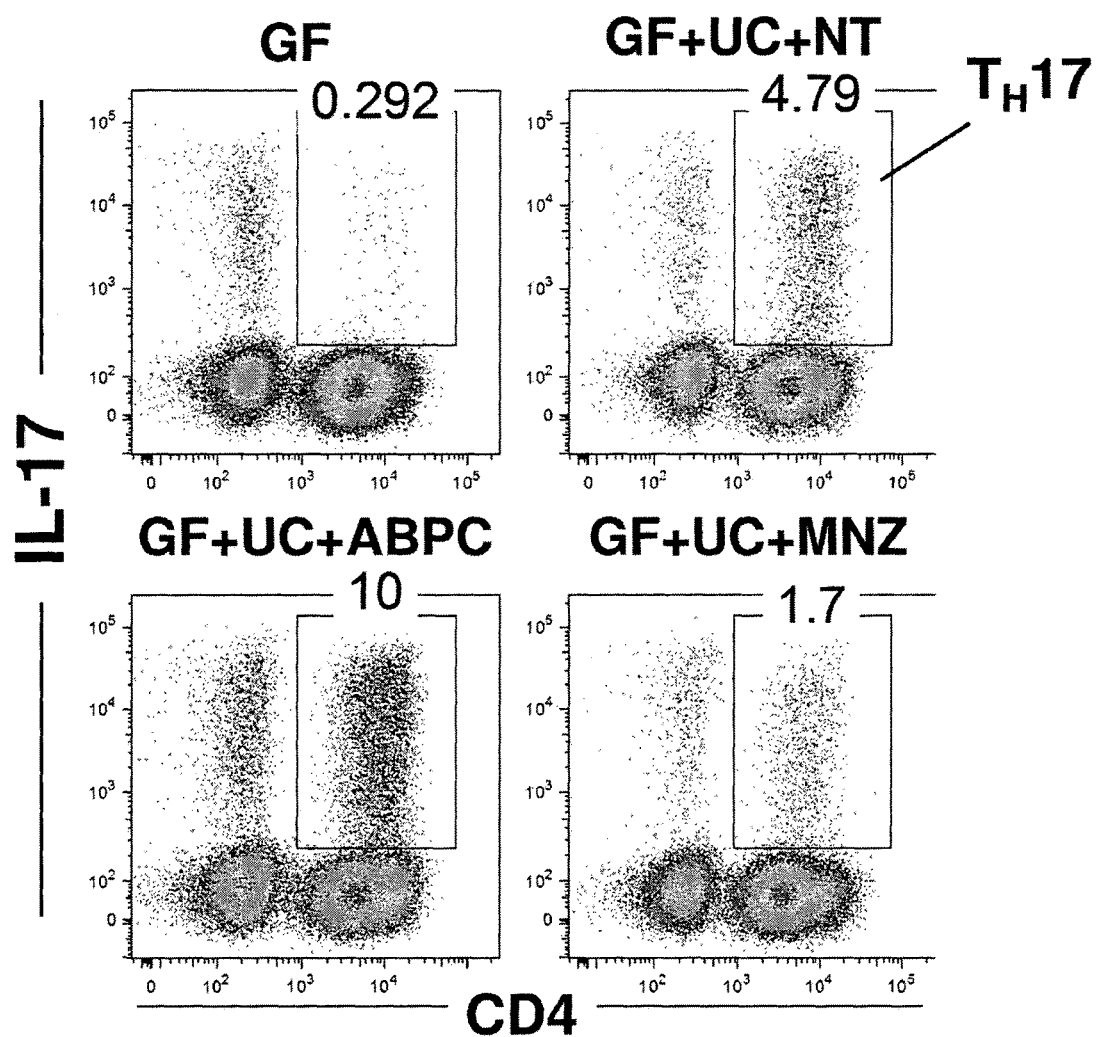
FIG. 1A is a FACS dot-plot diagram showing analysis of results of expression of IL-17 in CD4+ lymphocytes isolated from colonic lamina propia of germ-free (GF) mice (upper left panel) or GF mice colonized with stool from ulcerative colitis patients and untreated (GF+UC+NT, upper right panel), or GF mice colonized with stool from ulcerative colitis patients and treated with ampicillin in the drinking water (GF+UC+ABPC, lower left panel), or GF mice colonized with stool from ulcerative colitis patients and treated with metronidazole in the drinking water (GF+UC+MNZ, lower right panel).

Table 1 shows, for each of 20 bacterial strains isolated from the cecal contents of mice colonized with human patient stool and treated with ampicillin, the closest relative in known species from the RDP (Ribosomal Database Project) database, and the maximum similarity with the closest relative.

DESCRIPTION OF EMBODIMENTS

Recent studies have shown that individual commensal bacteria control differentiation of their specific immune cells in the mucosal immune system. For example, segmented filamentous bacteria, which are intestinal commensal bacteria in mice, induce mucosal Th17 cell response and enhance resistance against infection of gastrointestinal tracts of the host with a pathogen (NPL 11 to 13). Although specific species of murine bacterial commensals, such as segmented filamentous bacteria, that can strongly stimulate Th17 cells have been identified (NPL 11 to 13), it is still unknown whether species of human commensal bacteria exert an equivalent influence on the human immune system. Furthermore, the human intestinal tract harbors more than a thousand bacterial species, many of which have not yet been cultured (NPL 14). It is not feasible to guess a priori which ones, if any, might have an effect on Th17 cells.

In order to develop drugs, vaccines, dietary supplements, or foods with beneficial immune functions for human use, it is desirable to identify commensal microorganisms that naturally colonize humans and have immune-modulating properties. Furthermore, since many of the commensals in the human microbiome have yet to be cultured, it is necessary to develop methods to cultivate them so that they can be produced by industrial fermentation processes and subsequently incorporated in pharmaceutical or food formulations.

T helper 17 (Th17) cells are a subset of CD4+ T helper cells that provide anti-microbial immunity at mucosal surfaces, which can be critical for defense against microorganisms such as bacteria and fungi. Th17 cells depend on TGF-beta and IL-6 for differentiation and are defined by the lineage-specific transcription factor RORgt (NPL 11, 15, and 16). RORgt-expressing Th17 cells are present in large numbers in the gastrointestinal tract (NPL 6, 17). Memory CD4+ and CD8+ T cells can also be generated as a result of mucosal vaccination. In particular, memory Th17 cells with protective functions can be induced by mucosal vaccination (NPL 18).

Many infectious diseases are restricted to the mucosal membranes, or the infectious agent needs to cross the mucosal membrane during the early stages of infection. Therefore, it is desirable to obtain not only a systemic, but also a localized mucosal immune response as a result of vaccination, which can enhance protection against the infection. Vaccines administered by the mucosal route could thus be particularly effective in protecting against mucosal pathogens. However, existing mucosal vaccines are limited in their ability to promote robust immune responses at the mucosa, because exposure to antigens is not sufficiently prolonged, because the amount of antigens provided is insufficient to trigger a robust response, or because the antigens are not sufficiently immunogenic or stable. Partly because of these reasons, most vaccines used currently are still administered via the parenteral route. When host immune responses to an immunogenic antigen are too weak, it may be necessary to enhance them by co-administering an adjuvant.

Accordingly, human-derived commensal bacterial compositions with the ability to strongly induce Th17 cells are needed, as are methods to manufacture such compositions. Such compositions can be used to enable the host to mount robust immune responses against pathogenic microbes invading the body, and thus be applied as anti-infectives or as adjuvants of mucosal vaccines.

The term "T helper 17 cells (Th17 cells)" refers to T cells that promote an immune response and play a role in immune defense. Th17 cells are typically transcription factor RORgt-positive CD4-positive T cells. The Th17 cells of the present invention also include transcription factor RORgt-negative T cells that are IL-17-producing CD4-positive T cells.

The term "induces proliferation or accumulation of Th17 cells" refers to an effect of inducing the differentiation of immature T cells into Th17 cells, which differentiation leads to the proliferation and/or the accumulation of Th17 cells. Further, the meaning of "induces proliferation or accumulation of Th17 cells" includes in-vivo effects, in vitro effects, and ex vivo effects. All of the following effects are included: an effect of inducing in vivo proliferation or accumulation of Th17 cells through administration or ingestion of the aforementioned bacteria, or a culture supernatant of the bacteria or supernatant component(s); an effect of inducing proliferation or accumulation of cultured Th17 cells by causing the aforementioned bacteria or a culture supernatant of the bacteria or supernatant component(s) to act on the cultured Th17 cells; and an effect of inducing proliferation or accumulation of Th17 cells which are collected from a living organism and which are intended to be subsequently introduced into a living organism, such as the organism from which they were obtained or another organism, by causing the aforementioned bacteria, a culture supernatant of the bacteria or supernatant component(s), or a physiologically active substance derived from the bacteria to act on the Th17 cells. The effect of inducing proliferation or accumulation of Th17 cells can be evaluated, for example, as follows. Specifically, the aforementioned bacteria, a culture supernatant of the bacteria or supernatant component(s), or a physiologically active substance derived from the bacteria is orally administered to an experimental animal, such as a germ-free mouse, then CD4-positive cells in the gastrointestinal tract are isolated, and the ratio of Th17 cells contained in the CD4-positive cells is measured by flow cytometry.

The Th17 cells whose proliferation or accumulation is induced by the composition of the present invention are preferably transcription factor RORgt-positive Th17 cells or IL-17-producing Th17 cells.

In the present invention, "human-derived bacteria" means bacterial species that have been isolated from a fecal sample or from a gastrointestinal biopsy obtained from a human individual or whose ancestors were isolated from a fecal sample or from a gastrointestinal biopsy obtained from a human (e.g., are progeny of bacteria obtained from a fecal sample or a gastrointestinal biopsy). For example, the bacterial species may have been previously isolated from a fecal sample or from a gastrointestinal biopsy obtained from a human and cultured for a sufficient time to generate progeny. The progeny can then be further cultured or frozen.

In the present invention, the term "immune response" signifies any reaction produced by an antigen, such as a protein antigen, in a host having a functioning immune system. Immune responses may be humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines.

<Composition Having Effect of Inducing Proliferation or Accumulation of Th17 Cells>

Described herein is a composition that induces proliferation, accumulation of Th17 cells or both proliferation and accumulation of Th17 cells. The composition comprises, as an active ingredient, one or more of the following: an (at least one, one or more) organism (bacteria) selected from the group consisting of: *Clostridium symbiosum* (SEQ ID No 16), *Clostridium hathewayi* (SEQ ID No 12), *Clostridium citroniae* (SEQ ID No 20), *Clostridium bolteae* (SEQ ID No 19), *Ruminococcus* sp. M-1 (SEQ ID No 14), *Ruminococcus gnavus* (SEQ ID No 9), *Blautia* sp. canine oral taxon 143 (SEQ ID No 4), *Anaerostipes caccae* (SEQ ID No 18), *Clostridium lactatifermentans* (SEQ ID No 3), *Coprobacillus cateniformis* (SEQ ID No 15), *Clostridium ramosum* (SEQ ID No 1), cf. *Clostridium* sp. MLG055 (SEQ ID No 5), *Clostridium innocuum* (SEQ ID No 6), *Eubacterium desmolans* (SEQ ID No 11), *Clostridium orbiscindens* (SEQ ID No 7), *Ruminococcus* sp. 16442 (SEQ ID No 8), *Anaerotruncus colihominis* (SEQ ID No 10), *Bacteroides dorei* (SEQ ID No 17), *Bifidobacterium pseudolongum* subsp. *Pseudolongum* (SEQ ID No 2), and *Bifidobacterium breve* (SEQ ID No 13), a culture supernatant of one or more of the bacteria, a component of culture medium in which a (at least one, one or more) bacterium described herein has grown; and a (at least one; one or more) bacterium containing DNA comprising a nucleotide sequence having at least 97% homology to the nucleotide sequence of DNA of any of the bacterial species described herein, such as those listed above. Bacteria described herein were isolated from human fecal samples using the methods outlined in Examples 1 to 3.

The bacterial composition or pharmaceutical composition may include one strain alone (only one strain) of any of the bacterial species listed or described herein; two or more strains of the bacteria can be used together. For example, one, two, three, four, five, six, seven, eight, nine, ten, eleven, twelve, thirteen, fourteen, fifteen, sixteen, seventeen, eighteen, nineteen, or twenty of the strains listed in Table 1, in any combination, can be used together to affect Th17 cells.

If more than one strain of bacteria is used, the number and ratio of strains used can vary widely. The number and ratio to be used can be determined based on a variety of factors (e.g., the desired effect, such as induction or inhibition of proliferation or accumulation of Th17 cells; the disease or condition to be treated, prevented or reduced in severity; the age or gender of the recipient; the typical amounts of the strains in healthy humans). The strains can be present in a single composition, in which case they can be consumed or ingested together (in a single composition), or can be present in more than one composition (e.g., each can be in a separate composition), in which case they can be consumed individually or the compositions can be combined and the resulting combination (combined compositions) consumed or ingested. Any number or combination of the strains that proves effective (e.g., any number from one to 20, such as 1 to 20, 1 to 15, 1 to 10, 1 to 5, 1 to 3, 1 to 2, and any number therebetween can be administered. In certain embodiments of the present invention, a combination of some or all of the 20 (e.g., the 20 strains in Table 1) strains described in the present disclosure is used. For example, at least one, two or more, three, three or more, four, four or more, five, five or more, six, six or more or any other number of the 20 described strains, including 20 strains, can be used. They can be used in combination with one another and in combination with strains not described in the cited reference.

When the aforementioned bacterial compositions are cultured in a medium, substances contained in the bacteria, secretion products and metabolites produced by the bacteria are released from the bacteria. The meaning of active ingredient "culture supernatant of the bacteria" in the composition includes such substances, secretion products, and metabolites. The culture supernatant is not particularly limited, as long as the culture supernatant has the effect of inducing proliferation or accumulation of Th17 cells. Examples of the culture supernatant include a protein fraction of the culture supernatant, a polysaccharide fraction of the culture supernatant, a lipid fraction of the culture supernatant, and a low-molecular weight metabolite fraction of the culture supernatant.

The bacterial strains in the bacterial compositions may be administered in live form, or they may be administered in attenuated, inactivated, or killed form (for example, heat-killed).

The bacterial composition may be administered in the form of a pharmaceutical composition, a dietary supplement, or a food or beverage (which may also be an animal feed), or may be used as a reagent for an animal model experiment. The pharmaceutical composition, the dietary supplement, the food or beverage, and the reagent induce proliferation or accumulation of Th17 cells. Examples presented herein revealed that the bacterial composition induced Th17 cells when administered to animals. The composition of the present invention can be used suitably as a composition having an effect of promoting an immune response.

The bacterial composition of the present invention can be used, for example, as a pharmaceutical composition for preventing or treating (reducing, partially or completely the adverse effects of) an infectious disease, such as a bacterial infection, a viral infection, a parasitic infection, and a fungal infection. Oral administration of the newly identified compositions and their subsequent colonization of the gastrointestinal tract induces Th17 cells at the mucosal surface. These Th17 cells mediate protective immune responses at mucosal surfaces against a number of infectious agents, including bacteria, viruses, fungi, and parasites.

More specific examples of target infectious diseases for which the composition is useful for treatment (reducing adverse effects or prevention) include bacterial infections including but not limited to *P. aeruginosa, E. coli, C. tetani, N gonorrhoeae, C. botulinum, Klebsiella* sp., *Serratia* sp., *Pseudomanas* sp., *P. cepacia, Acinetobacter* sp., *S. epidermis, E. faecalis, S. pneumonias, S. aureus; S. mutans, Haemophilus* sp., *Neisseria* Sp., *N. meningitides, Bacteroides* sp., *Citrobacter* sp., *Branhamella* sp., *Salmonelia* sp., *Shigella* sp., *S. pyogenes, Proteus* sp., *Clostridium* sp., *Erysipelothrix* sp., *Listeria* sp., *Pasteurella multocida, Streptobacillus* sp., *Spirillum* sp., *Fusospirocheta* sp., *Treponema pallidum, Borrelia* sp., *Actinomycetes, Mycoplasma* sp., *Chlamydia* sp., *Rickettsia* sp., *Spirochaeta, Borellia burgdorferi, Legionella* sp., *Mycobacteria* sp, *Ureaplasma* sp, *Streptomyces* sp., *Trichomoras* sp., *P. mirabilis; vibrio cholera*, enterotoxigenic *Escherichia coli, Clostridium difficile, Salmonella typhi, C. diphtheria, Mycobacterium leprae, Mycobacterium lepromatosi*; Viral infections including but not limited to picornaviridae, caliciviridae, togaviridae, flaviviridae, coronaviridae, rhabdoviridae, filoviridae, paramyxoviridae, orthomyxoviridae, bunyaviridae, arenaviridae, reoviridae, retroviridae, hepadnaviridae, parvoviridae, papovaviridae, adenoviridae, herpesviridae, poxviridae, rotavirus, parainfluenza virus, influenza virus A and B, syphilis, HIV, rabies virus, Epstein-Barr virus, and herpes simplex virus; Parasitic infections including but not limited to *Plasmodium falciparum, P. vivax, P. ovale, P. malaria, Toxoplasma gondii, Leishmania mexicana, L. tropica, L. major, L. aethiopica, L. donovani, Trypanosoma cruzi, T. brucei, Schistosoma mansoni, haematobium, S. japonium, Trichinella spiralis, Wuchereria bancrofti, Brugia malayli, Entamoeba histolytica, Enterobius vermiculoarus, Taenia solium, T saginata, Trichomonas vaginatis, T hominis, T. tenax; Giardia lamblia, Cryptosporidium parvum, Pneumocytis carinii, Babesia bovis, B. divergens, B. microti, Isospore belli, L hominis, Dientamoeba fragiles, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latum, Echinococcus granulosus, E. multilocularis, Paragonimus westermani, P. caliensis, Chlonorchis sinensis, Opisthorchis felineas, G. Viverini, Fasciola hepatica Sarcoptes scabiei, Pediculus humanus, Phthirius pubis,* and *Dermatobia hominis*; and Fungal infections including but not limited to *Cryptococcus neoformans, Blastomyces dermatitidis, Aiellomyces dermatitidis, Histoplasfria capsulatum, Coccidioides immitis, Candida* species, including *C. albicans, C. tropicalis, C. parapsilosis, C. guilliermondii* and *C. krusei, Aspergillus* species, including *A. fumigatus, A. flavus* and *A. niger, Rhizopusspecies, Rhizomucor* species, *Cunninghammella* species, *Apophysomyces* species, including *A. saksenaea, A. mucor* and *A. absidia, Sporothrix schenckii, Paracoccidioides brasiliensis, Pseudallescheria boydii, Torulopsis glabrata*; and *Dermatophyres* species.

The bacterial composition may be administered as an adjuvant in combination with antigenic material. The antigenic material can include one or more portions of the protein coat, protein core, or functional proteins and peptides of a pathogen, or a full pathogen (live, killed, inactivated, or attenuated), or may comprise one or a plurality of cancer epitopes or cancer antigens. The antigenic material can be co-administered, administered before, or after the bacterial composition. The bacterial composition may also be administered with existing mucosal vaccines such as influenza vaccines, (e.g. FluMist from MedImmune or NASOVAC from Serum Institute of India), rotavirus vaccines (e.g. RotaTeq from Merck or Rotarix from GlaxoSmithKline), typhoid vaccines (e.g. Vivotif from Crucell, Ty21A), cholera vaccines (e.g. Orochol from Crucell, Shanchol from Shantha Biotechnics), traveller's diarrhea vaccines (e.g. Dukoral from Crucell), and with antigens of live attenuated Influenza A virus H1 strain, live attenuated Influenza A virus H3 strain, Influenza B virus, live attenuated H1N1 influenza virus (swine flu), live attenuated rotavirus, mono- and multi-valent poliovirus, live attenuated *Salmonella Typhi*, live recombinant *Vibrio cholerae* lacking cholera toxin subunit A, whole killed *Vibrio cholerae* O1 classical and El Tor biotypes with or without cholera toxin subunit B, cancer antigens, cancer epitopes, and combinations thereof.

The bacterial composition can be engineered to express specific antigens from selected pathogens or cancer antigens using genetic engineering methods well known to those skilled in the art and used, for example, as a pharmaceutical composition for prolonging exposure to said antigens and inducing stronger mucosal immune responses than oral administration of the soluble antigens alone. In one embodiment, an organism from Table 1 can be engineered by incorporation of an expression vector expressing a heterologus antigen. Said heterologous antigens may include, but are not limited to, influenza HA, NA, M2, HIV gp120, *mycobacterium tuberculosis* Ag85B and ESAT6, *Streptococcus pneumonia* PspA, PsaA, and CbpA, respiratory syncytial virus (RSV) F and G protein, human papilloma virus protein, and cancer antigens. Furthermore, the Th-17 inducing strains can also be engineered to have a limited capacity for replication in the host, while delivering a sufficiently high antigen load at the site of immunization, so that long-term colonization by the strains is avoided.

The bacterial composition described herein and other Th17-inducing strains can be inhibited for use in preventing or treating (reducing, partially or completely, the adverse effects of) autoimmune and inflammatory diseases. Th17 cells can also have the deleterious effect of promoting chronic autoimmune and inflammatory responses in the host. Accordingly, methods of inhibiting the Th17-inducing strains via administration of molecules that impair their growth and/or function, or directly kill the Th17-inducing strains, can be used for treating autoimmune and inflammatory diseases mediated by Th17 responses. Antibiotics including, but not limited to, vancomycin and metronidazole, can be used to inhibit the Th17-inducing strains. Target diseases for which inhibition of the Th17-inducing strains is useful for treatment include: inflammatory bowel disease (IBD), ulcerative colitis, Crohn's disease, sprue, autoimmune arthritis, rheumatoid arthritis, Type I diabetes, multiple sclerosis, osteoarthritis, systemic lupus erythematosus, insulin dependent diabetes mellitus, asthma, psoriasis, atopic dermatitis, graft versus host disease, acute or chronic immune disease associated with organ transplantation, sarcoidosis, atherosclerosis, atopic allergy, food allergies such as peanut allergy, tree nut allergy, egg allergy, milk allergy, soy allergy, wheat allergy, seafood allergy, shellfish allergy, or sesame seed allergy, allergic rhinitis (pollen allergies), anaphylaxis, pet allergies, latex allergies, drug allergies, allergic rhinoconjuctivitis, eosinophilic esophagitis, and diarrhea, among others.

Pharmaceutical preparations can be formulated from the bacterial compositions described by drug formulation methods known to those of skill in the art. For example, the composition can be used orally in the form of capsules, tablets, pills, sachets, liquids, powders, granules, fine granules, film-coated preparations, pellets, troches, sublingual preparations, chewables, buccal preparations, pastes, syrups, suspensions, elixirs, and emulsions, or it can be used in a suppository or an enema.

Pharmaceutical preparations for use in mucosal vaccination can be formulated in oral form such as a solution, suspension, or emulsion in an aqueous or oil solvent, or dried as a powder. In addition, depending on the purpose, buffers, isotonizing agents, soothing agents, preservative agents, or anti-oxidants, may be added to the mucosal vaccine formulation.

For formulating these preparations, the bacterial compositions can be used in appropriate combination with carriers that are pharmacologically acceptable or acceptable for ingestion, such as in a food or beverage, including one or more of the following: sterile water, physiological saline, vegetable oil, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, a flavor corrigent, a solubilizer, and other additives.

A pharmaceutical preparation or formulation and particularly a pharmaceutical preparation for oral administration, can comprise an additional component that enables efficient delivery of the bacterial composition of the present invention to the colon, in order to more efficiently induce proliferation or accumulation of Th17 in the colon. A variety of pharmaceutical preparations that enable the delivery of the bacterial composition to the colon can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of decomposition is between about 6.8 and about 7.5. Such a numeric value range is a range in which the pH shifts toward the alkaline side at a distal portion of the stomach, and hence is a suitable range for use in the delivery to the colon.

Another embodiment of a pharmaceutical preparation useful for delivery of the bacterial composition to the colon is one that ensures the delivery to the colon by delaying the release of the contents (e.g., the bacterial composition) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Examples of the composition enabling the delivery to the colon further include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

The bacterial composition can be used as a food or beverage, such as a health food or beverage, a food or beverage for travelers, for infants, pregnant women, athletes, senior citizens or other specified group, a functional food, a food or beverage for specified health use, a dietary supplement, a food or beverage for patients, or an animal feed.

The addition of the bacterial composition to an antibiotic-free animal feed makes it possible to increase the body weight of an animal that ingests the animal feed to a level equal to or higher than that achieved by ingestion of antibiotic-containing animal feeds, and also makes it possible to reduce pathogenic bacteria in the gastrointestinal tract to a level equal to those in animals consuming typical antibiotic-containing animal feeds. The bacterial composition can be used as a component of an animal feed that does not need the addition of antibiotics. Animal feed comprising the bacterial composition can be fed to a wide variety of types of animals and animals of a varying ages and can be fed at regular intervals or for a certain period (for example, at birth, during weaning, or when the animal is relocated or shipped).

The bacterial active components of the bacterial composition can be manufactured using fermentation techniques. In one embodiment, the bacterial active components are manufactured using anaerobic fermentors, which can support the rapid growth of bacterial strains. The anaerobic fermentors may be, for example, stirred tank reactors or disposable wave bioreactors. Culture media such as BL agar, or similar versions of these media devoid of animal components can be used to support the growth of the bacterial species. The bacterial product can be purified and concentrated from the fermentation broth by techniques such as centrifugation and filtration, and can optionally be dried and lyophilized.

The amount of the bacterial composition to be administered or ingested can be determined empirically, taking into consideration such factors as the age, body weight, gender, symptoms, health conditions, of an individual who will receive it, as well as the kind of bacterial composition (a pharmaceutical product, a food or beverage) to be administered or ingested. For example, the amount per administration or ingestion is generally 0.01 mg/kg body weight to 100 mg/kg body weight, and, in specific embodiments, 1 mg/kg body weight to 10 mg/kg body weight. Also described herein is a method for promoting immunity (potentiating the immune response) of a subject, the method being characterized in that the bacterial compostions is administered to or ingested by the subject as described above.

The bacterial composition may be administered to an individual once, or it may be administered more than once. If the composition is administered more than once, it can be administered on a regular basis (for example, once a day, once every two days, once a week, once every two weeks, once a month, once every 6 months, or once a year) or on an as needed or irregular basis. The appropriate frequency of administration (which may depend on host genetics, age, gender, and health or disease status of the subject, among other factors) may be determined empirically. For example, a patient can be administered one dose of the composition, and the levels of the bacterial strains of the composition in fecal samples obtained from the patient can be measured at different times (for example, after 1 day, after 2 days, after 1 week, after 2 weeks, after 1 month). When the levels of the bacteria fall to, for example, one half of their maximum post-dose value, a second dose can be administered, and so on.

A product comprising the bacterial composition (a pharmaceutical product, a food or beverage, or a reagent) or a manual thereof may be accompanied by document or statement explaining that the product can be used to promote immunity (including a statement that the product has an effect of promoting immunity and a statement that the product has an effect of promoting the proliferation or function of Th17 cells). Here, the "provision to the product or the manual thereof with the note" means that the document or statement is provided to a main body, a container, a package, or the like of the product, or the note is provided to a manual, a package insert, a leaflet, or other printed matters, which disclose information on the product.

<Method for Inducing Proliferation or Accumulation of Th17 Cells>

As described above, and as shown in Examples 1 to 3, administration of the bacterial composition to an individual makes it possible to induce proliferation or accumulation of Th17 cells in the individual. This provides a method of inducing proliferation or accumulation of Th17 cells in an individual, the method comprising: administering, to the individual, at least one member selected from the group consisting of: (a) *Clostridium symbiosum*, *Clostridium hathewayi*, *Clostridium citroniae*, *Clostridium bolteae*, *Ruminococcus* sp. M-1, *Ruminococcus gnavus*, *Blautia* sp. canine oral taxon 143, *Anaerostipes caccae*, *Clostridium lactatifermentans*, *Coprobacillus cateniformis*, *Clostridium ramosum*, cf. *Clostridium* sp. MLG055, *Clostridium innocuum*, *Eubacterium desmolans*, *Clostridium orbiscindens*, *Ruminococcus* sp. 16442, *Anaerotruncus colihominis*, *Bacteroides dorei*, *Bifidobacterium pseudolongum* subsp. *Pseudolongum*, and *Bifidobacterium breve*; (b) a culture supernatant of at least one (a, one or more) of the bacteria described/listed herein; or a combination of (a) and (b). The bacterial composition is administered (provided) to the individual in sufficient quantity to produce the desired effect of inducing proliferation, accumulation or both proliferation and accumulation of Th17 cells. It may be administered to an individual in need of treatment or reduction in the severity of an infectious disease. It may also be administered to an individual in need of prevention of an infectious disease, as an adjuvant of a mucosal vaccine formulation.

Note that, the "individual" or "subject" (e.g., a human) may be in a healthy state or a diseased state. The method may further comprise the optional step of administering at least one (a, one or more) antibiotic preceding, or in combination with, the bacterial composition.

Moreover, a prebiotic composition can be used to favor the growth of the species in the bacterial composition over the growth of other human commensal bacterial species. In one embodiment, the prebiotic substance(s) is a nondigestible oligosaccharide. A method of inducing proliferation and/or accumulation of Th17 in an individual can comprise administering, to the individual, at least one prebiotic or at least one antibiotic in combination with the bacterial composition. Also contemplated herein is a composition comprising the bacterial composition and a prebiotic composition or an antibiotic composition.

There is no particular limitation imposed on the combined use of the therapeutic composition with at least one substance selected from the group consisting of the bacterial composition, the "mucosal vaccine formulation", the "mucosal vaccine antigen", the "antibiotic", and the "prebiotic composition". For example, the "one substance" and the therapeutic composition are administered orally or parenterally to an individual simultaneously or sequentially/individually at any appropriate time.

Whether administration of the bacterial composition induces the proliferation and/or accumulation of Th17 cells can be determined by using, as an index, increase or reinforcement of at least one of the following: the number of Th17 cells, the ratio of Th17 cells in the T cell group of the gastrointestinal tract, a function of Th17 cells, or expression of a marker of Th17 cells. A specific approach is measurement counts or percentage of RORgt-expressing Th17 cells in a patient sample, such as a biopsy or a blood sample, promotion (enhancement) of IL-17 expression, or colonization of an individual with the bacterial composition administered as the index of the induction of proliferation or accumulation of Th17 cells. Methods for detecting such expression include northern blotting, RT-PCR, and dot blotting for detection of gene expression at the transcription level; ELISA, radioimmunoassays, immunoblotting, immunoprecipitation, and flow cytometry for detection of gene expression at the translation level. Samples that may be used for measuring such an index include tissues and fluids obtained from an individual, such as blood, obtained in a biopsy, and a fecal sample.

<Method for Monitoring a Subject's Response to the Bacterial Composition>

Also provided is a method of monitoring a subject's (e.g., a human's) response to treatment with the bacterial compositions described herein, comprising: (a) obtaining a (one or more, at least one) sample, such as a fecal sample or a colonic biopsy from a patient before treatment with a bacterial composition described herein; (b) obtaining, a (one or more, at least one) corresponding sample from the patient after treatment with a bacterial composition described herein; and (c) comparing the percentage or absolute counts of at least one bacterial species selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve* in the sample obtained in (a) with the percentage or absolute counts of the same at least one bacterial species in the sample obtained in (b), wherein a higher value in the sample obtained in (b) (after treatment with the bacterial composition) than in the sample obtained in (a) (before treatment) indicates that the subject has responded favorably to treatment (e.g., is a positive indicator of enhanced immune response in the subject). In some embodiments, the method further comprises (d) further administering the bacterial composition to the patient or ceasing administration of the bacterial composition to the patient based on the comparison in (c). In the monitoring method described herein, a variety of known methods can be used for determining the percentage or absolute counts of a bacterial species. For example, 16S rRNA sequencing can be used.

<Method to Obtain Th17-Inducing Bacterial Compositions>

Certain modifications applied to a fecal sample can result in the obtention of Th17-inducing bacterial compositions. Surprisingly, administration of ampicillin to animals enriches the representation of Th17-inducing strains in a sample. Culturing serially diluted samples from ampicillin-treated animals by plating under strictly anaerobic conditions in certain media described in Example 2 led to obtention of potent Th17-inducing bacterial compositions. Accordingly, provided is a method of obtaining Th17-inducing bacterial compositions, comprising (a) treating a subject with the antibiotic ampicillin, or an antibiotic with a similar spectrum, for example an aminopenicillin family member such as amoxicillin, penicillin, or benzylpenicillin; (b) obtaining (a, one or more, at least one) sample, such as a fecal sample or an intestinal biopsy from the subject; (c) culturing the sample from (b) and isolating pure bacterial strains from the resulting colonies. In a preferred embodiment the subject in (a) is an ex-germ-free animal that is first colonized with a fecal sample obtained from a human donor, and afterwards is treated with ampicillin, after which cecal samples are obtained from the animal and cultured as described in Example 2. In one embodiment, the isolation of pure bacterial strains of (c) is performed by serial dilutions of cecal content samples cultured by plating under a strictly anaerobic condition. In another embodiment, the method comprises (a) obtaining (at least one) sample, such as a fecal sample or an intestinal biopsy from a subject; (b) treating the sample of (a) with ampicillin; (c) culturing the ampicillin-treated sample of (b) and isolating pure bacterial strains.

<Method of Use of the Th17-Inducing Bacterial Compositions to Repopulate the Microbiota of Individuals Receiving Antibiotic Treatment>

The bacterial composition can be administered to an individual who is also receiving antibiotic treatment. The present inventors have demonstrated that antibiotics such as vancomycin or metronidazole can effectively eliminate or greatly reduce Th17-inducing bacterial species from the gastrointestinal tract of mammals and subsequently decrease the levels of Th17 cells (Example 1). Without wishing to be bound by theory, the key role of Th17-inducing bacteria promoting immune responses strongly indicates that their presence or high levels can play a key role in autoimmune diseases. Accordingly, individuals undergoing courses of antibiotics such as vancomycin or metronidazole, who are at a high risk of experiencing a loss of Th17-inducing bacteria and thus experience immune deficits, can be preventively "repopulated" through use of the bacterial compositions. The bacterial compositions can be administered before, simultaneously with, or after the antibiotic treatment, but preferably are administered simultaneously or after the antibiotic treatment.

Following are examples, which describe specific aspects. They are not intended to be limiting in any way.

EXAMPLES

Example 1

Human stool (2 g) from an ulcerative colitis (UC) Japanese patient in a clinically active state was suspended with 8 ml phosphate-buffered saline (PBS) containing 20% glycerol, snap-frozen in liquid nitrogen, and stored at −80° C. until use. The frozen stock was thawed, and orally inoculated into IQI germ-free (GF) mice (250 μl/mouse). The mice were given ampicillin (ABPC; 1 g/L), vancomycin (VCM; 500 mg/L), polymyxin B (PL-B; 200 mg/L), metronidazole (MNZ; 1 g/L), or water only (non-treated: NT) in their drinking water beginning 1 d after the inoculation with UC patient feces until the day of analysis. Each group of ex-GF mice (n=5 for each group) was separately kept in a vinyl isolator for 4 weeks.

The colons were collected and opened longitudinally, washed with PBS to remove all luminal contents and shaken in Hanks' balanced salt solution (HBSS) containing 5 mM EDTA for 20 min at 37° C. After removing epithelial cells, muscle layers and fat tissue using forceps, the lamina propria layers were cut into small pieces and incubated with RPMI1640 containing 4% fetal bovine serum (FBS), 0.5 mg/mL collagenase D, 0.5 mg/mL dispase and 40 mg/mL DNase I (all Roche Diagnostics) for 1 h at 37° C. in a shaking water bath. The digested tissues were washed with HBSS containing 5 mM EDTA, resuspended in 5 mL of 40% Percoll (GE Healthcare) and overlaid on 2.5 ml of 80% Percoll in a 15-ml Falcon tube. Percoll gradient separation was performed by centrifugation at 800 g for 20 min at 25° C. The lamina propria lymphocytes were collected from the interface of the Percoll gradient and suspended in RPMI1640 containing 10% FBS. For analysis of Th1 and Th17 cells, isolated lymphocytes were stimulated for 4 h with 50 ng/mL phorbol 12-myristate 13-acetate (PMA, Sigma) and 750 ng/mL ionomycin (Sigma) in the presence of GolgiStop (BD Biosciences). After incubation for 4 h, cells were washed in PBS, labelled with the LIVE/DEAD fixable dead cell stain kit (Invitrogen) and surface CD4 and CD3 were stained with PECy7-labelled anti-CD4 Ab (RM4-5, BD Biosciences) and BV605-labelled anti-CD3 Ab (17A2, BioLegend). Cells were washed, fixed and permeabilized with Foxp3 Staining Buffer set (eBioscience), and stained with the APC-labelled anti-IL-17 Ab (eBio 17B7, eBioscience) and BV421-labelled anti-IFN-g Ab (XMG1.2, BioLegend). The Ab stained cells were analyzed with LSR Fortessa (BD Biosciences), and data were analyzed using FlowJo software (Treestar).

Figure 1B:
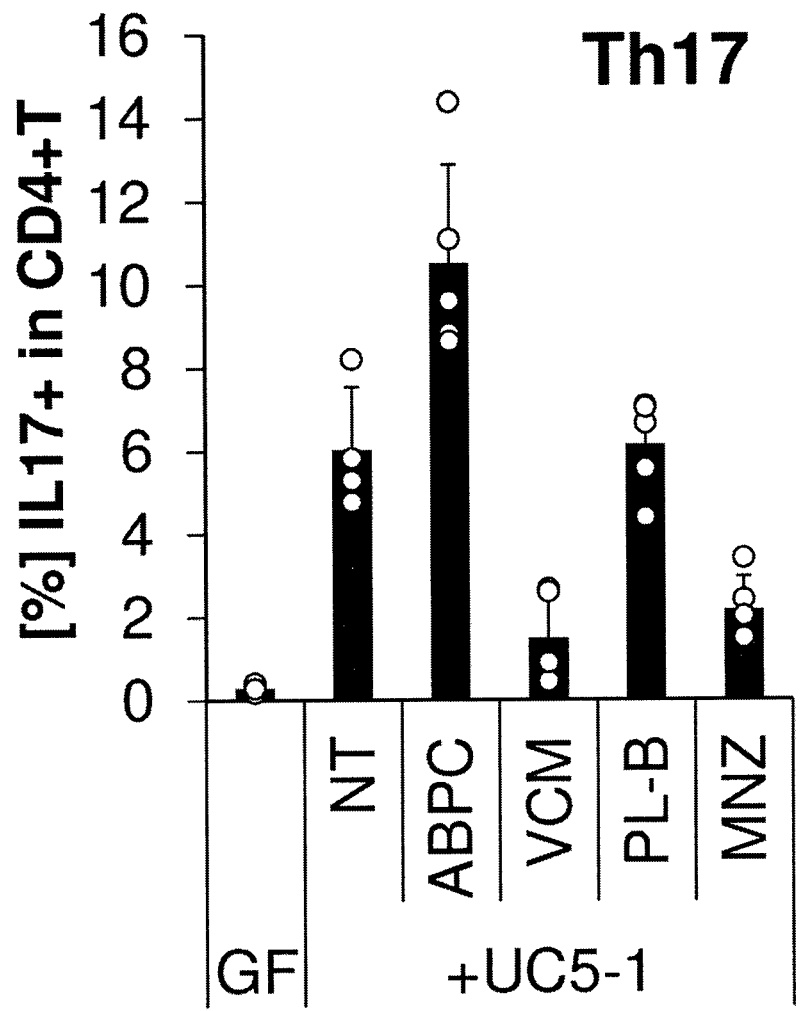
FIG. 1B is a graph showing analysis results of the ratios of IL-17+ cells in CD4+ lymphocytes of germ-free mice (GF), GF mice colonized with stool from ulcerative colitis patients and untreated (NT), and GF mice colonized with stool from ulcerative colitis patients and treated with ampicillin (ABPC) or vancomycin (VCM) or polymyxin-B (PL-B) or metronidazole (MNZ) in the drinking water.

In mice orally inoculated with UC patient feces, substantial induction of Th17 cells was observed. Surprisingly, the Th17 induction was enhanced in mice given ampicillin (ABPC) in the drinking water, compared with mice given water only (non-treated: NT). In contrast, Th17 induction was significantly impaired by the treatment with vancomycin (VCM) or metronidazole (MNZ). On the other hand, treatment with polymyxin B (PL-B) did not affect Th17 cell numbers (FIG. 1).

Therefore, Th17-inducing bacteria are present in the human feces, and the bacterial species are resistant to ampicillin and polymyxin B, but sensitive to vancomycin and metronidazole.

Example 2

The caecal contents from each exGF mice described in Example 1 were suspended in 10 mL of Tris-EDTA containing 10 mM Tris-HCl and 1 mM EDTA (pH 8), and incubated with Lysozyme (SIGMA, 15 mg/mL) at 37° C. for 1 h with gentle mixing. A purified achromopeptidase (Wako) was added (final concentration 2000 unit/mL) and incubated at 37° C. for another 30 min. Then, sodium dodecyl sulfate (final concentration 1%) was added to the cell suspension and mixed well. Subsequently, proteinase K (Merck) was added (final concentration 1 mg/mL) to the suspension and the mixture was incubated at 55° C. for 1 h. High-molecular-weight DNA was isolated and purified by phenol/chloroform extraction, ethanol, and finally polyethyleneglycol precipitation. PCR was performed using Ex Taq (TAKARA) and (i) modified primer 8F [5'-CCATCTCATCCCTGCGTGTCTC-CGACTCAG (454 adaptor sequence, SEQ ID NO.: 21)+Barcode (10 bases)+AGRGTTTGATYMTGGCTCAG (SEQ ID NO.: 22)-3'] and (ii) modified primer 338R [5'-CCTATCCCCTGTGTGCCTTGGCAGTCTCAG (454 adaptor sequence, SEQ ID NO.: 23)+TGCTGCCTCCCG-TAGGAGT (SEQ ID NO.: 24)-3'] to the V1-V2 region of the 16S rRNA gene. Amplicons generated from each sample (~330 bp) were subsequently purified using AMPure XP (BECKMAN COULTER). The amount of DNA was quantified using Quant-iT Picogreen dsDNA Assay Kit (Invitrogen) and TBS-380mini Fluorometer (Turner Biosystems). Then, the amplified DNA was used as template for IonPGM sequencer. Resulting sequences (3000 reads were produced for each sample) were classified into OTUs based on sequence similarity (≥96% identity). Representative sequences from each OTU were compared with sequences in nucleic acid databases (Ribosomal Database Project) or GenomeDB (NCBI+HMP+Hattori Lab data base) using BLAST to determine the closest strains.

Figure 2:
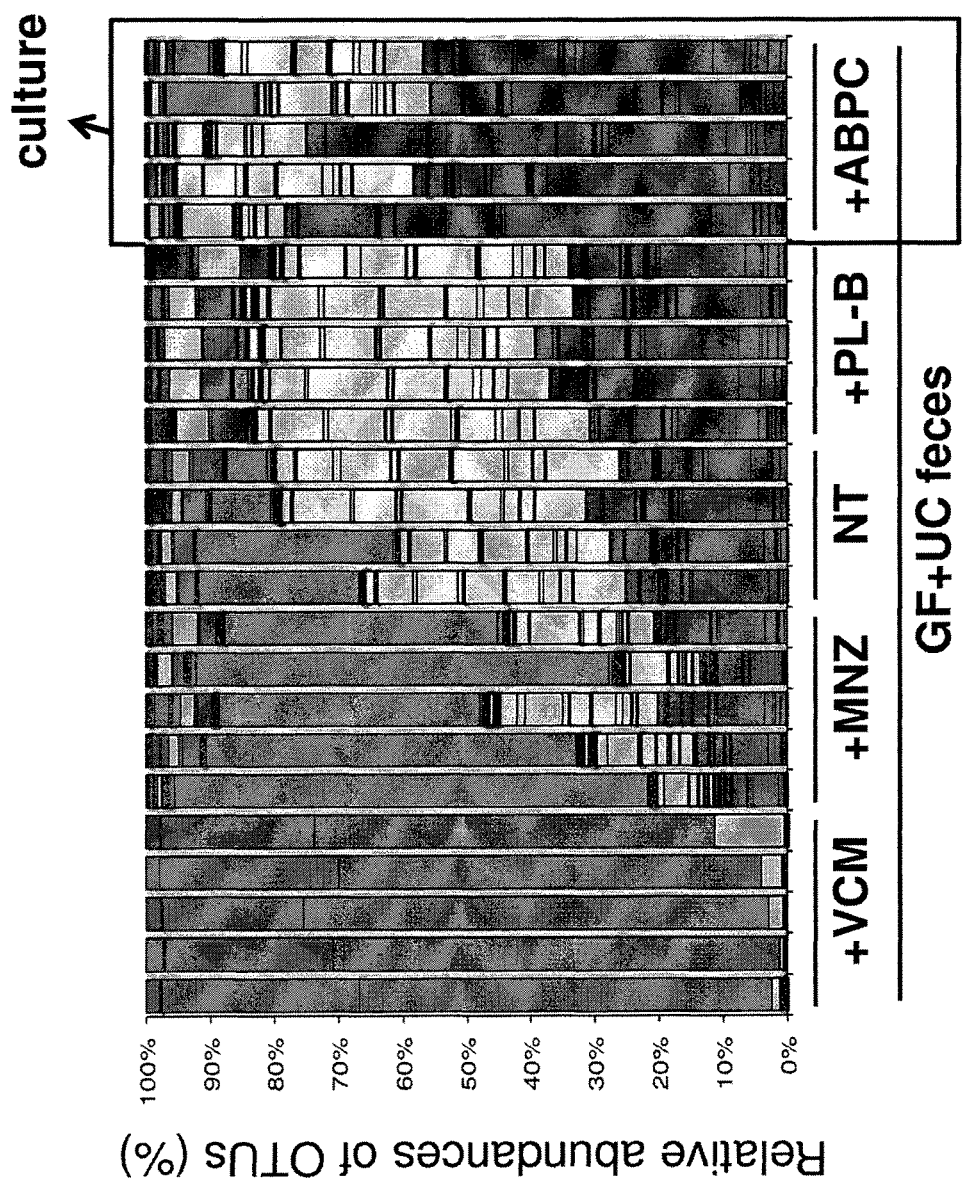
FIG. 2 shows the relative abundance of OTUs having the same closest relative in cecal samples from IQI Germ Free mice colonized with human stool from an ulcerative colitis patient and given water only (non-treated: NT) or given ampicillin (+ABPC; 1 g/L), or vancomycin (+VCM; 500 mg/L), or polymyxin B (+PL-B; 200 mg/L), or metronidazole (+MNZ; 1 g/L) in the drinking water; n=5 for each group. OTUs negatively correlated with Th17 cell number are depicted in blue or grey, and OTUs positively correlated with Th17 cell number are marked with red.

OTUs negatively correlated with Th17 cell number are depicted in FIG. 2 in blue or grey, and OTUs positively correlated with Th17 cell number are marked with red.

Serial dilutions of the cecal contents from mice colonized with UC patient feces and given ampicillin were cultured by plating under a strictly anaerobic condition (80% $N_2$ 10% $H_2$ 10% $CO_2$) on BL agar (Eiken Chemical) supplemented with 5% defibrinated horse blood (Nippon Bio-Supp. Center), GAM agar (Nissui) supplemented with 5% defibrinated horse blood, Tryptic soy agar (Becton Dickinson) supplemented with 5% defibrinated horse blood, Reinforced clostridial agar (Oxoid) supplemented with 5% defibrinated horse blood, Schaedler agar (Becton Dickinson) or Brain Heart Infusion agar (Becton Dickinson). After culture at 37° C. for 2 days, each single colony was picked up (250 colonies in total) and stocked in Schaedler Broth (Becton Dickinson) containing 10% glycerol at −80° C. To identify the isolated strains, the 16S rRNA genes were amplified by colony-PCR using KOD FX (TOYOBO) and 16S rRNA gene-specific primer pairs: 8F (5'-AGAGTTTGATCMTG-GCTCAG-3') (SEQ ID NO.: 25) and 1492R (5'-GGYTAC-CTTGTTACGACTT-3') (SEQ ID NO.: 26). The amplification program consisted of one cycle at 98° C. for 2 min, followed by 35 cycles at 98° C. for 10 s, 57° C. for 30 s and 68° C. for 90 s. Each amplified DNA was purified from the reaction mixture using AMPure XP. Sequence analysis was performed using BigDye Terminator V3.1 Cycle Sequencing Kit (Applied Biosystems) and Applied Biosystems 3730xl DNA analyzer (Applied Biosystems). The resulting sequences were compared with sequences in the RDP database to determine the closest relatives. BLAST search of 16S rRNA gene sequences of these picked-up colonies revealed that we succeeded in isolating 20 strains (Table 1).

Example 3

Figure 3A:
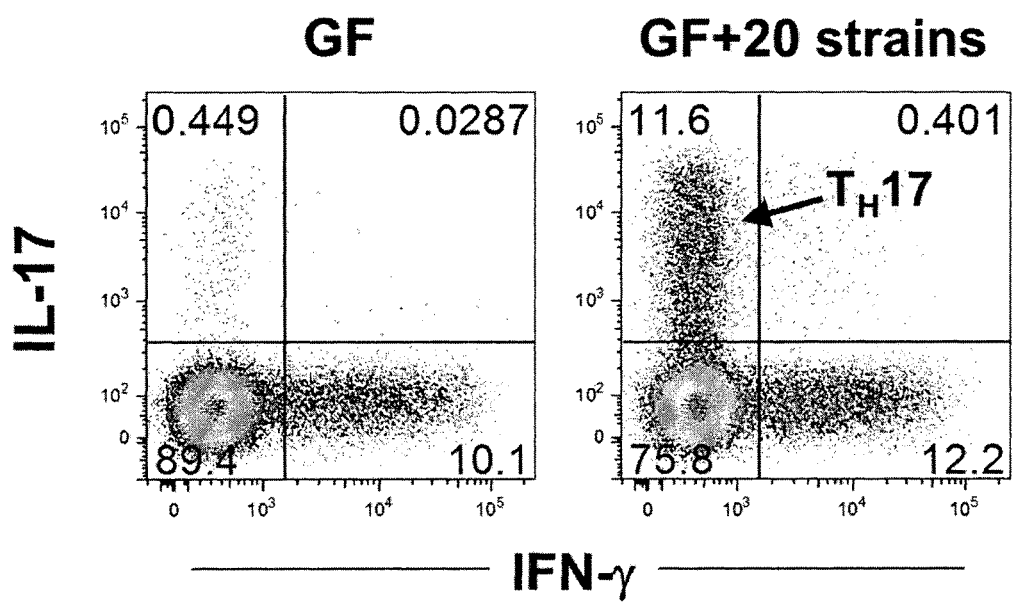
FIG. 3A shows the percentages of IL-17+ cells and IFN-g+ within the CD4+ T cell population in the colon lamina propria of germ-free mice and germ-free mice colonized with the 20 strains listed in Table 1.
Figure 3B:
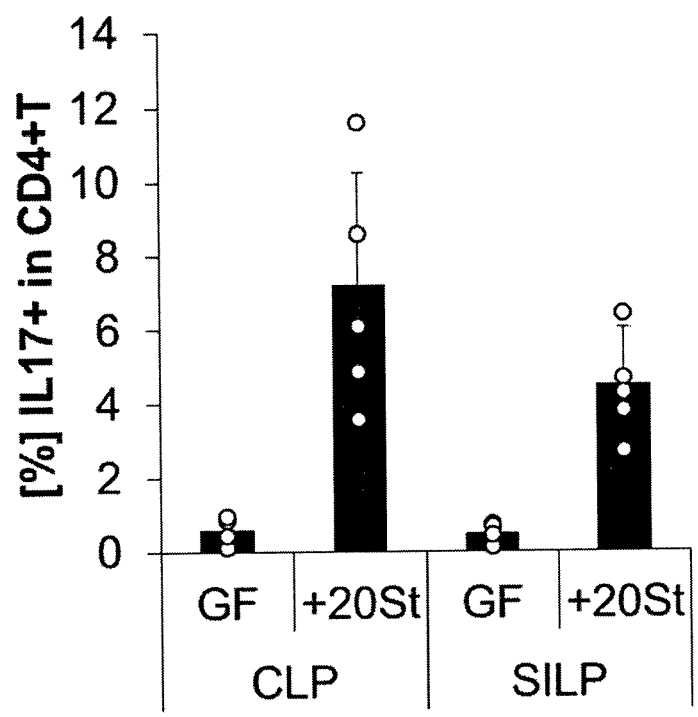
FIG. 3B is a graph showing analysis results of the ratios of IL-17+ cells in CD4+ lymphocytes in the Colon Lamina Propria (CLP) or Small Intestine Lamina Propria (SILP) of germ-free mice compared to germ-free mice colonized with the 20 strains listed in Table 1.

To investigate whether the isolated 20 strains (Table 1) have the ability to induce Th17 cells, all 20 strains were cultured and mixed to make a cocktail, and the cocktail was orally inoculated into GF mice. The isolated 20 strains were individually cultured in Schaedler or PYG broth under a strictly anaerobic condition (80% $N_2$, 10% $H_2$, 10% $CO_2$) at 37° C. in an anaerobic chamber (Coy Laboratory Products), and then mixed at equal amounts of media volume to prepare the bacterial mixture. The aliquot of bacterial mixture was orally inoculated into mice (0.5 ml/mouse). After 4 weeks, the colons and small intestines were collected and analyzed for Th17 and Th1 cells. The percentages of IL-17+ cells and IFN-g+ within the CD4+ T cell population in the colon lamina propria and small intestine lamina propria of the indicated mice are shown in FIG. 3. In mice colonized with the 20 strains, a strong induction of Th17 cells was observed.

SEQ ID Nos.: 2H6, 1B11, 1D10, 2E3, 1C12, 2G4, 2H11, 1E11, 2D9, 2F7, 1D1, 1F8, 1C2, 1D4, 1E3, 1A9, 2G11, 2E1, 1F7, 1D2, are SEQ ID Nos. 1-20 respectively.

INDUSTRIAL APPLICABILITY

As has been described above, the compositions and methods described herein make it possible to provide an excellent and well-characterized composition for inducing proliferation or accumulation of Th17 by utilizing certain human-derived bacteria or supernatants or the like derived from the bacteria. Since the bacterial composition has the effects of promoting immune responses, the bacterial composition can be used, for example, to treat infections, as well as to prevent infections as a component of a mucosal vaccine. In addition, healthy individuals can easily and routinely ingest the bacterial composition, such as in food or beverage, (e.g., a health food), to improve their immune functions.

This application is based on an U.S. provisional patent application No. 61/978,182 (filing date: Apr. 10, 2014), the contents of which are incorporated in full herein.

TABLE 1

| SEQ ID# | strain# | identity | species |
|---|---|---|---|
| 1 | 2H6 | 0.975 | Clostridium ramosum |
| 2 | 1B11 | 1.000 | Bifidobacterium pseudolongum subsp. pseudolongum |
| 3 | 1D10 | 0.962 | Clostridium lactatifermentans |
| 4 | 2E3 | 0.777 | Blautia sp. canine oral taxon 143 |
| 5 | 1C12 | 0.926 | cf. Clostridium sp. MLG055 |
| 6 | 2G4 | 0.995 | Clostridium innocuum |
| 7 | 2H11 | 0.999 | Clostridium orbiscindens |
| 8 | 1E11 | 0.941 | Ruminococcus sp. 16442 |
| 9 | 2D9 | 0.954 | Ruminococcus gnavus |
| 10 | 2F7 | 0.749 | Anaerotruncus colihominis |
| 11 | 1D1 | 0.857 | Eubacterium desmolans |
| 12 | 1F8 | 0.959 | Clostridium hathewayi |
| 13 | 1C2 | 0.993 | Bifidobacterium breve |
| 14 | 1D4 | 0.959 | Ruminococcus sp. M-1 |
| 15 | 1E3 | 0.977 | Coprobacillus cateniformis |
| 16 | 1A9 | 0.967 | Clostridium symbiosum |
| 17 | 2G11 | 0.991 | Bacteroides dorei |
| 18 | 2E1 | 0.964 | Anaerostipes caccae |
| 19 | 1F7 | 0.958 | Clostridium bolteae |
| 20 | 1D2 | 0.783 | Clostridium citroniae |

TABLE 2

>2H6 (SEQ ID NO.: 1)

```
GGGGCGGCTGCTATAATGCAGTCGACGCGAGCACTTGTGCTCGAGTGGCG
AACGGGTGAGTAATACATAAGTAACCTGCCCTAGACAGGGGGATAACTAT
TGGAAACGATAGCTAAGACCGCATATGTACGGACACTGCATGGTGACCGT
ATTAAAAGTGCCTCAAAGCACTGGTAGAGGATGGACTTATGGCGCATTAG
CTGGTTGGCGGGGTAACGGCCCACCAAGGCGACGATGCGTAGCCGACCTG
AGAGGGTGACCGGCCACACTGGGACTGAGACACGGCCCAGACTCCTACGG
GAGGCAGCAGTAGGGAATTTTCGGCAATGGGGGAAACCCTGACCGAGCAA
CGCCGCGTGAAGGAAGAAGGTTTTCGGATTGTAAACTTCTGTTATAAAGG
```

TABLE 2-continued

>2H6 (SEQ ID NO.: 1)

```
AAGAACGGCGGCTACAGGAAATGGTAGCCGAGTGACGGTACTTTATTAGA
AAGCCACGGCTAACTACGTGCCAGCAGCCGCGGTAATACGTAGGTGGCAA
GCGTTATCCGGAATTATTGGGCGTAAAGAGGGAGCAGGCGGCAGCAAGGG
TCTGTGGTGAAAGCCTGAAGCTTAACTTCAGTAAGCCATAGAAACCAGGC
AGCTAGAGTGCAGGAGAGGATCGTGGAATTCCATGTGTAGCGGTGAAATG
CGTAGATATATGGAGGAACACCAGTGGCGAAGGCGACGATCTGGCCTGCA
ACTGACGCTCAGTCCCGAAAGCGTGGGGAGCAAATAGGATTAGATACCCT
AGTAGTCCACGCCGTAAACGATGAGTACTAAGTGTTGGATGTCAAAGTTC
AGTGCTGCAGTTAACGCAATAAGTACTCCGCCTGAGTAGTACGTTCGCAA
GAATGAAACTCAAAGGAATTGACGGGGGCCCGCACAAGCGGTGGAGCATG
TGGTTTAATTCGAAGCAACGCGAAGAACCTTACCAGGTCTTGACATACTC
ATAAAGGCTCCAGAGATGGAGAGATAGCTATATGAGATACAGGTGGTGCA
TGGTTGTCGTCAGCTCGTGTCGTGAGATGTTGGGTTAAGTCCCGCAACGA
GCGCAACCCTTATCGTTAGTTACCATCATTAAGTTGGGGACTCTAGCGAG
ACTGCCAGTGACAAGCTGGAGGAAGGCGGGGATGACGTCAAATCATCATG
CCCCTTATGACCTGGGCTACACACGTGCTACAATGGATGGTGCAGAGGGA
AGCGAAGCCGCGAGGTGAAGCAAAACCCATAAAACCATTCTCAGTTCGGA
TTGTAGTCTGCAACTCGACTACATGAAGTTGGAATCGCTAGTAATCGCGA
ATCAGCATGTCGCGGTGAATACGTTCTCGGGCCTTGTACACACCGCCCGT
CACACCACGAGAGTTGATAACACCCGAAGCCGGTGGCCTAACCGCAAGGA
AGGAGCTTCTAAGGTGGAT
```

TABLE 3

>1B11 (SEQ ID NO.: 2)

```
CTGCGGCGTCTACCATGCAGTCGAACGGGATCCCTGGCAGCTTGCTGCCG
GGGTGAGAGTGGCGAACGGGTGAGTAATGCGTGACCGACCTGCCCCATGC
ACCGGAATAGCTCCTGGAAACGGGTGGTAATGCCGGATGTTCCACATGAG
CGCATGCGAGTGTGGGAAAGGCTTTTTGCGGCATGGGATGGGGTCGCGTC
CTATCAGCTTGTTGGTGGGGTAACGGCCTACCAAGGCGTTGACGGGTAGC
CGGCCTGAGAGGGCGACCGGCCACATTGGGACTGAGATACGGCCCAGACT
CCTACGGGAGGCAGCAGTGGGGAATATTGCACAATGGGCGCAAGCCTGAT
GCAGCGACGCCGCGTGCGGGATGGAGGCCTTCGGGTTGTAAACCGCTTTT
GTTCAAGGGCAAGGCACGGTCTTTGGCCGTGTTGAGTGGATTGTTCGAAT
AAGCACCGGCTAACTACGTGCCAGCAGCCGCGGTAATACGTAGGGTGCAA
GCGTTATCCGGATTTATTGGGCGTAAAGGGCTCGTAGGCGGTTCGTCGCG
TCCGGTGTGAAAGTCCATCGCTTAACGGTGGATCCGCGCGGGTACGGGC
GGGCTTGAGTGCGGTAGGGGAGACTGGAATTCCCGGTGTAACGGTGGAAT
GTGTAGATATCGGGAAGAACACCAATGGCGAAGGCAGGTCTCTGGGCCGT
TACTGACGCTGAGGAGCGAAAGCGTGGGGAGCGAACAGGATTAGATACCC
TGGTAGTCCACGCCGTAAACGGTGGATGCTGGATGTGGGGCCCTTTTCC
GGGTCCTGTGTCGGAGCTAACGCGTTAAGCATCCCGCCTGGGGAGTACGG
CCGCAAGGCTAAAACTCAAAGAAATTGACGGGGGCCCGCACAAGCGGCGG
AGCATGCGGATTAATTCGATGCAACGCGAAGAACCTTACCTGGGCTTGAC
ATGTGCCGGACGCCCGCGGAGACGCGGGTTCCCTTCGGGGCCGGTTCACA
GGTGGTGCATGGTCGTCGTCAGCTCGTGTCGTGAGATGTTGGGTTAAGTC
CCGCAACGAGCGCAACCCTCGCCGCGTGTTGCCAGCGGGTCATGCCGGGA
ACTCACGTGGGACCGCCGGGGTTAACTCGGAGGAAGGTGGGGATGACGTC
AGATCATCATGCCCCTTACGTCCAGGGCTTCACGCATGCTACAATGGCCG
GTACAACGGGTGCGACACGGTGACGTGGGCGGATCCCTGAAAACCGGT
CTCAGTTCGGATCGCAGTCTGCAACTCGACTGCGTGAAGGTGGAGTCGCT
AGTAATCGCGGATCAGCAACGCCGCGGTGAATGCGTTCCCGGGCCTTGTA
CACACCGCCCGTCAAGTCATGAAAGTGGGCAGCACCCGAAGACGGTGGCC
TAACCCTTGTGGGGGAGCCGTCTAAGGTAGTG
```

TABLE 4

>1D10 (SEQ ID NO.: 3)

```
CTGCCGGCTCTACCATGCAGTCGAACGAAGATAGTTAGAATGAGAGCTTC
GGCAGGATTTTTTTCTATCTTAGTGGCGGACGGGTGAGTAACGTGTGGGC
AACCTGCCCTGTACTGGGGAATAATCATTGGAAACGATGACTAATACCGC
ATGTGGTCCTCGGAAGGCATCTTCTGAGGAAGAAAAGGATTTATTCGGTAC
AGGATGGGCCCGCATCTGATTAGCTAGTTGGTGAGATAACAGCCCACCAA
GGCGACGATCAGTAGCCGACCTGAGAGGGTGATCGGCCACATTGGGACTG
AGACACGGCCCAAACTCCTACGGGAGGCAGCAGTGGGGAATATTGCACAA
TGGGCGAAAGCCTGATGCAGCAACGCCGCGTGAAGGATGAAGGGTTTCGG
CTCGTAAACTTCTCAATAAGGGAAGAAACAAATGACGGTACCTAAATAA
GAAGCCCCGGCTAACTACGTGCCAGCAGCCGCGGTAATACGTAGGGGGCA
AGCGTTATCCGGAATTACTGGGTGTAAAGGGAGCGTAGGCGGCATGGTAA
GCCAGATGTGAAAGCCTTGGGCTTAACCCGAGGATTGCATTTGGAACTAT
CAAGCTAGAGTACAGGAGAGGAAAGCGGAATTCCTAGTGTAGCGGTGAAA
```

TABLE 4-continued

>1D10 (SEQ ID NO.: 3)

TGCGTAGATATTAGGAAGAACACCAGTGGCGAAGGCGGCTTTCTGGACTG
AAACTGACGCTGAGGCTCGAAAGCGTGGGGAGCAAACAGGATTAGATACC
CTGGTAGTCCACGCCGTAAACGATGAGTGCTAGGTGTCGGGGAGGAATCC
TCGGTGCCGCAGCTAACGCAATAAGCACTCCACCTGGGGAGTACGACCGC
AAGGTTGAAACTCAAAGGAATTGACGGGGGCCCGCACAAGCGGTGGAGCA
TGTGGTTTAATTCGAAGCAACGCGAAGAACCTTACCAAGGCTTGACATCC
CGATGACCGTCCTAGAGATAGGACTTCTCTTCGGAGCATCGGTGACAGGT
GGTGCATGGTTGTCGTCAGCTCGTGTCGTGAGATGTTGGGTTAAGTCCCG
CAACGAGCGCAACCCTTATCTTCAGTAGCCATCATTCAGTTGGGCACTCT
GGAGAGACTGCCGTGGATAACACGGAGGAAGGTGGGGATGACGTCAAATC
ATCATGCCCCTTATGTCTTGGGCTACACACGTGCTACAATGGCTGGTAAC
AAAGTGACGCGAGACGGCGACGTTAAGCAAATCACAAAAACCCAGTCCCA
GTTCGGATTGTAGTCTGCAACTCGACTACATGAAGCTGGAATCGCTAGTA
ATCGCGAATCAGCATGTCGCGGTGAATACGTTCCCGGGCCTTGTACACAC
CGCCCGTCACACCATGGAGTTGGAAGCACCCGAAGTCGGTGACCTAACC
GTAAGGAAGAGCCGCCGAAGTAGGGGAT

TABLE 5

>2E3 (SEQ ID NO.: 4)

CGGCGCTCTACCATGCAGTCGACGAAGCGATTTGAATGAAGTTTTCGGAT
GGATTTTAAATTGACTGAGTGGCGGACGGGTGAGTAACGCGTGGGTAACC
TGCCCCATACAGGGGGATAACAGTTAGAAATGACTGCTAATACCGCATAA
GACCACAGCGCCGCATGGTGCAGGGGTAAAACTCCGGTGGTATGGGATG
GACCCGCGTCTGATTAGCTTGTTGGCGGGGTAACGGCCCACCAAGGCGAC
GATCAGTAGCCGACCTGAGAGGGTGACCGGCCACATTGGGACTGAGACAC
GGCCCAAACTCCTACGGGAGGCAGCAGTAGGGAATATTGCACAATGGGGG
AAACCCTGATGCAGCGACGCCGCGTGAGTGATGAAGTATTTCGGTATGTA
AAGCTCTATCAGCAGGGAAGAAAATGACGTACCTGACTAAGAAGCCCCG
GCTAACTACGTGCCAGCAGCCGCGGTAATACGTAGGGGGCAAGCGTTATC
CGGATTTACTGGGTGTAAAGGGAGCGTAGACGGCTGTGCAAGTCTGGAGT
GAAAGCCCGGGGCTCAAACCCCGGGACTGCTTTGGAAACTGTACGGCTGA
GTGCTGGAGAGGCAAGCGGAATTCCTAGTGTAGCGGTGAAATGCGTAGAT
ATTAGGAGGAACACCAGTGGCGAAGGCGGCTTGCTGGACAGTAACTGACG
TTGAGGCTCGAAAGCGTGGGGAGCAAACAGGATTAGATACCCTGGTAGTC
CACGCCGTAAACGATGAATGCTAGGTGTCGGGGAGCAAAGCTCTTCGGTG
CCGCCGAAACGCAATAAGCATTCCACCTGGGGAGTACGTTCGCAAGAAT
GAAACTCAAAGGAATTGACGGGGACCCGCACAAGCGGTGGAGCATGTGGT
TTAATTCGAAGCAACGCGAAGAACCTTACCAAGTCTTGACATCCCCCTGA
CCGGCAAGTAATGTCGCCTTTCCTTCGGGACAGGGGAGACAGGTGGTGCA
TGGTTGTCGTCAGCTCGTGTCGTGAGATGTTGGGTTAAGTCCCGCAACGA
GCGCAACCCTTATCCTCAGTAGCCAGCAGGTGAAGCTGGGCACTCTGTGG
AGACTGCCAGGGATAACCTGGAGGAAGGTGGGGACGACGTCAAATCATCA
TGCCCCTTATGACTTGGGCTACACACGTGCTACAATGGCGTAAACAAAGG
GAAGCGAGAGGGTGACCTGGAGCAAATCCCAAAAATAACGTCTCAGTTCG
GATTGTAGTCTGCAACTCGACTACATGAAGCTGGAATCGCTAGTAATCGC
GAATCAGCATGTCGCGGTGAATACGTTCCCGGGTCTTGTACACACCGCCC
GTCACACCATGGGAGTCAGCAACGCCCGAAGCCGGTGACCTAACCGCAAG
GAAGGAGCCGTCGAAGTCGTCG

TABLE 6

>1C12 (SEQ ID NO.: 5)

CGGCGCTGCTATACTGCAGTCGAACGAAGCGAAGGTAGCTTGCTATCGGA
GCTTAGTGGCGAACGGGTGAGTAACACGTAGATAACCTGCCTGTATGACC
GGGATAACAGTTGGAAACGACTGCTAATACCGGATAGGCAGAGAGGAGGC
ATCTCTTCTCTGTTAAAGTTGGGATACAACGCAAACAGATGGATCTGCGG
TGCATTAGCTAGTTGGTGAGGTAACGGCTCACCAAGGCGATGATGCATAG
CCGGCCTGAGAGGGCGAACGGCCACATTGGGACTGAGACACGGCCCAAAC
TCCTACGGGAGGCAGCAGTAGGGAATTTTCGGCAATGGGGGAAACCCTGA
CCGAGCAATGCCGCGTGAGTGAAGACGGCCTTCGGGTTGTAAAGCTCTGT
TGTAAGGGAAGAACGGCATAGAGGGGAATGCTCTATGGTGACGGTACC
TTACCAGAAAGCCACGGCTAACTACGTGCCAGCAGCCGCGGTAATACGTA
GGTGGCAAGCGTTATCCGGAATTATTGGGCGTAAAGGGTGCGTAGGCGGC
TGGATAAGTCTGAGGTAAAAGCCCGTGGCTCAACCACGGTAAGCCTTGGA
AACTGTCTGGACTTGAGTGCAGGAGAGGACAATGGAATTCCATGTGTAGC
GGTAAAATGCGTAGATATATGAGGAACACCAGTGGCGAAGGCGGTTGTCT
GGCCTGTAACTGACGCTGAAGCACGAAAGCGTGGGGAGCAAATAGGATTA
GATACCCTAGTAGTCCACGCCGTAAACGATGAGAACTAAGTGTTGGGAA
ACTCAGTGCTGCAGTTAACGCAATAAGTTCTCCGCCTGGGGAGTATGCAC
GCAAGTGTGAAACTCAAAGGAATTGACGGGGGCCCGCACAAGCGGTGGAG

TABLE 6-continued

>1C12 (SEQ ID NO.: 5)

TATGTGGTTTAATTCGACGCAACGCGAAGAACCTTACCAGGCCTTGACAT
GGTATCAAAGGCCCTAGAGATAGGGAGATAGGTATGATACACACAGGTG
TGCATGGTTGTCGTCAGCTCGTGTCGTGAGATGTTGGGTTAAGTCCCGCA
ACGAGCGCAACCCTTGTTTCTAGTTACCAACAGTAAGATGGGGACTCTAG
AGAGACTGCCGGTGACAAACCGGAGGAAGGTGGGGATGACGTCAAATCAT
CATGCCCCTTATGGCCTGGGCTACACACGTACTACAATGGCGTCTACAAA
GAGCAGCGAGCAGGTGACTGTAAGCGAATCTCATAAAGGACGTCTCAGTT
CGGATTGAAGTCTGCAACTCGACTTCATGAAGTCGGAATCGCTAGTAATC
GCGGATCAGCATGCCGCGGTGAATACGTTCTCGGGCCTTGTACACACCGC
CCGTCAAACCATGGGAGTTGATAATACCCGAAGCCGGTGGCCTAACCGAA
AGGAGGGAGCCGTCGAAGTAGATTG

TABLE 7

>2G4 (SEQ ID NO.: 6)

CGGCGCTGCTATAATGCAGTCGAACGAAGTTTCGAGGAAGCTTGCTTCCA
AAGAGACTTAGTGGCGAACGGGTGAGTAACACGTAGGTAACCTGCCCATG
TGTCCGGGATAACTGCTGGAAACGGTAGCTAAAACCGGATAGGTATACAG
AGCGCATGCTCAGTATATTAAAGCGCCCATCAAGGCGTGAACATGGATGG
ACCTGCGGCGCATTAGCTAGTTGGTGAGGTAACGGCCCACCAAGGCGATG
ATGCGTAGCCGGCCTGAGAGGGTAAACGGCCACATTGGGACTGAGACACG
GCCCAAACTCCTACGGGAGGCAGCAGTAGGGAATTTTCGTCAATGGGGGA
AACCCTGAACGAGCAATGCCGCGTGAGTGAAGAAGGTCTTCGGATCGTAA
AGCTCTGTTGTAAGTGAAGAACGGCTCATAGAGGGAAATGCTATGGGAGTG
ACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCG
TAGGTGGCGTACTAAGTCTGTAGTAAAAAGGCAATGGCTCAACCATTGTAA
GCTATGAAACTGTATGCTGTGGAGTGCAGAAGAGGGCGATGGAATTCCAT
GTGTAGCGGTAAAATGCGTAGATATATGGAGGAACACCAGTGGCGAAGGC
GGTCGCCTGGTCTGTAACTGACACTGAGGCACGAAAGCGTGGGGAGCAAA
TAGGATTAGATACCCTAGTAGTCCACGCCGTAAACGATGAGAACTAAGTG
TTGAGGAATTCAGTGCTGCAGTTAACGCAATAAGTTCTCCGCCTGGGGA
GTATGCACGCAAGTGTGAAACTCAAAGGAATTGACGGGGGCCCGCACAAG
CGGTGGAGTATGTGGTTTAATTCGAAGCAACGCGAAGAACCTTACCAGGC
CTTGACATGATGGAACAATGCCCTAGAGATAGGAGATAATTATGGATCAC
ACAGGTGGTGCATGGTTGTCGTCAGCTCGTGTCGTGAGATGTTGGGTTAA
GTCCCGCAACGAGCGCAACCCTTGTCGCATGTTACCAGCATCAAGTTGGG
GACTCATGCGAGACTGCCGGTGACAAACCGGAGGAAGGTGGGGATGACGT
CAAATCATCATGCCCCTTATGGCCTGGGCTACACGTACTACAATGGCG
ACCACAAAGAGCAGCGACACAGTGATGTGAAGCGAATCTCATAAAGTCG
CTCAGTTCGGATTGAAGTCTGCAACTCGACTTCATGAAGTCGGAATCGCT
AGTAATCGCAGATCAGCATGCTGCGGTGAATACGTTCTCGGGCCTTGTAC
ACACCGCCCGTCAAACCATGGGAGTCAGTAATACCCGAAGCCGGTGGCAT
AACCGTAAGGAGGAGCCGTCGAAGTGACTG

TABLE 8

>2H11 (SEQ ID NO.: 7)

AGGGCGGCTCTTAAATGCAGTCGAACGGGGTGCTCATGACGGAGGATTCG
TCCAACGGATTGAGTTACCTAGTGGCGGACGGGTGAGTAACGCGTGAGGA
ACCTGCCTTGGAGAGGGGAATAACACTCCGAAAGGAGTGCTAATACCGCA
TGATGCAGTTGGGTCGCATGGCTCTGACTGCCAAAGATTTATCGCTCTGA
GATGGCCTCGCGTCTGATTAGCTAGTAGGCGGGTAACGGCCCACCTAGG
CGACGATCAGTAGCCGACCTGAGAGGGTGACCGGCCACATTGGGACTGAG
ACACGGCCCAGACTCCTACGGGAGGCAGCAGTGGGGAATATTGGGCAATG
GGCGCAAGCCTGACCCAGCAACGCCGCGTGAAGGAAGAAGGCTTTCGGGT
TGTAAACTTCTTTTGTCGGGGACGAAACAAATGACGGTACCCGACGAATA
AGCCACGGCTAACTACGTGCCAGCAGCCGCGGTAATACGTAGGTGGCAAG
CGTTATCCGGATTTACTGGGTGTAAAGGGCGTGTAGGCGGGATTGCAAGT
CAGATGTGAAAACTGGGGGCTCAACCTCCAGCCTGCATTTGAAACTGTAG
TTCTTGAGTGCTGGAGAGGCAATCGGAATTCCTGTGTAGCGGTGAAATG
CGTAGATATACAGGAGGAACACCAGTGGCGAAGGCGGATTGCTGGACAGTA
ACTGACGCTGAGGCGCGAAAGCGTGGGGAGCAAACAGGATTAGATACCCT
GGTAGTCCACGCCGTAAACGATGGATACTAGGTGTGGGGGTCTGACCCC
CTCCGTGCCGCAGTTAACACAATAAGTATCCCACCTGGGGAGTACGATCG
CAAGATTGAAACTCAAAGGAATTGACGGGGGCCCGCACAAGCGGTGGAGT
ATGTGGTTTAATTCGAAGCAACGCGAAGAACCTTACCAGGGCTTGACATC
CCACTAACGAGCAGAGATGCGTTAGGTGCCCTTCGGGGAAAGTGGAGAC
AGGTGGTGCATGGTTGTCGTCAGCTCGTGTCGTGAGATGTTGGGTTAAGT
CCCGCAACGAGCGCAACCCTTATTGTTAGTTGCTACGCAAGAGCACTCTA
GCGAGACTGCCGTTGACAAAACGGAGGAAGGTGGGGACGACGTCAAATCA

TABLE 8-continued

>2H11 (SEQ ID NO.: 7)

TCATGCCCCTTATGTCCTGGGCCACACACGTACTACAATGGTGGTTAACA
GAGGGAGGCAATACCGCGAGGTGGAGCAATCCCTAAAAGCCATCCCAGT
TCGGATTGCAGGCTGAAACCCGCCTGTATGAAGTTGGAATCGCTAGTAAT
CGCGGATCAGCATGCCGCGGTGAATACGTTCCCGGGCCTTGTACACACCG
CCCGTCACACCATGAGAGTCGGGAACACCCGAAGTCCGTAGCCTAACCGC
AAGGAGGGCGCGGCCGAAAGTTGTTCAT

TABLE 9

>1E11 (SEQ ID NO.: 8)

CGGGGGCTGCTACCATGCAGTCGAACGGAGTTAAGAGAGCTTGCTCTTTT
AACTTAGTGGCGGACGGGTGAGTAACGCGTGAGTAACCTGCCTTTCAGAG
GGGAATAACATTCTGAAAAGAATGCTAATACCGCATGAGATCGTAGTATC
GCATGGTACAGCGACCAAAGGAGCAATCCGCTGAAAGATGGACTCGCGTC
CGATTAGCTAGTTGGTGAGATAAAGGCCCACCAAGGCGACGATCGGTAGC
CGGACTGAGAGGTTGAACGGCCACATTGGGACTGAGACACGGCCCAGACT
CCTACGGGAGGCAGCAGTGGGGGATATTGCACAATGGGGGAAACCCTGAT
GCAGCAACGCCGCGTGAAGGAAGAAGGTCTTCGGATTGTAAACTTCGTC
CTCAGGGAAGATAATGACGGTACCTGAGGAGGAAGCTCCGGCTAACTACG
TGCCAGCAGCCGCGGTAATACGTAGGGAGCAAGCGTTGTCCGGATTTACT
GGGTGTAAAGGGTGCGTAGGCGGATCTGCAAGTCAGTAGTGAAATCCCAG
GGCTTAACCCTGGAACTGCTATTGAAACTGTGGGTCTTGAGTGAGGTAGA
GGCAGGCGGAATTCCCGGTGTAGCGGTGAAATGCGTAGAGATCGGGAGGA
ACACCAGTGGCGAAGGCGGCCTGCTGGGCCTTAACTGACGCTGAGGCACG
AAAGCATGGGTAGCAAACAGGATTAGATACCCTGGTAGTCCATGCCGTAA
ACGATGATTACTAGGTGTGGGTGGTCTGACCCCATCCGTGCCGGAGTTAA
CACAATAAGTAATCCACCTGGGGAGTACGACCGCAAGGTTGAAACTCAAA
GGAATTGACGGGGGCCCGCACAAGCAGTGGAGTATGTGGTTTAATTCGAA
GCAACGCGAAGAACCTTACCAGGTCTTGACATCCTGCTAACGAGGTAGAG
ATACGTTAGGTGCCCTTCGGGGAAAGCAGAGACAGGTGGTGCATGGTTGT
CGTCAGCTCGTGTCGTGAGATGTTGGGTTAAGTCCCGCAACGAGCGCAAC
CCCTGCTATTAGTTGCTACGCAAGAGCACTCTAATAGGACTGCCGTTGAC
AAAACGGAGGAAGGTGGGGACGACGTCAAATCATCATGCCCCTTATGACC
TGGGCTACACACGTACTACAATGGCCGTCAACAGAGAGAAGCAAAGCCGC
GAGGTGGAGCAAAACTCTAAAACGGTCCCAGTTCGGATCGTAGGCTGCA
ACCCGCCTACGTGAAGTTGGAATTGCTAGTAATCGCGGATCATCATGCCG
CGGTGAATACGTTCCCGGGCCTTGTACACACCGCCCGTCACACCATGGGA
GCCGGTAATACCCGAAGTCAGTAGTCTAACCGCAAGGGGACGCGCCGAAA
GGTGGAGTG

TABLE 10

>2D9 (SEQ ID NO.: 9)

CTGGCGGGTGCTACCATGCAGTCGAGCGAAGCACTTTTGCGGATTTCTTC
GGATTGAAGCAATTGTGACTGAGCGGCGGACGGGTGAGTAACGCGTGGGT
AACCTGCCTCATACAGGGGGATAACAGTTGGAAACGGCTGCTAATACCGC
ATAAGCGCACAGTACCGCATGGTACCGTGTGAAAAACTCCGGTGGTATGA
GATGGACCCGCGTCTGATTAGCTAGTTGGTGGGGTAACGGCCTACCAAGG
CGACGATCAGTAGCCGACCTGAGAGGGTGAACCGGCCACATTGGGACTGAG
ACACGGCCCAAACTCCTACGGGAGGCAGCAGTGGGGAATATTGCACAATG
GGGGAAACCCTGATGCAGCGACGCCGCGTGAGCGATGAAGTATTTCGGTA
TGTAAAGCTCTATCAGCAGGGAAGAAAATGACGGTACCTGCTGACTAAGAAG
CCCGGCTAACTACGTGCCAGCAGCCGCGGTAATACGTAGGGGGCAAGCGT
TATCCGGATTTACTGGGTGTAAAGGGAGCGTAGACGGCATGGCAAGCCAG
ATGTGAAAGCCCGGGGCTCAACCCCGGGACTGCATTTGGAACTGTCAGGC
TAGAGTGTCGGAGAGGAAAGCGGAATTCCTAGTGTAGCGGTGAAATGCGT
AGATATTAGGAGGAACACCAGTGGCGAAGGCGGCTTTCTGGACGATGACT
GACGTTGAGGCTCGAAAGCGTGGGGAGCAAACAGGATTAGATACCCTGGT
AGTCCACGCCGTAAACGATGAATACTAGGTGTCGGGTGGCAAAGCCATTC
GGTGCCGCAGCAAACGCAATAAGTATTCCACCTGGGGAGTACGTTCGCAA
GAATGAAACTCAAAGGAATTGACGGGGACCCGCACAAGCGGTGGAGCATG
TGGTTTAATTGGAAGCAACGCGAAGAACCTTACCTGGTCTTGACATCCCT
CTGACCGCTCTTTAATCGGAGTTTCTTTCGGGACAGAGGAGACAGGTGG
TGCATGGTTGTCGTCAGCTCGTGTCGTGAGATGTTGGGTTAAGTCCCGCA
ACGAGCGCAACCCCTATCTTTAGTAGCCAGCATTTAGGGTGGGCACTCTA
GAGAGACTGCCAGGGATAACCTGGAGGAAGGTGGGGATGACGTCAAATCA
TCATGCCCCTTATGACCAGGGCTACACACGTGCTACAATGGCGTAAACAA
AGGGAGCGACCCGCGAGGGGGAGCCAATCCCAAAAATAACGTCTACGT
TCGGATTGTAGTCTGCAACTCGACTACATGAAGCTGGAATCGCTAGTAAT
CGCGAATCAGAATGTCGCGGTGAATACGTTCCCGGGTCTTGTACACACCG
CCCGTCACACCATGGGAGTCAGTAACGCCCGAAGTCAGTGACCCAACCGT
AAGGAGGAGCTGCCGAAGTGTACTAT

TABLE 11

>2F7 (SEQ ID NO.: 10)

GAGTGGGCCGCTACCATGCAGTCGACGAGCCGAGGGGAGCTTGCTCCCCA
GAGCTAGTGGCGGACGGGTGAGTAACACGTGAGCAACCTGCCTTTCAGAG
GGGGATAACGTTTGGAAACGAACGCTAATACCGCATAACATACCGGGACC
GCATGATTCTGGTATCAAAGGAGCAATCCGCTGAAAGATGGGCTCGCGTC
CGATTAGCTAGTTGGCGGGGTAACGGCCCACCAAGGCGACGATCGGTAGC
CGGACTGAGAGGTTGATCGGCCACATTGGGACTGAGACACGCCCAGACT
CCTACGGGAGGCAGCAGTGGGGGATATTGCACAATGGAGGAAACTCTGAT
GCAGCGACGCCGCGTGAGGGAAGACGGTCTTCGGATTGTAAACCTCTGTC
TTTGGGGACGATAATGACGGTACCCAAGGAGGAAGCTCCGGCTAACTACG
TGCCAGCAGCCGCGGTAATACGTAGGGAGCGAGCGTTGTCCGGAATTACT
GGGTGTAAAGGGAGCGTAGGCGGGGTCTCAAGTCGAATGTTAAATCTACC
GGCTCAACTGGTAGCTGCGTTCGAAACTGGGGCTCTTGAGTGAAGTAGAG
GCAGGCGGAATTCCTAGTGTAGCGGTGAAATGCGTAGATATTAGGAGGAA
CACCAGTGGCGAAGGCGGCCTGCTGGCTTTTACTGACGCTGAGGCTCGA
AAGCGTGGGGAGCAAACAGGATTAGATACCCTGGTAGTCCACGCCGTAAA
CGATGATTACTAGGTGTGGGGGACTGACCCCTTCCGTGCCGGAGTTAAC
ACAATAAGTAATCCACCTGGGAGTACGACCGCAAGGTTGAAACTCAAAG
GAATTGACGGGGGCCCGCACAAGCAGTGGATTATGTGGTTTAATTCGAAG
CAACGCGAAGAACCTTACCAGGTCTTGACATCGGACGGCTCTAGAGA
TAGAGCTTTCCTTCGGGACACAAAGACAGGTGGTGCATGGTTGTCGTCAG
CTCGTGTCGTGAGATGTTGGGTTAAGTCCCGCAACGAGCGCAACCCTTAT
TATTAGTTGCTACATTCAGTTGAGCACTCTAATGAGACTGCCGTTGACAA
AACGGAGGAAGGTGGGGATGACGTCAAATCATCATGCCCCTTATGACCTG
GGCTACACACGTAATACAATGGCGATCAACAGAGGGAAGCAAGACCGCGA
GGTGGAGCAAAACCCCTAAAAGTCGTCTCAGTTCGGATTGCAGGCTGCAAC
TCGCCTGCATGAAGTCGGAATTGCTAGTAATCGCGGATCAGCATGCCGCG
GTGAATACGTTCCCGGGCCTTGTACACACCGCCCGTCACACCATGGGAGT
CGGTAACACCCGAAGTCAGTAGCCTAACCGCAAAGAGGGCGCTGCCGAAG
ATGGATT

TABLE 12

>1D1 (SEQ ID NO.: 11)

ATGGCGGCTGCTACCTGCAGTCGAACGGGGTTATTTTGGAAATCTCTTCG
GAGATGGAATTCTTAACCTAGTGGCGGACGGGTGAGTAACGCGTGAGGAA
TCTGCCTTTAGGAGGGGGATAACAGTCGGAAACGGCTGCTAATACCGCAT
AATACGTTTGGAGGCATCTCTTGAACGTCAAAGATTTTATCGCCTTTAG
ATGAGCTCGCGTCTGATTAGCTGGTTGGCGGGGTAACGGCCCACCAAGGC
GACGATCAGTAGCCGGACTGAGAGGTTGAACGGCCACATTGGGACTGAGA
CACGGCCCAGACTCCTACGGGAGGCAGCAGTGGGGAATATTGCGCAATGG
GGGAAACCCTGACGCAGCAACGCCGCGTGATTGAAGAAGGCCTTCGGGTT
GTAAAGATCTTTAATCAGGGACGAAAAATGACGGTACCTGAAGAATAAGC
TCCGGCTAACTACGTGCCAGCAGCCGCGGTAATACGTAGGGAGCAAGCGT
TATCCGGATTTACTGGGTGTAAAGGGCGCGCAGGCGGGCCGCAAGTTGG
GAGTGAAATCCCGGGGCTTAACCCCGGAACTGCTTTCAAAACTGCTGGTC
TTGAGTGATGGAGAGGCAGGCGGAATTCCGTGTGTAGCGGTGAAATGCGT
AGATATACGGAGGAACACCAGTGGCGAAGGCGGCCTGCTGGACATTAACT
GACGCTGAGGCGCGAAAGCGTGGGGAGCAAACAGGATTAGATACCCCTGG
AGTCCACGCCGTAAACGATGGATACTAGGTGTGGGAGGTATTGACCCCTT
CCGTGCCGCAGTTAACACAATAAGTATCCCACCTGGGGAGTACGGCCGCA
AGGTTGAAACTCAAAGGAATTGACGGGGGCCCGCACAAGCAGTGGAGTAT
GTGGTTTAATTCGAAGCAACGCGAAGAACCTTACCAGGTCTTGACATCCC
GATGACCGGCGTAGAGATACGCCCTCTCTTCGGAGCATCGGTGACAGGTG
GTGCATGGTTGTCGTCAGCTCGTGTCGTGAGATGTTGGGTTAAGTCCCGC
AACGAGCGCAACCCTTACGGTTAGTTGATACGCAAGATCACTCTAGCCGG
ACTGCCGTTGACAAAACGGAGGAAGGTGGGGATGACGTCAAATCATCATG
CCCCTTATGACCTGGGCTACACACGTACTACAATGGCAGTCATACAGAGG
GAAGCAATACCGCGAGGTGGAGCAAATCCCTAAAAGCTGTCCCAGTTCAG
ATTGCAGGCTGCAACCCGCCTGCATGAAGTCGGAATTGCTAGTAATCGCG
GATCACATGCCGCGGTGAATACGTTCCCGGGCCTTGTACACACCGCCCG
TCACACCATGAGAGCCGTCAATACCCGAAGTCCGTAGCCTAACCGCAAGG
GGGCGCGCCGAAGTTACGT

TABLE 13

>1F8 (SEQ ID NO.: 12)

ATCGGGTGCTACCTGCAAGTCGAGCGAAGCGGTTTCGATGAAGTTTTCGG
ATGGAATTGAAATTGACTTAGCGGCGGACGGGTGAGTAACGCGTGGGTAA
CCTGCCTTACACTGGGGGATAACAGTTAGAAATGACTGCTAATACCGCAT
AAGCGCACAGGGCCGCATGGTCTGGTGCGAAAAACTCCGGTGGTGTAAGA
TGGACCCGCGTCTGATTAGGTAGTTGGTGGGGTAACGGCCCACCAAGCCG

TABLE 13-continued

>1F8 (SEQ ID NO.: 12)

ACGATCAGTAGCCGACCTGAGAGGGTGACCGGCCACATTGGGACTGAGAC
ACGGCCCAAACTCCTACGGGAGGCAGCAGTGGGGAATATTGGACAATGGG
CGAAAGCCTGATCCAGCGACGCCGCGTGAGTGAAGAAGTATTTCGGTATG
TAAAGCTCTATCAGCAGGGAAGAAAATGACGGTACCTGACTAAGAAGCCC
CGGCTAACTACGTGCCAGCAGCCGCGGTAATACGTAGGGGGCAAGCGTTA
TCCGGATTTACTGGGTGTAAAGGGAGCGTAGACGGTTAAGCAAGTCTGAA
GTGAAAGCCCGGGGCTCAACCCCGGTACTGCTTTGGAAACTGTTTGACTT
GAGTGCAGGAGAGGTAAGTGGAATTCCTAGTGTAGCGGTGAAATGCGTAG
ATATTAGGAGGAACACCAGTGGCGAAGGCGGCTTACTGGACTGTAACTGA
CGTTGAGGCTCGAAAGCGTGGGGAGCAAACAGGATTAGATACCCTGGTAG
TCCACGCCGTAAACGATGAATACTAGGTGTCGGGGGACAACGTCCTTCGG
TGCCGCCGCTAACGCAATAAGTATTCCACCTGGGGAGTACGTTCGCAAGA
ATGAAACTCAAAGGAATTGACGGGACCCGCACAAGCGGTGGAGCATGTG
GTTTAATTCGAAGCAACGCGAAGAACCTTACCAAGTCTTGACATCCCATT
GAAAATCCTTTAACCGTGGTCCCTCTTCGGAGCAATGAGACAGGTGGTG
CATGGTTGTCGTCAGCTCGTGTCGTGAGATGTTGGGTTAAGTCCCGCAAC
GAGCGCAACCCTTATCCTTAGTAGCCAGCACATGATGGTGGGCACTCTGG
GGAGACTGCCAGGGATAACCTGGAGGAAGGTGGGGATGACGTCAAATCAT
CATGCCCCTTATGATTTGGGCTACACACGTGCTACAATGGCGTAAACAAA
GGGAAGCAAAGGAGCGATCTGGAGCAAACCCCAAAAATAACGTCTCAGTT
CGGATTGCAGGCTGCAACTCGCCTGCATGAAGCTGGAATCGCTAGTAATC
GCGAATCAGAATGTCGCGGTGAATACGTTCCCGGGTCTTGTACACACCGC
CCGTCACACCATGGGAGTTGGTAACGCCCGAAGTCAGTGACCCAACCGTA
AGGAGGAGCGCCGAAGGCGAGGT

TABLE 14

>1C2 (SEQ ID NO.: 13)

CGGGGCTGCTTAAATGCAGTCGAACGGGATCCATCAAGCTTGCTTGGTGG
TGAGAGTGGCGAACGGGTGAGTAATGCGTGACCGACCTGCCCCATGCACC
GGATAGCTCCTGGAAACGGGTGGTAATGCCGGATACCTCCATCACACTGC
ATGGTGTGTTGGGAAAGCCTTTGCGGCATGGGATGGGGTCGCGTCCTATC
AGCTTGATGGCGGGGTAACGGCCCACCATGGCTTCGACGGGTAGCCGGCC
TGAGAGGGCGACCGGCCACATTGGGACTGAGATACGGCCCAGACTCCTAC
GGGAGGCAGCAGTGGGGAATATTGCACAATGGGCGCAAGCCTGATCGTGC
GACGCCGCGTGAGGGATGGAGGCCTTCGGGTTGTAAACCTCTTTTGTTAG
GGAGCAAGGCATTTTGTGTTGAGTGTACCTTTCGAATAAGCACCGGCTAA
CTACGTGCCAGCAGCCGCGGTAATACGTAGGGTGCAAGCGTTATCCGGAA
TTATTGGGCGTAAAGGGCTCGTAGGCGGTTCGTCGCGTCCGGTGTGAAAG
TCCATCGCTTAACGGTGGATCCGCGCGGGTACGGGCAGGCTTGAGTGCG
GTAGGGGAGACTGGAATTCCCGGTGTAACGGTGGAATGTGTAGATATCGG
GAAGAACACCAATGGCGAAGGCAGGTCTCTGGGCCGTTACTGACGCTGAG
GAGCGAAAGCGTGGGGAGCGAACAGGATTAGATACCCTGGTAGTCCACGC
CGTAAACGGTGGATGCTGGATGTGGGGCCCGTTCCACGGGTTCCGTGTCG
GAGCTAACGCGTTAAGCATCCCGCCTGGGGATGTACGGCCGCAAGGCTAAA
ACTCAAAGAAATTGACGGGGGCCCGCACAAGCGGCGGAGCATGCGGATTA
ATTCGATGCAACGCGAAGAACCTTACCTGGGCTTGACATGTTCCCGACGA
TCCCAGAGATGGGGTTTCCCTTCGGGCGGGTTCACAGGTGGTGCATGGT
CGTCGTCAGCTCGTGTCGTGAGATGTTGGGTTAAGTCCCGCAACGAGCGC
AACCCTCGCCCCGTGTTGCCAGCGGATTGTGCCGGGAACTCACGGGGAC
CGCCGGGGTTAACTCGGAGGAAGGTGGGGATGACGTCAGATCATCATGCC
CCTTACGTCCAGGGCTTCACGCATGCTACAATGGCCGGATCAAACGGGATG
CGACAGCGCGAGCTGGAGCGGATCCCTGAAAACCGGTCTCAGTTCGGATC
GCAGTCTGCAACTCGACTGCGTGAAGGCGAGTCGCTAGTAATCGCGAAT
CAGCAACGTCGCGGTGAATGCGTTCCCGGGCCTTGTACACACCGCCCGTC
AAGTCATGAAAGTGGGCAGCACCCGAAGCCGGTGGCCTAACCCCTTGCGG
GAGGGAGCCGTCTAAGGTAGGTT

TABLE 15

>1D4 (SEQ ID NO.: 14)

CGGGCGCTGCTTACCTGCAGTCGAGCGAAGCACTTGAGCGGATTTCTTCG
GATTGAAGTTTTTTGACTGAGCGGCGGACGGGTGAGTAACGCGTGGGTA
ACCTGCCTCATACAGGGGGATAACAGTTAGAAATGACTGCTAATACCGCA
TAAGCGCACAGGACCGCATGGTCTGGTGTGAAAAACTCCGGTGGTATGAG
ATGGACCCGCGTCTGATTAGCTAGTTGGAGGGGTAACGGCCCACCAAGGC
GACGATCAGTAGCCGACCTGAGAGGGTGACCGGCCACATTGGGACTGAGA
CACGGCCCAGACTCCTACGAGGCAGCAGTGGGGAATATTGCACAATGG
GGGAAACCCTGATGCAGCGACGCCGCGTGAAGGAAGAAGTATCTCGGTAT
GTAAACTTCTATCAGCAGGGAAGAAAATGACGGTACCTGACTAAGAAGCC
CCGGCTAACTACGTGCCAGCAGCCGCGGTAATACGTAGGGGGCAAGCGTT

TABLE 15-continued

>1D4 (SEQ ID NO.: 14)

ATCCGGATTTACTGGGTGTAAAGGGAGCGTAGACGGAAGAGCAAGTCTGA
TGTGAAAGGCTGGGGCTTAACCCCAGGACTGCATTGGAAACTGTTTTTCT
AGAGTGCCGGAGAGGTAAGCGGAATTCCTAGTGTAGCGGTGAAATGCGTA
GATATTAGGAGGAACACCAGTGGCGAAGGCGGCTTACTGGACGGTAACTG
ACGTTGAGGCTCGAAAGCGTGGGGAGCAAACAGGATTAGATACCCTGGTA
GTCCACGCCGTAAACGATGAATACTAGGTGTCGGGTGCAAAGCCATTCG
GTGCCGCAGCAAACGCAATAAGTATTCCACCTGGGGAGTACGTTCGCAAG
AATGAAACTCAAAGGAATTGACGGGACCCGCACAAGCGGTGGAGCATGT
GGTTTAATTCGAAGCAACGCGAAGAACCTTACCAAGTCTTGACATCCCTC
TGACCGGCCCGTAACGGGGCCTTCCCTTCGGGGCAGAGGAGACAGGTGGT
GCATGGTTGTCGTCAGCTCGTGTCGTGAGATGTTGGGTTAAGTCCCGCAA
CGAGCGCAACCCCTATCCTTAGTAGCCAGCAGGTGAAGCTGGGCACTCTA
GGGAGACTGCCGGGGATAACCGGAGGAAGGCGGGGACGACGTCAAATCA
TCATGCCCCTTATGATTTGGGCTACACACGTGCTACAATGGCGTAAACAA
AGGGAAGCGAGACAGCGATGTTGAGCAAATCCCAAAAATAACGTCCCAGT
TCGGACTGCAGTCTGCAACTCGACTGCACGAAGCTGGAATCGCTAGTAAT
CGCGAATCAGAATGTCGCGGTGAATACGTTCCCGGGTCTTGTACACACCG
CCCGTCACACCATGGGAGTCAGTAACGCCCGAAGTCAGTGACCCAACCTT
ATAGGAGGAGCGCCGAAGTCGACCT

TABLE 16

>1E3 (SEQ ID NO.: 15)

CGCGGGTGCTATACTGCAGTCGAACGCACTGATTTTATCAGTGAGTGGCG
AACGGGTGAGTAATACATAAGTAACCTGCCCTCATGAGGGGATAACTAT
TAGAAATGATAGCTAAGACCGCATAGGTGAAGGGGTCGCATGACCGCTTC
ATTAAATATCCGTATGGATAGCAGGAGGATGGACTTATGGCGCATTAGCT
GGTTGGTGAGGTAACGGCTCACCAAGGCGACGATGCGTAGCCGACCTGAG
AGGGTGGACGGCCACACTGGGACTGAGACACGGCCCAGACTCCTACGGGA
GGCAGCAGTAGGGAATTTTCGGCAATGGGGGAAACCCTGACCGAGCAACG
CCGCGTGAGGGAAGAAGTATTTCGGTATGTAAACTTCTGTTATAAAGGAA
GAACGTATGAATAGGAAATGATTCATAAGTGACGGTACTTTATGAGAAA
GCCACGGCTAACTACGTGCCAGCAGCCGCGGTAATACGTAGGTGGCGAGC
GTTATCCGGAATCATTGGGCGTAAAGAGGGAGCAGGCGGCAATAGAGGTC
TGCGGTGAAAGCCTGGAAGCTAAACTTCAGTAAGCCGTGGAAACCAAATAG
CTAGAGTGCAGTAGAGGATCGTGGAATTCCATGTGTAGCGGTGAAATGCG
TAGATATATGGAGGAACACCAGTGGCGAAGGCGACGATCTGGGCTGCAAC
TGACGCTCAGTCCCGAAAGCGTGGGGAGCAAATAGGATTAGATACCCTAG
TAGTCCACGCCGTAAACGGATGAGTACTAAGTGTTGGGGGGCTCAAACCTCAG
TGCTGCAGTTAACGCAATAAGTACTCCGCCTGAGTAGTACGTTCGCAAGA
ATGAAACTCAAAGGAATTGACGGGGCCCGCACAAGCGGTGGAGCATGTG
GTTTAATTCGAAGCAACGCGAAGAACCTTACCAGGTCTTGACATACCTCT
AAAGGCTCTAGAGATAGAGAGATAGCTATAGGGGATACAGGTGGTGCATG
GTTGTCGTCAGCTCGTGTCGTGAGATGTTGGGTTAAGTCCCGCAACGAGC
GCAACCCTTGTCGCTAGTTACCATCATTAAGTTGGGGACTCTAGCGAGAC
TGCCTCTGCAAGGAGGAGGAAGGCGGGGATGACGTCAAATCATCATGCCC
CTTATGACCTGGGCTACACACGTGCTACAATGGACGGATCAAAGGGAAGC
GAAGCCGCGAGGTGGAGCGAAACCCAAAAACCCGTTCTCAGTTCGGACTG
CAGTCTGCAACTCGACTGCAGAAGTTGGAATCGCTAGTAATCGCGAATC
AGAATGTCGCGGTGAATACGTTCTCGGGCCTTGTACACACCGCCCGTCAC
ACCATGAGAGTTGGTAACACCCGAAGCCGGTGGCTTAACCGCAAGGAGAG
AGCTTCTAAGGTGAAT

TABLE 17

>1A9 (SEQ ID NO.: 16)

AGGCGCGTGCTACCATGCAGTCGAACGAAGCAATTTAACGGAAGTTTTCG
GATGGAAGTTGAATTGACTGAGTGGCGACGGGTGAGTAACGCGTGGGTA
ACCTGCCTTGTACTGGGGGACAACAGTTAGAAATGACTGCTAATACCGCA
TAAGCGCACAGTATCGCATGATACAGTGTGAAAAACTCCGGTGGTACAAG
ATGGACCCGCGTCTGATTAGCTAGTTGGTAAGGTAACGGCTTACCAAGGC
GACGATCAGTAGCCGACCTGAGAGGGTGACCGGCCACATTGGGACTGAGA
CACGGCCCAAACTCCTACGGAGGCAGCAGTGGGGAATATTGCACAATGG
GCGAAAGCCTGATGCAGCGACGCCGCGTGAGTGAAGAAGTATTTCGGTAT
GTAAAGCTCTATCAGCAGGGAAGAAAATGACGGTACCTGACTAAGAAGCC
CCGGCTAACTACGTGCCAGCAGCCGCGGTAATACGTAGGGGGCAAGCGTT
ATCCGGATTTACTGGGTGTAAAGGGAGCGTAGACGGTAAAGCAAGTCTGA
AGTGAAAGCCCGCGGCTCAACTGCGGGACTGCTTTGGAAACTGTTTAACT
GGAGTGTCGGAGAGGTAAGTGGAATTCCTAGTGTAGCGGTGAAATGCGTA
GATATTAGGAGGAACACCAGTGGCGAAGGCGACTTACTGGACGATAACTG
ACGTTGAGGCTCGAAAGCGTGGGGAGCAAACAGGATTAGATACCCTGGTA

TABLE 17-continued

>1A9 (SEQ ID NO.: 16)

GTCCACGCCGTAAACGATGAATACTAGGTGTTGGGGAGCAAAGCTCTTCG
GTGCCGTCGCAAACGCAGTAAGTATTCCACCTGGGGAGTACGTTCGCAAG
AATGAAACTCAAAGGAATTGACGGGGACCCGCACAAGCGGTGGAGCATGT
GGTTTAATTCGAAGCAACGCGAAGAACCTTACCAGGTCTTGACATCGATC
CGACGGGGGAGTAACGTCCCCTTCCCTTCGGGGCGGAGAAGACAGGTGGT
GCATGGTTGTCGTCAGCTCGTGTCGTGAGATGTTGGGTTAAGTCCCGCAA
CGAGCGCAACCCTTATTCTAAGTAGCCAGCGGTTCGGCCGGGAACTCTTG
GGAGACTGCCAGGGATAACCTGGAGGAAGGTGGGGATGACGTCAAATCAT
CATGCCCCTTATGATCTGGGCTACACACGTGCTACAATGGCGTAAACAAA
GAGAAGCAAGACCGCGAGGTGGAGCAAATCTCAAAAATAACGTCTCAGTT
CGGACTGCAGGCTGCAACTCGCCTGCACGAAGCTGGAATCGCTAGTAATC
GCGAATCAGAATGTCGCGGTGAATACGTTCCCGGGTCTTGTACACACCGC
CGTCACACCATGGGAGTCAGTAACGCCCGAAGTCAGTGACCCAACCGCA
AGGAGGAGCGCCGAAGGCGACCGT

TABLE 18

>2G11 (SEQ ID NO.: 17)

CGGTCTCGGCTTACCATGCAGTCGAGGGGCAGCATGGTCTTAGCTTGCTA
AGGCTGATGGCGACCGGCGCACGGGTGAGTAACACGTATCCAACCTGCCG
TCTACTCTTGGCCAGCCTTCTGAAAGGAAGATTAATCAGGATGGCATCA
TGAGTTCACATGTCCGCATGATTAAAGGTATTTTCCGGTAGACGATGGGG
ATGCGTTCCATTAGATAGTAGGCGGGGTAACGGCCCACCTAGTCAACGAT
GGATAGGGGTTCTGAGAGGAAGGTCCCCCACATTGGAACTGAGACACGGT
CCAAACTCCTACGGGAGGCAGCAGTGAGGAATATTGGTCAATGGGCGATG
GCCTGAACCAGCCAAGTAGCGTGAAGGATGACTGCCCTATGGGTTGTAAA
CTTCTTTTATAAAGGAATAAAGTCGGGTATGCATACCCGTTTGCATGTAC
TTTATGAATAAGGATCGGCTAACTCCGTGCCAGCAGCCGCGGTAATACGG
AGGATCCGAGCGTTATCCGGATTTATTGGGTTTAAAGGGAGCGTAGATGG
ATGTTTAAGTCAGTTGTGAAAGTTTGCGGCTCAACCGTAAAATTGCAGTT
GATACTGGATGTCTTGAGTGCAGTTGAGGCAGGCGGAATTCGTGGTGTAG
CGGTGAAATGCTTAGATATCACGAAGAACTCCGATTGCGAAGGCAGCCTG
CTAAGCTGCAACTGACATTGAGGCTCGAAAGTGTGGGTATCAAACAGGAT
TAGATACCCTGGTAGTCCACACGGTAAACGATGAATACTCGCTGTTTGCG
ATATACGGCAAGCGGCCAAGCGAAAGCGTTAAGTATTCCACCTGGGGAGT
ACGCCGGCAACGGTGAAACTCAAAGGAATTGACGGGGCCCGCACAAGCG
GAGGAACATGTGGTTTAATTCGATGATACGCGAGGAACCTTACCCGGCT
TAAATTGCACTCGAATGATCCGGAAACGGTTCAGCTAGCAATAGCGAGTG
TGAAGGTGCTGCATGGTTGTCGTCAGCTCGTGCCGTGAGGTGTCGGCTTA
AGTGCCATAACGAGCGCAACCCTTGTTGTCAGTTACTAACAGGTGATGCT
GAGGACTCTGACAAGACTGCCATCGTAAGATGTGAGGAAGGTGGGGATGA
CGTCAAATCACGGCCCTTACGTCCGGGGCTACACAGTGTTACAATG
GGGGGTACAGAGGGCCGCTACCACGCGAGTGGATGCCAATCCCTAAAACC
CCTCTCAGTTCGGACTGGAGTCTGCAACCCGACTCCACGAAGCTGGATTC
GCTAGTAATCGCGCATCAGCCACGGCGGTGAATACGTTCCCGGGCCTT
GTACACACCGCCCGTCAAGCCATGGGAGCCGGGGGTACCTGAAGTGCGTA
ACCGCGAGGATCGCCCTAGGTAATGA

TABLE 19

>2E1 (SEQ ID NO.: 18)

CGGCGGCTGCTTACCATGCAGTCGAACGAAGCATTTAGGATTGAAGTTTT
CGGATGGATTTCCTATATGACTGAGTGGCGGACGGGTGAGTAACGCGTGG
GAACCTGCCCTATACAGGGGGATAACAGCTGGAAACGGCTGCTAATACC
GCATAAGCGCACAGAATCGCATGATTCAGTGTGAAAAGCCCTGGCAGTAT
AGGATGGTCCCGCGTCTGATTAGCTAGTTGGTGGTGGGTAACGGCTCACCAA
GGCGACGATCAGTAGCCGGCCTGAGAGAGTGAACGGCCACATTGGGACTG
AGACACGGCCCAAACTCCTACGGGAGGCAGCAGTGGGGAATATTGCACAA
TGGGGGAAACCCTGATGCAGCGACGCCGCGTGAGTGAAGAAGTATTTCGG
TATGTAAAGCTCTATCAGCAGGGAAGAAAATGACGGTACCTGACTAAGA
AGCCCCGGCTAACTACGTGCCAGCAGCCGCGGTAATACGTAGGGGCAAG
CGTTATCCGGAATTACTGGGTGTAAAGGGTGCGTAGGTGGCATGGTAAGT
CAGAAGTGAAAGCCCGGGGCTTAACCCCGGGACTGCTTTTGAAACTGTCA
TGCTGGAGTGCAGGAGAGGTAAGCGGAATTCCTAGTGTAGCGGTGAAATG
CGTAGATATTAGGAGGAACACCAGTGGCGAAGGCGGCTTACTGGACTGTC
ACTGACACTGATGCACGAAAGCGTGGGGAGCAAACAGGATTAGATACCCT
GGTAGTCCACGCCGTAAACGATGAATACTAGGTGTCGGGGCCGTAGAGGC
TTCGGTGCCGCAGCAAACGCAGTAAGTATTCCACCTGGGGAGTACGTTCG
CAAGAATGAAACTCAAAGGAATTGACGGGGACCCGCACAAGCGGTGGAGC
ATGTGGTTTAATTCGAAGCAACGCGAAGAACCTTACCTGGTCTTGACATC

TABLE 19-continued

>2E1 (SEQ ID NO.: 18)

CCAATGACCGAACCTTAACCGGTTTTTTCTTCGAGACATTGGAGACAGG
TGGTGCATGGTTGTCGTCAGCTCGTGTCGTGAGATGTTGGGTTAAGTCCC
GCAACGAGCGCAACCCCTATCTTTAGTAGCCAGCATTTAAGGTGGGCACT
CTAGAGAGACTGCCAGGGATAACCTGGAGGAAGGTGGGGACGACGTCAAA
TCATCATGCCCCTTATGGCCAGGGCTACACACGTGCTACAATGGCGTAAA
CAAAGGGAAGCGAAGTCGTGAGGCGAAGCAAATCCCAGAAATAACGTCTC
AGTTCGGATTGTAGTCTGCAACTCGACTACATGAAGCTGGAATCGCTAGT
AATCGTGAATCAGAATGTCACGGTGAATACGTTCCCGGGTCTTGTACACA
CCGCCCGTCACACCATGGGAGTCAGTAACGCCCGAAGTCAGTGACCCAAC
CGCAAGGAGGGAGCTGCCGAAGTACGAG

TABLE 20

>1F7 (SEQ ID NO.: 19)

TTTGTGGCGAAGCCTGATGCAGCGACGCCGCGTGAGTGAAGAAGTATTTC
GGTATGTAAAGCTCTATCAGCAGGGAAGAAAATGACGGTACCTGACTAAG
AAGCCCCGGCTAACTACGTGCCAGCAGCCGCGGTAATACGTAGGGGGCAA
GCGTTATCCGGATTTACTGGGTGTAAAGGGAGCGTAGACGGCGAAGCAAG
TCTGAAGTGAAAACCCAGGGCTCAACCCTGGGACTGCTTTGGAAACTGTT
TTGCTAGAGTGTCGGAGAGGTAAGTGGAATTCCTAGTGTAGCGGTGAAAT
GCGTAGATATTAGGAGGAACACCAGTGGCGAAGGCGGCTTACTGGACAGT
AACTGACGTTGAGGCTCGAAAGCGTGGGGAGCAAACAGGATTAGATACCC
TGGTAGTCCACGCCGTAAACGATGAATGCTAGGTGTTGGGGGGCAAAGCC
CTTCGGTGCCGTCGCAAACGCAGTAAGCATTCCACCTGGGGAGTACGTTC
GCAAGAATGAAACTCAAAGGAATTGACGGGGACCCGCACAAGCGGTGGAG
CATGTGGTTTAATTCGAAGCAACGCGAAGAACCTTACCAAGTCTTGACAT
CCTCTTGACCGGCGTGTAACGGCGCCTTCCCTTCGGGGCAAGAGACAG
GTGGTGCATGGTTGTCGTCAGCTCGTGTCGTGAGATGTTGGGTTAAGTCC
CGCAACGAGCGCAACCCTTATCCTTAGTAGCCAGCAGGTAAGCTGGGCAC
CTCTAGGGAGACTGCCAGGGATAACCTGGAGGAAGGTGGGGATGACGTCA
AATCATCATGCCCCTTATGATTTGGGCTACACACGTGCTACAATGGCGTA
AACAAAGGGAAGCAAGACAGTGATGTGGAGCAAATCCCAAAAATAACGTC
CCAGTTCGGACTGTAGTCTGCAACCCGACTACACGAAGCTGGAATCGCTA
GTAATCGCGAATCAGAATGTCGCGGTGAATACGTTCCCGGGTCTTGTACA
CACCGCCCGTCACACCATGGGAGTCAGCAACGCCCGAAGTCAGTGACCCA
ACTCGCAAGAGAGGGAGCGCCGAAGTCGTCAT

TABLE 21

>1D2 (SEQ ID NO.: 20)

CTGGCGCGGCTACCATGCAGTCGAGCGAAGCATTACAGCGGAAGTTTTCG
GATGGAAGCTTTAATGACTGAGCGGCGGACGGGTGAGTAACGCGTGGATA
ACCTGCCTCATACAGGGGGATAACAGTTAGAAATGACTGCTAATACCGCA
TAAGCGCACAGATCGCATGATCACGTGTGAAAAACTCCGGTGGTATGA
ATGGATCCGCGTCTGATTAGTTAGTTGGCGGGGTAAAGGCCCACCAAGAC
GACGATCAGTAGCCGGCCTGAGAGGGTGAACGGCCACATTGGGACTGAGA
CACGGCCCAAACTCCTACGGGAGGCAGCAGTGGGGAATATTGCACAATGG
GGGAAACCCTGATGCAGCGACGCCGCGTGAGTGAAGAAGTATTTCGGTAT
GTAAAGCTCTATCAGCAGGGAAGAAAATGACGGTACCTGACTAAGAAGCC
CCGGCTAACTACGTGCCAGCAGCCGCGGTAATACGTAGGGGGCAAGCGTT
ATCCGGATTTACTGGGTGTAAAGGAGCGTAGACGGCAATGCAAGTCTGG
AGTGAAAACCCAGGGCTCAACCCTGGGAGTGCTTTGGAAACTGTATAGCT
AGAGTGCTGGAGAGGTAAGTGGAATTCCTAGTGTAGCGGTGAAATGCGTA
GATATTAGGAGGAACACCAGTGGCGAAGGCGGCTTACTGGACAGTAACTG
ACGTTGAGGCTCGAAAGCGTGGGGAGCAAACAGGATTAGATACCCTGGTA
GTCCACGCCGTAAACGATGAATGCTAGGTGTTGGGGGCAAAGCCCTTCG
GTGCCGTCGCAAACGCAATAAGCATTCCACCTGGGGAGTACGTTCAAG
AATGAAACTCAAAGGAATTGACGGGACCCGCACAAGCGGTGGAGCATGT
GGTTTAATTCGAAGCAACGCGAAGAACCTTACCAAGTCTTGACATCCTCC
TGACCGGTCCGTAACGGGGCCTTCCCTTCGGGACAAGAGACAGGTGGT
GCATGGTTGTCGTCAGCTCGTGTCGTGAGATGTTGGGTTAAGTCCCGCAA
CGAGCGCAACCCTTATCCTTAGTAGCCAGCAGGTAGAGCTGGGCACTCTA
GGGAGACTGCCAGGGATAACCTGGAGGAAGGTGGGGATGACGTCAAATCA
TCATGCCCCTTATGATTTGGGCTACACACGTGCTACAATGGCGTAAACAA
AGGGAAGCGACCCTGCGAGGCAAGCAAATCCCAAAAATAACGTCCAGT
TCGGTAGTCTGCAACCCGACTACACGAAGCTGGAATCGCTAGTAAT
CGCGAATCAGAATGTCGCGGTGAATACGTTCCCGGGTCTTGTACACACCG
CCCGTCACACCATGGGAGTCAGCAACGCCCGAAGTCAGTGACCCAACTGC
AGGAGAGGGAGCGCCGAAGTCGGGCT

The invention claimed is:

1. A composition that induces proliferation and/or accumulation of Th17 cells, the composition comprising, as an active component three or more bacteria selected from the group consisting of: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* and *Bifidobacterium breve*; and one or more enteric polymers.

2. A composition that induces proliferation and/or accumulation of Th17 cells, the composition comprising, as an active component: (a) three or more bacteria that contain DNA comprising a nucleotide sequence that has at least 97% homology with a DNA sequence designated herein as SEQ ID Nos. 1-20, or (b) three or more bacteria that contain DNA comprising a nucleotide sequence that has at least 97% homology with DNA of the following bacteria: *Clostridium symbiosum, Clostridium hathewayi, Clostridium citroniae, Clostridium bolteae, Ruminococcus* sp. M-1, *Ruminococcus gnavus, Blautia* sp. canine oral taxon 143, *Anaerostipes caccae, Clostridium lactatifermentans, Coprobacillus cateniformis, Clostridium ramosum,* cf. *Clostridium* sp. MLG055, *Clostridium innocuum, Eubacterium desmolans, Clostridium orbiscindens, Ruminococcus* sp. 16442, *Anaerotruncus colihominis, Bacteroides dorei, Bifidobacterium pseudolongum* subsp. *Pseudolongum,* or *Bifidobacterium breve*; and one or more enteric polymers.

3. The composition according to claim 1, wherein the Th17 cells are transcription factor RORgammat-positive Th17 cells or IL-17 producing Th17 cells.

4. The composition according to claim 1, wherein the composition promotes a protective immune response.

5. A pharmaceutical composition comprising the composition according to claim 1 and a pharmaceutically acceptable component.

6. A vaccine composition comprising the composition according to claim 1 and at least one antigen, and a pharmaceutically acceptable component.

7. The composition according to claim 1, wherein the bacteria are human-derived bacteria.

8. The pharmaceutical composition according to claim 5, wherein the pharmaceutical composition is formulated for delivery to the colon.

9. The composition according to claim 2, wherein the Th17 cells are transcription factor RORgammat-positive Th17 cells or IL-17 producing Th17 cells.

10. The composition according to claim 2, wherein the composition promotes a protective immune response.

11. A pharmaceutical composition comprising the composition according to claim 2 and a pharmaceutically acceptable component.

12. A vaccine composition comprising the composition according to claim 2, at least one antigen, and a pharmaceutically acceptable component.

13. The composition according to claim 2, wherein the bacteria are human-derived bacteria.

14. The pharmaceutical composition according to claim 11, wherein the pharmaceutical composition is formulated for delivery to the colon.

* * * * *

SEQUENCE LISTING

<160> NUMBER OF SEQ ID NOS: 26

<210> SEQ ID NO 1
<211> LENGTH: 1419
<212> TYPE: DNA
<213> ORGANISM: Clostridium ramosum

<400> SEQUENCE: 1

| | | | | | |
|---|---|---|---|---|---|
| ggggcggctg | ctataatgca | gtcgacgcga | gcacttgtgc | tcgagtggcg | aacgggtgag | 60 |
| taatacataa | gtaacctgcc | ctagacaggg | ggataactat | tggaaacgat | agctaagacc | 120 |
| gcatatgtac | ggacactgca | tggtgaccgt | attaaaagtg | cctcaaagca | ctggtagagg | 180 |
| atggacttat | ggcgcattag | ctggttggcg | gggtaacggc | ccaccaaggc | gacgatgcgt | 240 |
| agccgacctg | agagggtgac | cggccacact | gggactgaga | cacggcccag | actcctacgg | 300 |
| gaggcagcag | tagggaattt | tcggcaatgg | gggaaaccct | gaccgagcaa | cgccgcgtga | 360 |
| aggaagaagg | ttttcggatt | gtaaacttct | gttataaagg | aagaacggcg | gctacaggaa | 420 |
| atggtagccg | agtgacggta | ctttattaga | aagccacggc | taactacgtg | ccagcagccg | 480 |
| cggtaatacg | taggtggcaa | gcgttatccg | gaattattgg | gcgtaaagag | ggagcaggcg | 540 |
| gcagcaaggg | tctgtggtga | aagcctgaag | cttaacttca | gtaagccata | gaaaccaggc | 600 |
| agctagagtg | caggagagga | tcgtggaatt | ccatgtgtag | cggtgaaatg | cgtagatata | 660 |
| tggaggaaca | ccagtggcga | aggcgacgat | ctggcctgca | actgacgctc | agtcccgaaa | 720 |
| gcgtggggag | caaataggat | tagataccct | agtagtccac | gccgtaaacg | atgagtacta | 780 |
| agtgttggat | gtcaaagttc | agtgctgcag | ttaacgcaat | aagtactccg | cctgagtagt | 840 |
| acgttcgcaa | gaatgaaact | caaaggaatt | gacgggggcc | cgcacaagcg | gtggagcatg | 900 |
| tggtttaatt | cgaagcaacg | cgaagaacct | taccaggtct | tgacatactc | ataaaggctc | 960 |
| cagagatgga | gagatagcta | tatgagatac | aggtggtgca | tggttgtcgt | cagctcgtgt | 1020 |
| cgtgagatgt | tgggttaagt | cccgcaacga | gcgcaaccct | tatcgttagt | taccatcatt | 1080 |
| aagttgggga | ctctagcgag | actgccagtg | acaagctgga | ggaaggcggg | gatgacgtca | 1140 |
| aatcatcatg | ccccttatga | cctgggctac | acacgtgcta | caatggatgg | tgcagaggga | 1200 |
| agcgaagccg | cgaggtgaag | caaaacccat | aaaaccattc | tcagttcgga | ttgtagtctg | 1260 |
| caactcgact | acatgaagtt | ggaatcgcta | gtaatcgcga | atcagcatgt | cgcggtgaat | 1320 |
| acgttctcgg | gccttgtaca | caccgcccgt | cacaccacga | gagttgataa | cacccgaagc | 1380 |
| cggtggccta | accgcaagga | aggagcttct | aaggtggat | | | 1419 |

<210> SEQ ID NO 2
<211> LENGTH: 1433
<212> TYPE: DNA
<213> ORGANISM: Bifidobacterium pseudolongum subsp. Pseudolongum

<400> SEQUENCE: 2

| | | | | | |
|---|---|---|---|---|---|
| ctgcggcgtc | taccatgcag | tcgaacggga | tccctggcag | cttgctgccg | gggtgagagt | 60 |
| ggcgaacggg | tgagtaatgc | gtgaccgacc | tgccccatgc | accggaatag | ctcctggaaa | 120 |
| cgggtggtaa | tgccggatgt | tccacatgag | cgcatgcgag | tgtgggaaag | gcttttttgcg | 180 |
| gcatgggatg | gggtcgcgtc | ctatcagctt | gttggtgggg | taacggccta | ccaaggcgtt | 240 |
| gacgggtagc | cggcctgaga | gggcgaccgg | ccacattggg | actgagatac | ggcccagact | 300 |
| cctacgggag | gcagcagtgg | ggaatattgc | acaatgggcg | caagcctgat | gcagcgacgc | 360 |
| cgcgtgcggg | atggaggcct | tcgggttgta | aaccgctttt | gttcaagggc | aaggcacggt | 420 |

```
ctttggccgt gttgagtgga ttgttcgaat aagcaccggc taactacgtg ccagcagccg      480
cggtaatacg tagggtgcaa gcgttatccg gatttattgg gcgtaaaggg ctcgtaggcg      540
gttcgtcgcg tccggtgtga aagtccatcg cttaacggtg gatccgcgcc gggtacgggc      600
gggcttgagt gcggtagggg agactggaat tcccggtgta acggtggaat gtgtagatat      660 cggaagaac accaatggcg aaggcaggtc tctgggccgt tactgacgct gaggagcgaa       720
agcgtgggga gcgaacagga ttagataccc tggtagtcca cgccgtaaac ggtggatgct      780
ggatgtgggg ccctttttcc gggtcctgtg tcggagctaa cgcgttaagc atcccgcctg      840
gggagtacgg ccgcaaggct aaaactcaaa gaaattgacg ggggcccgca caagcggcgg      900
agcatgcgga ttaattcgat gcaacgcgaa gaaccttacc tgggcttgac atgtgccgga      960
cgcccgcgga gacgcgggtt ccttcgggg ccggttcaca ggtggtgcat ggtcgtcgtc      1020
agctcgtgtc gtgagatgtt gggttaagtc ccgcaacgag cgcaaccctc gccgcgtgtt     1080
gccagcgggt catgccggga actcacgtgg gaccgccggg gttaactcgg aggaaggtgg     1140
ggatgacgtc agatcatcat gccccttacg tccagggctt cacgcatgct acaatggccg     1200
gtacaacggg gtgcgacacg tgacgtgggg cggatccct gaaaaccggt ctcagttcgg      1260
atcgcagtct gcaactcgac tgcgtgaagg tggagtcgct agtaatcgcg gatcagcaac     1320
gccgcggtga atgcgttccc gggccttgta cacaccgccc gtcaagtcat gaaagtgggc     1380
agcacccgaa gacggtggcc taaccttgt gggggagcc gtctaaggta gtg              1433
```

<210> SEQ ID NO 3
<211> LENGTH: 1428
<212> TYPE: DNA
<213> ORGANISM: Clostridium lactatifermentans

<400> SEQUENCE: 3

```
ctgccggctc taccatgcag tcgaacgaag atagttagaa tgagagcttc ggcaggattt       60
ttttctatct tagtggcgga cgggtgagta acgtgtgggc aacctgccct gtactgggga     120
ataatcattg gaaacgatga ctaataccgc atgtggtcct cggaaggcat cttctgagga     180
agaaaggatt tattcggtac aggatgggcc cgcatctgat tagctagttg gtgagataac      240
agcccaccaa ggcgacgatc agtagccgac ctgagagggt gatcggccac attgggactg     300
agacacggcc caaactccta cgggaggcag cagtggggaa tattgcacaa tgggcgaaag     360
cctgatgcag caacgccgcg tgaaggatga agggtttcgg ctcgtaaact tctatcaata      420
gggaagaaac aaatgacggt acctaaataa gaagccccgg ctaactacgt gccagcagcc      480
gcggtaatac gtagggggca agcgttatcc ggaattactg ggtgtaaagg gagcgtaggc      540
ggcatggtaa gccagatgtg aaagccttgg gcttaacccg aggattgcat ttggaactat      600
caagctagag tacaggagag gaaagcggaa ttcctagtgt agcggtgaaa tgcgtagata      660
ttaggaagaa caccagtggc gaaggcggct ttctggactg aaactgacgc tgaggctcga      720
aagcgtgggg agcaaacagg attagatacc ctggtagtcc acgccgtaaa cgatgagtgc      780
taggtgtcgg ggaggaatcc tcggtgccga agctaacgca ataagcactc cacctgggga     840
gtacgaccgc aaggttgaaa ctcaaaggaa ttgacggggg cccgcacaag cggtggagca     900
tgtggtttaa ttcgaagcaa cgcgaagaac cttaccaagg cttgacatcc cgatgaccgt      960
cctagagata ggacttctct tcggagcatc ggtgacaggt ggtgcatggt tgtcgtcagc    1020
tcgtgtcgtg agatgttggg ttaagtcccg caacgagcgc aacccttatc ttcagtagcc     1080
```

| atcattcagt tgggcactct ggagagactg ccgtggataa cacggaggaa ggtggggatg | 1140 |
| acgtcaaatc atcatgcccc ttatgtcttg ggctacacac gtgctacaat ggctggtaac | 1200 |
| aaagtgacgc gagacggcga cgttaagcaa atcacaaaaa cccagtccca gttcggattg | 1260 |
| tagtctgcaa ctcgactaca tgaagctgga atcgctagta atcgcgaatc agcatgtcgc | 1320 |
| ggtgaatacg ttcccgggcc ttgtacacac cgcccgtcac accatgggag ttggaagcac | 1380 |
| ccgaagtcgg tgacctaacc gtaaggaaga gccgccgaag tagggggat | 1428 |

<210> SEQ ID NO 4
<211> LENGTH: 1422
<212> TYPE: DNA
<213> ORGANISM: Blautia sp. canine oral taxon 143

<400> SEQUENCE: 4

| cggcgctcta ccatgcagtc gacgaagcga tttgaatgaa gttttcggat ggattttaaa | 60 |
| ttgactgagt ggcggacggg tgagtaacgc gtgggtaacc tgccccatac aggggggataa | 120 |
| cagttagaaa tgactgctaa taccgcataa gaccacagcg ccgcatggtg caggggtaaa | 180 |
| aactccggtg gtatgggatg gacccgcgtc tgattagctt gttggcgggg taacggccca | 240 |
| ccaaggcgac gatcagtagc cgacctgaga gggtgaccgg ccacattggg actgagacac | 300 |
| ggcccaaact cctacgggag gcagcagtgg ggaatattgc acaatggggg aaaccctgat | 360 |
| gcagcgacgc cgcgtgagtg atgaagtatt tcggtatgta aagctctatc agcagggaag | 420 |
| aaaatgacgg tacctgacta agaagccccg gctaactacg tgccagcagc cgcggtaata | 480 |
| cgtaggggggc aagcgttatc cggatttact gggtgtaaag ggagcgtaga cggctgtgca | 540 |
| agtctggagt gaaagcccgg ggctcaaccc cgggactgct ttggaaactg tacggctgga | 600 |
| gtgctggaga ggcaagcgga attcctagtg tagcggtgaa atgcgtagat attaggagga | 660 |
| acaccagtgg cgaaggcggc ttgctggaca gtaactgacg ttgaggctcg aaagcgtggg | 720 |
| gagcaaacag gattagatac cctggtagtc cacgccgtaa acgatgaatg ctaggtgtcg | 780 |
| gggagcaaag ctcttcggtg ccgccgcaaa cgcaataagc attccacctg ggagtacgt | 840 |
| tcgcaagaat gaaactcaaa ggaattgacg gggacccgca caagcggtgg agcatgtggt | 900 |
| ttaattcgaa gcaacgcgaa gaaccttacc aagtcttgac atccccctga ccggcaagta | 960 |
| atgtcgcctt tccttcggga caggggagac aggtggtgca tggttgtcgt cagctcgtgt | 1020 |
| cgtgagatgt tgggttaagt cccgcaacga gcgcaaccct tatcctcagt agccagcagg | 1080 |
| tgaagctggg cactctgtgg agactgccag ggataacctg gaggaaggtg gggacgacgt | 1140 |
| caaatcatca tgccccttat gacttgggct acacacgtgc tacaatggcg taaacaaagg | 1200 |
| gaagcgagag ggtgacctgg agcaaatccc aaaaataacg tctcagttcg gattgtagtc | 1260 |
| tgcaactcga ctacatgaag ctggaatcgc tagtaatcgc gaatcagcat gtcgcggtga | 1320 |
| atacgttccc gggtcttgta cacaccgccc gtcacaccat gggagtcagc aacgcccgaa | 1380 |
| gccggtgacc taaccgcaag gaaggagccg tcgaagtcgt cg | 1422 |

<210> SEQ ID NO 5
<211> LENGTH: 1425
<212> TYPE: DNA
<213> ORGANISM: cf. Clostridium sp. MLG055

<400> SEQUENCE: 5

| cggcgctgct atactgcagt cgaacgaagc gaaggtagct tgctatcgga gcttagtggc | 60 |
| gaacgggtga gtaacacgta gataacctgc ctgtatgacc gggataacag ttggaaacga | 120 |

```
ctgctaatac cggataggca gagaggaggc atctcttctc tgttaaagtt gggatacaac        180
gcaaacagat ggatctgcgg tgcattagct agttggtgag gtaacggccc accaaggcga        240
tgatgcatag ccggcctgag agggcgaacg gccacattgg gactgagaca cggcccaaac        300
tcctacggga ggcagcagta gggaattttc ggcaatgggg gaaaccctga ccgagcaatg        360
ccgcgtgagt gaagacggcc ttcgggttgt aaagctctgt tgtaagggaa gaacggcata        420
gagagggaat gctctatgag tgacggtacc ttaccagaaa gccacggcta actacgtgcc        480
agcagccgcg gtaatacgta ggtggcaagc gttatccgga attattgggc gtaaagggtg        540
cgtaggcggt tggataagtc tgaggtaaaa gcccgtggct caaccacggt aagccttgga        600
aactgtctgg ctggagtgca ggagaggaca tggaattcca tgtgtagcg gtaaaatgcg         660 tagatatatg gaggaacacc agtggcgaag gcggttgtct ggcctgtaac tgacgctgaa        720
gcacgaaagc gtgggagca ataggatta gataccctag tagtccacgc cgtaaacgat          780
gagaactaag tgttggggaa actcagtgct gcagttaacg caataagttc tccgcctggg        840
gagtatgcac gcaagtgtga aactcaaagg aattgacggg ggcccgcaca gcggtggag        900 tatgtggttt aattcgacgc aacgcgaaga accttaccag gccttgacat ggtatcaaag        960
gccctagaga tagggagata ggtatgatac acacaggtgg tgcatggttg tcgtcagctc        1020
gtgtcgtgag atgttgggtt aagtcccgca acgagcgcaa cccttgtttc tagttaccaa       1080
cagtaagatg gggactctag agagactgcc ggtgacaaac cggaggaagg tggggatgac        1140
gtcaaatcat catgcccctt atggcctggg ctacacacgt actacaatgg cgtctacaaa        1200
gagcagcgag caggtgactg taagcgaatc tcataaagga cgtctcagtt cggattgaag        1260
tctgcaactc gacttcatga agtcggaatc gctagtaatc gcggatcagc atgccgcggt        1320
gaatacgttc tcgggccttg tacacaccgc ccgtcaaacc atgggagttg ataatacccg        1380
aagccggtgg cctaaccgaa aggagggagc cgtcgaagta gattg                       1425
```

<210> SEQ ID NO 6
<211> LENGTH: 1431
<212> TYPE: DNA
<213> ORGANISM: Clostridium innocuum

<400> SEQUENCE: 6

```
cggcgctgct ataatgcagt cgaacgaagt ttcgaggaag cttgcttcca aagagactta         60
gtggcgaacg ggtgagtaac acgtaggtaa cctgcccatg tgtccgggat aactgctgga        120
aacggtagct aaaaccggat aggtatacag agcgcatgct cagtatatta aagcgcccat        180
caaggcgtga acatggatgg acctgcggcg cattagctag ttggtgaggt aacggcccac        240
caaggcgatg atgcgtagcc ggcctgagag ggtaaacggc cacattggga ctgagacacg        300
gcccaaactc ctacgggagg cagcagtagg gaattttcgt caatggggga aaccctgaac        360
gagcaatgcc gcgtgagtga agaaggtctt cggatcgtaa agctctgttg taagtgaaga        420
acggctcata gaggaaatgc tatgggagtg acggtagctt accagaaagc cacggctaac        480
tacgtgccag cagccgcggt aatacgtagg tggcaagcgt tatccggaat cattgggcgt        540
aaagggtgcg taggtggcgt actaagtctg tagtaaaagg caatggctca accattgtaa        600
gctatggaaa ctggtatgct ggagtgcaga agagggcgat ggaattccat gtgtagcggt        660
aaaatgcgta gatatatgga ggaacaccag tggcgaaggc ggtcgcctgg tctgtaactg        720
acactgaggc acgaaagcgt ggggagcaaa taggattaga taccctagta gtccacgccg        780
```

| | |
|---|---|
| taaacgatga gaactaagtg ttggaggaat tcagtgctgc agttaacgca ataagttctc | 840 |
| cgcctgggga gtatgcacgc aagtgtgaaa ctcaaaggaa ttgacggggg cccgcacaag | 900 |
| cggtggagta tgtggtttaa ttcgaagcaa cgcgaagaac cttaccaggc cttgacatgg | 960 |
| atgcaaatgc cctagagata gagagataat tatggatcac acaggtggtg catggttgtc | 1020 |
| gtcagctcgt gtcgtgagat gttgggttaa gtcccgcaac gagcgcaacc cttgtcgcat | 1080 |
| gttaccagca tcaagttggg gactcatgcg agactgccgg tgacaaaccg gaggaaggtg | 1140 |
| gggatgacgt caaatcatca tgccccttat ggcctgggct acacacgtac tacaatggcg | 1200 |
| accacaaaga gcagcgacac agtgatgtga agcgaatctc ataaaggtcg tctcagttcg | 1260 |
| gattgaagtc tgcaactcga cttcatgaag tcggaatcgc tagtaatcgc agatcagcat | 1320 |
| gctgcggtga atacgttctc gggccttgta cacaccgccc gtcaaaccat gggagtcagt | 1380 |
| aatacccgaa gccggtggca taaccgtaag gaggagccgt cgaagtgact g | 1431 |

<210> SEQ ID NO 7
<211> LENGTH: 1428
<212> TYPE: DNA
<213> ORGANISM: Clostridium orbiscindens

<400> SEQUENCE: 7

| | |
|---|---|
| agggcggctc ttaaatgcag tcgaacgggg tgctcatgac ggaggattcg tccaacggat | 60 |
| tgagttacct agtggcggac gggtgagtaa cgcgtgagga acctgccttg gagagggaa | 120 |
| taacactccg aaaggagtgc taataccgca tgatgcagtt gggtcgcatg gctctgactg | 180 |
| ccaaagattt atcgctctga gatggcctcg cgtctgatta gctagtaggc ggggtaacgg | 240 |
| cccacctagg cgacgatcag tagccggact gagaggttga ccggccacat tgggactgag | 300 |
| acacggccca gactcctacg ggaggcagca gtggggaata ttgggcaatg ggcgcaagcc | 360 |
| tgacccagca acgccgcgtg aaggaagaag ctttcgggt tgtaaacttc ttttgtcggg | 420 |
| gacgaaacaa atgacggtac ccgacgaata agccacggct aactacgtgc cagcagccgc | 480 |
| ggtaatacgt aggtggcaag cgttatccgg atttactggg tgtaaagggc gtgtaggcgg | 540 |
| gattgcaagt cagatgtgaa aactgggggc tcaacctcca gcctgcattt gaaactgtag | 600 |
| ttcttgagtg ctggagaggc aatcggaatt ccgtgtgtag cggtgaaatg cgtagatata | 660 |
| cggaggaaca ccagtggcga aggcggattg ctggacagta actgacgctg aggcgcgaaa | 720 |
| gcgtggggag caaacaggat tagataccct ggtagtccac gccgtaaacg atggatacta | 780 |
| ggtgtggggg gtctgacccc ctccgtgccg cagttaacac aataagtatc ccacctgggg | 840 |
| agtacgatcg caaggttgaa actcaaagga attgacgggg cccgcacaa gcggtggagt | 900 |
| atgtggttta attcgaagca acgcgaagaa ccttaccagg cttgacatc ccactaacga | 960 |
| ggcagagatg cgttaggtgc ccttcgggga aagtggagac aggtggtgca tggttgtcgt | 1020 |
| cagctcgtgt cgtgagatgt tgggttaagt cccgcaacga gcgcaaccct tattgttagt | 1080 |
| tgctacgcaa gagcactcta gcgagactgc cgttgacaaa acgaggaag gtggggacga | 1140 |
| cgtcaaatca tcatgcccct tatgtcctgg gccacacacg tactacaatg gtggttaaca | 1200 |
| gagggaggca ataccgcgag gtggagcaaa tccctaaaag ccatcccagt tcggattgca | 1260 |
| ggctgaaacc cgcctgtatg aagttggaat cgctagtaat cgcggatcag catgccgcgg | 1320 |
| tgaatacgtt cccgggcctt gtacacaccg cccgtcacac catgagagtc gggaacaccc | 1380 |
| gaagtccgta gcctaaccgc aaggagggcg cggccgaaag ttgttcat | 1428 |

<210> SEQ ID NO 8
<211> LENGTH: 1409
<212> TYPE: DNA
<213> ORGANISM: Ruminococcus sp. 16442

<400> SEQUENCE: 8

| | | | | | |
|---|---|---|---|---|---|
| cgggggctgc | taccatgcag | tcgaacggag | ttaagagagc | ttgctctttt | aacttagtgg | 60 |
| cggacgggtg | agtaacgcgt | gagtaacctg | cctttcagag | gggaataaca | ttctgaaaag | 120 |
| aatgctaata | ccgcatgaga | tcgtagtatc | gcatggtaca | cgaccaaag | gagcaatccg | 180 |
| ctgaaagatg | gactcgcgtc | cgattagcta | gttggtgaga | taaaggccca | ccaaggcgac | 240 |
| gatcggtagc | cggactgaga | ggttgaacgg | ccacattggg | actgagacac | ggcccagact | 300 |
| cctacgggag | gcagcagtgg | gggatattgc | acaatggggg | aaaccctgat | gcagcaacgc | 360 |
| cgcgtgaagg | aagaaggtct | tcggattgta | aacttctgtc | ctcagggaag | ataatgacgg | 420 |
| tacctgagga | ggaagctccg | gctaactacg | tgccagcagc | cgcggtaata | cgtagggagc | 480 |
| aagcgttgtc | cggatttact | gggtgtaaag | ggtgcgtagg | cggatctgca | agtcagtagt | 540 |
| gaaatcccag | ggcttaaccc | tggaactgct | attgaaactg | tgggtcttga | gtgaggtaga | 600 |
| ggcaggcgga | attcccggtg | tagcggtgaa | atgcgtagag | atcggagga | acaccagtgg | 660 |
| cgaaggcggc | ctgctgggcc | ttaactgacg | ctgaggcacg | aaagcatggg | tagcaaacag | 720 |
| gattagatac | cctggtagtc | catgccgtaa | acgatgatta | ctaggtgtgg | gtggtctgac | 780 |
| cccatccgtg | ccggagttaa | cacaataagt | aatccacctg | gggagtacgg | ccgcaaggtt | 840 |
| gaaactcaaa | ggaattgacg | ggggcccgca | caagcagtgg | agtatgtggt | ttaattcgaa | 900 |
| gcaacgcgaa | gaaccttacc | aggtcttgac | atcctgctaa | cgaggtagag | atacgttagg | 960 |
| tgcccttcgg | ggaaagcaga | gacaggtggt | gcatggttgt | cgtcagctcg | tgtcgtgaga | 1020 |
| tgttgggtta | agtcccgcaa | cgagcgcaac | ccctgctatt | agttgctacg | caagagcact | 1080 |
| ctaataggac | tgccgttgac | aaaacggagg | aaggtgggga | cgacgtcaaa | tcatcatgcc | 1140 |
| ccttatgacc | tgggctacac | acgtactaca | atggccgtca | acagagagaa | gcaaagccgc | 1200 |
| gaggtggagc | aaaactctaa | aaacggtccc | agttcggatc | gtaggctgca | acccgcctac | 1260 |
| gtgaagttgg | aattgctagt | aatcgcggat | catcatgccg | cggtgaatac | gttcccgggc | 1320 |
| cttgtacaca | ccgcccgtca | caccatggga | gccggtaata | cccgaagtca | gtagtctaac | 1380 |
| cgcaagggga | cgcgccgaaa | ggtggagtg | | | | 1409 |

<210> SEQ ID NO 9
<211> LENGTH: 1426
<212> TYPE: DNA
<213> ORGANISM: Ruminococcus gnavus

<400> SEQUENCE: 9

| | | | | | |
|---|---|---|---|---|---|
| ctggcgggtg | ctaccatgca | gtcgagcgaa | gcacttttgc | ggatttcttc | ggattgaagc | 60 |
| aattgtgact | gagcggcgga | cgggtgagta | acgcgtgggt | aacctgcctc | atacaggggg | 120 |
| ataacagttg | gaaacggctg | ctaataccgc | ataagcgcac | agtaccgcat | ggtaccgtgt | 180 |
| gaaaaactcc | ggtggtatga | gatggacccg | cgtctgatta | gctagttggt | ggggtaacgg | 240 |
| cctaccaagg | cgacgatcag | tagccgacct | gagagggtga | ccggccacat | tgggactgag | 300 |
| acacggccca | aactcctacg | ggaggcagca | gtggggaata | ttgcacaatg | ggggaaaccc | 360 |
| tgatgcagcg | acgccgcgtg | agcgatgaag | tatttcggta | tgtaaagctc | tatcagcagg | 420 |
| gaagaaaatg | acggtacctg | actaagaagc | cccggctaac | tacgtgccag | cagccgcggt | 480 |

| | |
|---|---|
| aatacgtagg gggcaagcgt tatccggatt tactgggtgt aaagggagcg tagacggcat | 540 |
| ggcaagccag atgtgaaagc ccggggctca accccgggac tgcatttgga actgtcaggc | 600 |
| tagagtgtcg gagaggaaag cggaattcct agtgtagcgg tgaaatgcgt agatattagg | 660 |
| aggaacacca gtggcgaagg cggctttctg gacgatgact gacgttgagg ctcgaaagcg | 720 |
| tggggagcaa acaggattag ataccctggt agtccacgcc gtaaacgatg aatactaggt | 780 |
| gtcgggtggc aaagccattc ggtgccgcag caaacgcaat aagtattcca cctgggagt | 840 |
| acgttcgcaa gaatgaaact caaaggaatt gacggggacc cgcacaagcg gtggagcatg | 900 |
| tggtttaatt ggaagcaacg cgaagaacct tacctggtct tgacatccct ctgaccgctc | 960 |
| tttaatcgga gttttctttc gggacagagg agacaggtgg tgcatggttg tcgtcagctc | 1020 |
| gtgtcgtgag atgttgggtt aagtcccgca acgagcgcaa cccctatctt tagtagccag | 1080 |
| catttagggt gggcactcta gagagactgc cagggataac ctggaggaag gtggggatga | 1140 |
| cgtcaaatca tcatgcccct tatgaccagg gctacacacg tgctacaatg gcgtaaacaa | 1200 |
| agggaagcga gcccgcgagg gggagcaaat cccaaaaata acgtctcagt tcggattgta | 1260 |
| gtctgcaact cgactacatg aagctggaat cgctagtaat cgcgaatcag aatgtcgcgg | 1320 |
| tgaatacgtt cccgggtctt gtacacaccg cccgtcacac catgggagtc agtaacgccc | 1380 |
| gaagtcagtg acccaaccgt aaggaggagc tgccgaagtg tactat | 1426 |

<210> SEQ ID NO 10
<211> LENGTH: 1407
<212> TYPE: DNA
<213> ORGANISM: Anaerotruncus colihominis

<400> SEQUENCE: 10

| | |
|---|---|
| gagtgggccg ctaccatgca gtcgacgagc cgagggagc ttgctcccca gagctagtgg | 60 |
| cggacgggtg agtaacacgt gagcaacctg cctttcagag ggggataacg tttggaaacg | 120 |
| aacgctaata ccgcataaca taccgggacc gcatgattct ggtatcaaag gagcaatccg | 180 |
| ctgaaagatg ggctcgcgtc cgattagcta gttggcgggg taacggccca ccaaggcgac | 240 |
| gatcggtagc cggactgaga ggttgatcgg ccacattggg actgagacac ggcccagact | 300 |
| cctacgggag gcagcagtgg gggatattgc acaatggagg aaactctgat gcagcgacgc | 360 |
| cgcgtgaggg aagacggtct tcggattgta aacctctgtc tttggggacg ataatgacgg | 420 |
| tacccaagga ggaagctccg gctaactacg tgccagcagc cgcggtaata cgtagggagc | 480 |
| gagcgttgtc cggaattact gggtgtaaag ggagcgtagg cggggtctca gtcgaatgt | 540 |
| taaatctacc ggctcaactg gtagctgcgt tcgaaactgg ggctcttgag tgaagtagag | 600 |
| gcaggcggaa ttcctagtgt agcggtgaaa tgcgtagata ttaggaggaa caccagtggc | 660 |
| gaaggcggcc tgctgggctt ttactgacgc tgaggctcga aagcgtgggg agcaaacagg | 720 |
| attagatacc ctggtagtcc acgccgtaaa cgatgattac taggtgtggg gggactgacc | 780 |
| ccttccgtgc cggagttaac acaataagta atccacctgg ggagtacgac cgcaaggttg | 840 |
| aaactcaaag gaattgacgg gggcccgcac aagcagtgga ttatgtggtt taattcgaag | 900 |
| caacgcgaag aaccttacca ggtcttgaca tcgagtgacg gctctagaga tagagctttc | 960 |
| cttcgggaca caaagacagg tggtgcatgg ttgtcgtcag ctcgtgtcgt gagatgttgg | 1020 |
| gttaagtccc gcaacgagcg caacccttat tattagttgc tacattcagt tgagcactct | 1080 |
| aatgagactg ccgttgacaa aacgaggaa ggtggggatg acgtcaaatc atcatgcccc | 1140 |
| ttatgacctg ggctacacac gtaatacaat ggcgatcaac agagggaagc aagaccgcga | 1200 |

-continued

| | |
|---|---|
| ggtggagcaa acccctaaaa gtcgtctcag ttcggattgc aggctgcaac tcgcctgcat | 1260 |
| gaagtcggaa ttgctagtaa tcgcggatca gcatgccgcg gtgaatacgt tcccgggcct | 1320 |
| tgtacacacc gcccgtcaca ccatgggagt cggtaacacc cgaagtcagt agcctaaccg | 1380 |
| caaagagggc gctgccgaag atggatt | 1407 |

<210> SEQ ID NO 11
<211> LENGTH: 1419
<212> TYPE: DNA
<213> ORGANISM: Eubacterium desmolans

<400> SEQUENCE: 11

| | |
|---|---|
| atggcggctg ctacctgcag tcgaacgggg ttattttgga aatctcttcg gagatggaat | 60 |
| tcttaaccta gtggcggacg ggtgagtaac gcgtgagcaa tctgccttta ggaggggat | 120 |
| aacagtcgga aacggctgct aataccgcat aatacgtttg ggaggcatct cttgaacgtc | 180 |
| aaagatttta tcgcctttag atgagctcgc gtctgattag ctggttggcg ggtaacggc | 240 |
| ccaccaaggc gacgatcagt agccggactg agaggttgaa cggccacatt gggactgaga | 300 |
| cacggcccag actcctacgg gaggcagcag tggggaatat tgcgcaatgg gggaaaccct | 360 |
| gacgcagcaa cgccgcgtga ttgaagaagg ccttcgggtt gtaaagatct ttaatcaggg | 420 |
| acgaaaaatg acggtacctg aagaataagc tccggctaac tacgtgccag cagccgcggt | 480 |
| aatacgtagg gagcaagcgt tatccggatt tactgggtgt aaagggcgcg caggcgggcc | 540 |
| ggcaagttgg gagtgaaatc ccggggctta accccgaac tgctttcaaa actgctggtc | 600 |
| ttgagtgatg gagaggcagg cggaattccg tgtgtagcgg tgaaatgcgt agatatacgg | 660 |
| aggaacacca gtggcgaagg cggcctgctg gacattaact gacgctgagg cgcgaaagcg | 720 |
| tggggagcaa acaggattag ataccctggt agtccacgcc gtaaacgatg gatactaggt | 780 |
| gtgggaggta ttgaccccctt ccgtgccgca gttaacacaa taagtatccc acctggggag | 840 |
| tacggccgca aggttgaaac tcaaaggaat tgacggggc ccgcacaagc agtggagtat | 900 |
| gtggtttaat tcgaagcaac gcgaagaacc ttaccaggtc ttgacatccc gatgaccggc | 960 |
| gtagagatac gccctctctt cggagcatcg gtgacaggtg gtgcatggtt gtcgtcagct | 1020 |
| cgtgtcgtga gatgttgggt taagtcccgc aacgagcgca acccttacgg ttagttgata | 1080 |
| cgcaagatca ctctagccgg actgccgttg acaaaacgga ggaaggtggg gacgacgtca | 1140 |
| aatcatcatg ccccttatga cctgggctac acacgtacta caatggcagt catacagagg | 1200 |
| gaagcaatac cgcgaggtgg agcaaatccc taaaagctgt cccagttcag attgcaggct | 1260 |
| gcaacccgcc tgcatgaagt cggaattgct agtaatcgcg gatcagcatg ccgcggtgaa | 1320 |
| tacgttcccg ggccttgtac acaccgcccg tcacaccatg agagccgtca atacccgaag | 1380 |
| tccgtagcct aaccgcaagg gggcgcgccg aagttacgt | 1419 |

<210> SEQ ID NO 12
<211> LENGTH: 1423
<212> TYPE: DNA
<213> ORGANISM: Clostridium hathewayi

<400> SEQUENCE: 12

| | |
|---|---|
| atcgggtgct acctgcaagt cgagcgaagc ggtttcgatg aagttttcgg atggaattga | 60 |
| aattgactta gcggcggacg ggtgagtaac gcgtgggtaa cctgccttac actgggggat | 120 |
| aacagttaga aatgactgct aataccgcat aagcgcacag ggccgcatgg tctggtgcga | 180 |

```
aaaactccgg tggtgtaaga tggacccgcg tctgattagg tagttggtgg ggtaacggcc     240
caccaagccg acgatcagta gccgacctga gagggtgacc ggccacattg ggactgagac     300
acggcccaaa ctcctacggg aggcagcagt ggggaatatt ggacaatggg cgaaagcctg     360
atccagcgac gccgcgtgag tgaagaagta tttcggtatg taaagctcta tcagcaggga     420
agaaaatgac ggtacctgac taagaagccc cggctaacta cgtgccagca gccgcggtaa     480
tacgtagggg gcaagcgtta ccggatttta ctgggtgtaa agggagcgta gacggttaag     540
caagtctgaa gtgaaagccc ggggctcaac cccggtactg ctttggaaac tgtttgactt     600
gagtgcagga gaggtaagtg gaattcctag tgtagcggtg aaatgcgtag atattaggag     660
gaacaccagt ggcgaaggcg gcttactgga ctgtaactga cgttgaggct cgaaagcgtg     720
gggagcaaac aggattagat accctggtag tccacgccgt aaacgatgaa tactaggtgt     780
cgggggacaa cgtccttcgg tgccgccgct aacgcaataa gtattccacc tggggagtac     840
gttcgcaaga atgaaactca aaggaattga cggggacccg cacaagcggt ggagcatgtg     900
gtttaattcg aagcaacgcg aagaaccttac ccaagtcttg acatcccatt gaaaatcctt     960
taaccgtggt ccctcttcgg agcaatggag acaggtggtg catggttgtc gtcagctcgt    1020
gtcgtgagat gttgggttaa gtcccgcaac gagcgcaacc cttatcctta gtagccagca    1080
catgatggtg ggcactctgg ggagactgcc agggataacc tggaggaagg tgggatgac    1140 gtcaaatcat catgccccct tatgatttgg gctacacacgt gctacaatgg cgtaaacaaa    1200
gggaagcaaa ggagcgatct ggagcaaacc ccaaaaataa cgtctcagtt cggattgcag    1260
gctgcaactc gcctgcatga agctggaatc gctagtaatc gcgaatcaga atgtcgcggt    1320
gaatacgttc ccgggtcttg tacacaccgc ccgtcacacc atgggagttg gtaacgcccg    1380
aagtcagtga cccaaccgta aggaggagcg ccgaaggcga ggt                      1423
```

<210> SEQ ID NO 13
<211> LENGTH: 1423
<212> TYPE: DNA
<213> ORGANISM: Bifidobacterium breve

<400> SEQUENCE: 13

```
cggggctgct taaatgcagt cgaacgggat ccatcaagct tgcttggtgg tgagagtggc      60
gaacgggtga gtaatgcgtg accgacctgc cccatgcacc ggaatagctc ctggaaacgg     120
gtggtaatgc cggatgctcc atcacactgc atggtgtgtt gggaaagcct tgcggcatg     180 ggatggggtc gcgtcctatc agcttgatgg cggggtaacg gcccaccatg gcttcgacgg     240
gtagccggcc tgagagggcg accggccaca ttgggactga gatacggccc agactcctac     300
gggaggcagc agtgggggaat attgcacaat gggcgcaagc ctgatgcagc gacgccgcgt     360
gagggatgga ggccttcggg ttgtaaacct ctttttgttag ggagcaaggc attttgtgtt     420
gagtgtacct ttcgaataag caccggctaa ctacgtgcca gcagccgcgg taatacgtag     480
ggtgcaagcg ttatccggaa ttattgggcg taaagggctc gtaggcggtt cgtcgcgtcc     540
ggtgtgaaag tccatcgctt aacggtggat ccgcgccggg tacgggcggg cttgagtgcg     600
gtagggagga ctggaattcc cggtgtaacg gtggaatgtg tagatatcgg gaagaacacc     660
aatggcgaag gcaggtctct gggccgttac tgacgctgag gagcgaaagc gtgggagcg     720 aacaggatta gataccctgg tagtccacgc cgtaaacggt ggatgctgga gtgtgggccc     780
gttccacggg ttccgtgtcg gagctaacgc gttaagcatc ccgcctgggg agtacggccg     840
caaggctaaa actcaaagaa attgacgggg gcccgcacaa gcggcggagc atgcggatta     900
```

```
attcgatgca acgcgaagaa ccttacctgg gcttgacatg ttcccgacga tcccagagat      960
ggggtttccc ttcggggcgg gttcacaggt ggtgcatggt cgtcgtcagc tcgtgtcgtg     1020
agatgttggg ttaagtcccg caacgagcgc aaccctcgcc ccgtgttgcc agcggattgt     1080
gccgggaact cacgggggac cgccggggtt aactcggagg aaggtgggga tgacgtcaga     1140
tcatcatgcc ccttacgtcc agggcttcac gcatgctaca atggccggta caacgggatg     1200
cgacagcgcg agctggagcg gatccctgaa aaccggtctc agttcggatc gcagtctgca     1260
actcgactgc gtgaaggcgg agtcgctagt aatcgcgaat cagcaacgtc gcggtgaatg     1320
cgttcccggg ccttgtacac accgcccgtc aagtcatgaa agtgggcagc acccgaagcc     1380
ggtggcctaa ccccttgcgg gagggagccg tctaaggtag gtt                      1423
```

<210> SEQ ID NO 14
<211> LENGTH: 1425
<212> TYPE: DNA
<213> ORGANISM: Ruminococcus sp. M-1

<400> SEQUENCE: 14

```
cgggcgctgc ttacctgcag tcgagcgaag cacttgagcg gatttcttcg gattgaagtt       60
tttttgactg agcggcggac gggtgagtaa cgcgtgggta acctgcctca tacaggggga      120
taacagttag aaatggctgc taataccgca taagcgcaca ggaccgcatg gtctggtgtg      180
aaaaactccg gtggtatgag atggacccgc gtctgattag ctagttggag gggtaacggc      240
ccaccaaggc gacgatcagt agccggcctg agagggtgaa cggccacatt gggactgaga      300
cacggcccag actcctacgg gaggcagcag tggggaatat tgcacaatgg gggaaaccct      360
gatgcagcga cgccgcgtga aggaagaagt atctcggtat gtaaacttct atcagcaggg      420
aagaaaatga cggtacctga ctaagaagcc ccggctaact acgtgccagc agccgcggta      480
atacgtaggg ggcaagcgtt atccggattt actgggtgta aagggagcgt agacggaaga      540
gcaagtctga tgtgaaaggc tggggcttaa ccccaggact gcattggaaa ctgttttttct     600
agagtgccgg agaggtaagc ggaattccta gtgtagcggt gaaatgcgta gatattagga      660
ggaacaccag tggcgaaggc ggcttactgg acggtaactg acgttgaggc tcgaaagcgt      720
ggggagcaaa caggattaga taccctggta gtccacgccg taaacgatga atactaggtg      780
tcgggtggca aagccattcg gtgccgcagc aaacgcaata agtattccac ctggggagta      840
cgttcgcaag aatgaaactc aaaggaattg acggggaccc gcacaagcgg tggagcatgt      900
ggtttaattc gaagcaacgc gaagaacctt accaagtctt gacatccctc tgaccggccc      960
gtaacgggc cttcccttcg ggcagagga cacaggtggt gcatggttgt cgtcagctcg      1020
tgtcgtgaga tgttgggtta agtcccgcaa cgagcgcaac ccctatcctt agtagccagc     1080
aggtgaagct gggcactcta gggagactgc cggggataac ccggaggaag cggggacga     1140
cgtcaaatca tcatgcccct tatgatttgg gctacacacg tgctacaatg gcgtaaacaa     1200
agggaagcga gacagcgatg ttgagcaaat cccaaaaata acgtcccagt tcggactgca     1260
gtctgcaact cgactgcacg aagctggaat cgctagtaat cgcgaatcag aatgtcgcgg     1320
tgaatacgtt cccgggtctt gtacacaccg cccgtcacac catgggagtc agtaacgccc     1380
gaagtcagtg acccaacctt ataggaggag cgccgaagtc gacct                    1425
```

<210> SEQ ID NO 15
<211> LENGTH: 1416
<212> TYPE: DNA

<213> ORGANISM: Coprobacillus cateniformis

<400> SEQUENCE: 15

| | | | | | |
|---|---|---|---|---|---|
| cgcgggtgct | atactgcagt | cgaacgcact | gattttatca | gtgagtggcg | aacgggtgag | 60 |
| taatacataa | gtaacctgcc | ctcatgaggg | ggataactat | tagaaatgat | agctaagacc | 120 |
| gcataggtga | aggggtcgca | tgaccgcttc | attaaatatc | cgtatggata | gcaggaggat | 180 |
| ggacttatgg | cgcattagct | ggttggtgag | gtaacggctc | accaaggcga | cgatgcgtag | 240 |
| ccgacctgag | agggtggacg | gccacactgg | gactgagaca | cggcccagac | tcctacggga | 300 |
| ggcagcagta | gggaattttc | ggcaatgggg | gaaaccctga | ccgagcaacg | ccgcgtgagg | 360 |
| gaagaagtat | ttcggtatgt | aaacctctgt | tataaaggaa | gaacggtatg | aataggaaat | 420 |
| gattcataag | tgacggtact | ttatgagaaa | gccacggcta | actacgtgcc | agcagccgcg | 480 |
| gtaatacgta | ggtggcgagc | gttatccgga | atcattgggc | gtaaagaggg | agcaggcggc | 540 |
| aatagaggtc | tgcggtgaaa | gcctgaagct | aaacttcagt | aagccgtgga | aaccaaatag | 600 |
| ctagagtgca | gtagaggatc | gtggaattcc | atgtgtagcg | gtgaaatgcg | tagatatatg | 660 |
| gaggaacacc | agtggcgaag | gcgacgatct | gggctgcaac | tgacgctcag | tcccgaaagc | 720 |
| gtggggagca | aataggatta | gatacccctag | tagtccacgc | cgtaaacgat | gagtactaag | 780 |
| tgttggggt | caaacctcag | tgctgcagtt | aacgcaataa | gtactccgcc | tgagtagtac | 840 |
| gttcgcaaga | atgaaactca | aaggaattga | cgggggcccg | cacaagcggt | ggagcatgtg | 900 |
| gtttaattcg | aagcaacgcg | aagaacctta | ccaggtcttg | acatacctct | aaaggctcta | 960 |
| gagatagaga | gatagctata | ggggatacag | gtggtgcatg | gttgtcgtca | gctcgtgtcg | 1020 |
| tgagatgttg | ggttaagtcc | cgcaacgagc | gcaacccttg | tcgctagtta | ccatcattaa | 1080 |
| gttggggact | ctagcgagac | tgcctctgca | aggaggagga | aggcgggat | gacgtcaaat | 1140 |
| catcatgccc | cttatgacct | gggctacaca | cgtgctacaa | tggacggatc | aaagggaagc | 1200 |
| gaagccgcga | ggtggagcga | aacccaaaaa | cccgttctca | gttcggactg | cagtctgcaa | 1260 |
| ctcgactgca | cgaagttgga | atcgctagta | atcgcgaatc | agaatgtcgc | ggtgaatacg | 1320 |
| ttctcgggcc | ttgtacacac | cgcccgtcac | accatgagag | ttggtaacac | ccgaagccgg | 1380 |
| tggcttaacc | gcaaggagag | agcttctaag | gtgaat | | | 1416 |

<210> SEQ ID NO 16
<211> LENGTH: 1424
<212> TYPE: DNA
<213> ORGANISM: Clostridium symbiosum

<400> SEQUENCE: 16

| | | | | | |
|---|---|---|---|---|---|
| aggcgcgtgc | taccatgcag | tcgaacgaag | caatttaacg | gaagttttcg | gatggaagtt | 60 |
| gaattgactg | agtggcggac | gggtgagtaa | cgcgtgggta | acctgccttg | tactggggga | 120 |
| caacagttag | aaatgactgc | taataccgca | taagcgcaca | gtatcgcatg | atacagtgtg | 180 |
| aaaaactccg | gtggtacaag | atggacccgc | gtctgattag | ctagttggta | aggtaacggc | 240 |
| ttaccaaggc | gacgatcagt | agccgacctg | agagggtgac | cggccacatt | gggactgaga | 300 |
| cacggcccaa | actcctacgg | gaggcagcag | tggggaatat | tgcacaatgg | gcgaaagcct | 360 |
| gatgcagcga | cgccgcgtga | gtgaagaagt | atttcggtat | gtaaagctct | atcagcaggg | 420 |
| aagaaaatga | cggtacctga | ctaagaagcc | ccggctaact | acgtgccagc | agccgcggta | 480 |
| atacgtaggg | ggcaagcgtt | atccggattt | actgggtgta | aagggagcgt | agacggtaaa | 540 |
| gcaagtctga | agtgaaagcc | cgcggctcaa | ctgcgggact | gctttggaaa | ctgtttaact | 600 |

```
ggagtgtcgg agaggtaagt ggaattccta gtgtagcggt gaaatgcgta gatattagga      660
ggaacaccag tggcgaaggc gacttactgg acgataactg acgttgaggc tcgaaagcgt      720
ggggagcaaa caggattaga taccctggta gtccacgccg taaacgatga atactaggtg      780
ttggggagca aagctcttcg gtgccgtcgc aaacgcagta agtattccac ctggggagta      840
cgttcgcaag aatgaaactc aaaggaattg acggggaccc gcacaagcgg tggagcatgt      900
ggtttaattc gaagcaacgc gaagaacctt accaggtctt gacatcgatc gacggggga      960 gtaacgtccc cttcccttcg ggcggagaa acaggtggt gcatggttgt cgtcagctcg      1020
tgtcgtgaga tgttgggtta agtcccgcaa cgagcgcaac ccttattcta gtagccagc      1080 ggttcggccg ggaactcttg ggagactgcc aggataacc tggaggaagg tggggatgac      1140
gtcaaatcat catgcccctt atgatctggg ctacacacgt gctacaatgg cgtaaacaaa     1200
gagaagcaag accgcgaggt ggagcaaatc tcaaaaataa cgtctcagtt cggactgcag     1260
gctgcaactc gcctgcacga agctggaatc gctagtaatc gcgaatcaga atgtcgcggt     1320
gaatacgttc ccgggtcttg tacacaccgc ccgtcacacc atgggagtca gtaacgcccg     1380
aagtcagtga cccaaccgca aggaggagcg ccgaaggcga ccgt                      1424

<210> SEQ ID NO 17
<211> LENGTH: 1426
<212> TYPE: DNA
<213> ORGANISM: Bacteroides dorei

<400> SEQUENCE: 17
cggtctcggc ttaccatgca gtcgaggggc agcatggtct tagcttgcta aggctgatgg       60
cgaccggcgc acgggtgagt aacacgtatc caacctgccg tctactcttg gccagccttc      120
tgaaaggaag attaatccag gatggcatca tgagttcaca tgtccgcatg attaaaggta      180
ttttccggta gacgatgggg atgcgttcca ttagatagta ggcggggtaa cggcccacct      240
agtcaacgat ggataggggt tctgagagga aggtccccca cattggaact gagacacggt      300
ccaaactcct acgggaggca gcagtgagga atattggtca atgggcgatg cctgaacca      360 gccaagtagc gtgaaggatg actgccctat gggttgtaaa cttctttat aaaggaataa     420 agtcgggtat gcatacccgt ttgcatgtac tttatgaata aggatcggct aactccgtgc      480
cagcagccgc ggtaatacgg aggatccgag cgttatccgg atttattggg tttaagggga      540
gcgtagatgg atgtttaagt cagttgtgaa agtttgcggc tcaaccgtaa aattgcagtt      600
gatactggat gtcttgagtg cagttgaggc aggcggaatt cgtggtgtag cggtgaaatg      660
cttagatatc acgaagaact ccgattgcga aggcagcctg ctaagctgca actgacattg      720
aggctcgaaa gtgtgggtat caacaggat tagataccct ggtagtccac acggtaaacg      780
atgaatactc gctgtttgcg atatacggca agcggccaag cgaaagcgtt aagtattcca      840
cctggggagt acgccggcaa cggtgaaact caaaggaatt gacgggggcc cgcacaagcg      900
gaggaacatg tggtttaatt cgatgatacg cgaggaacct taccggggct taaattgcac      960
tcgaatgatc cggaaacggt tcagctagca atagcgagtg tgaaggtgct gcatggttgt    1020
cgtcagctcg tgccgtgagg tgtcggctta agtgccataa cgagcgcaac ccttgttgtc    1080
agttactaac aggtgatgct gaggactctg acaagactgc catcgtaaga tgtgaggaag    1140
gtggggatga cgtcaaatca gcacggccct tacgtccggg ctacacacg tgttacaatg    1200 gggggtacag agggccgcta ccacgcgagt ggatgccaat ccctaaaacc cctctcagtt    1260
```

```
cggactggag tctgcaaccc gactccacga agctggattc gctagtaatc gcgcatcagc   1320
cacggcgcgg tgaatacgtt cccgggcctt gtacacaccg cccgtcaagc catgggagcc   1380
gggggtacct gaagtgcgta accgcgagga tcgccctagg taatga                 1426

<210> SEQ ID NO 18
<211> LENGTH: 1428
<212> TYPE: DNA
<213> ORGANISM: Anaerostipes caccae

<400> SEQUENCE: 18
cggcggctgc ttaccatgca gtcgaacgaa gcatttagga ttgaagtttt cggatggatt     60
tcctatatga ctgagtggcg gacgggtgag taacgcgtgg ggaacctgcc ctatacaggg    120
ggataacagc tggaaacggc tgctaatacc gcataagcgc acagaatcgc atgattcagt    180
gtgaaaagcc ctggcagtat aggatggtcc cgcgtctgat tagctggttg gtgaggtaac    240
ggctcaccaa ggcgacgatc agtagccggc ttgagagagt gaacggccac attgggactg    300
agacacggcc caaactccta cgggaggcag cagtgggaa tattgcacaa tgggggaaac    360
cctgatgcag cgacgccgcg tgagtgaaga agtatttcgg tatgtaaagc tctatcagca    420
gggaagaaaa cagacggtac ctgactaaga agccccggct aactacgtgc cagcagccgc    480
ggtaatacgt aggggcaag cgttatccgg aattactggg tgtaaagggt gcgtaggtgg    540
catggtaagt cagaagtgaa agcccggggc ttaaccccgg gactgctttt gaaactgtca    600
tgctggagtg caggagaggt aagcggaatt cctagtgtag cggtgaaatg cgtagatatt    660
aggaggaaca ccagtggcga aggcggctta ctggactgtc actgacactg atgcacgaaa    720
gcgtggggag caaacaggat tagataccct ggtagtccac gccgtaaacg atgaatacta    780
ggtgtcgggg ccgtagagc ttcggtgccg cagcaaacgc agtaagtatt ccacctgggg    840
agtacgttcg caagaatgaa actcaaagga attgacgggg acccgcacaa gcggtggagc    900
atgtggttta attcgaagca acgcgaagaa ccttacctgg tcttgacatc ccaatgaccg    960
aaccttaacc ggttttttct ttcgagacat ggagacagg tggtgcatgg ttgtcgtcag   1020
ctcgtgtcgt gagatgttgg gttaagtccc gcaacgagcg caaccccat ctttagtagc   1080 cagcatttaa ggtgggcact ctagagagac tgccaggat aacctggagg aaggtgggga   1140
cgacgtcaaa tcatcatgcc ccttatggcc agggctacac acgtgctaca atggcgtaaa   1200
caaagggaag cgaagtcgtg aggcgaagca atcccagaa ataacgtctc agttcggatt   1260
gtagtctgca actcgactac atgaagctgg aatcgctagt aatcgtgaat cagaatgtca   1320
cggtgaatac gttcccgggt cttgtacaca ccgcccgtca ccatggga gtcagtaacg   1380 cccgaagtca gtgacccaac cgcaaggagg gagctgccga agtacgag               1428

<210> SEQ ID NO 19
<211> LENGTH: 1082
<212> TYPE: DNA
<213> ORGANISM: Clostridium bolteae

<400> SEQUENCE: 19
tttgtggcga agcctgatgc agcgacgccg cgtgagtgaa gaagtatttc ggtatgtaaa     60
gctctatcag cagggaagaa aatgacggta cctgactaag aagccccggc taactacgtg    120
ccagcagccg cggtaatacg taggggcaa gcgttatccg gatttactgg gtgtaaaggg    180
agcgtagacg cgaagcaag tctgaagtga aacccagggg ctcaaccctg gactgctttt    240
ggaaactgtt ttgctagagt gtcggagagg taagtggaat tcctagtgta gcggtgaaat    300
```

-continued

```
gcgtagatat taggaggaac accagtggcg aaggcggctt actggacgat aactgacgtt    360
gaggctcgaa agcgtgggga gcaaacagga ttagataccc tggtagtcca cgccgtaaac    420
gatgaatgct aggtgttggg gggcaaagcc cttcggtgcc gtcgcaaacg cagtaagcat    480
tccacctggg gagtacgttc gcaagaatga aactcaaagg aattgacggg gacccgcaca    540
agcggtggag catgtggttt aattcgaagc aacgcgaaga accttaccaa gtcttgacat    600
cctcttgacc ggcgtgtaac ggcgccttcc cttcggggca agagagacag gtggtgcatg    660
gttgtcgtca gctcgtgtcg tgagatgttg ggttaagtcc cgcaacgagc gcaaccctta    720
tccttagtag ccagcaggta aagctgggca ctctagggag actgccaggg ataacctgga    780
ggaaggtggg gatgacgtca aatcatcatg ccccttatga tttgggctac acacgtgcta    840
caatggcgta aacaaaggga agcaagacag tgatgtggag caaatcccaa aaataacgtc    900
ccagttcgga ctgtagtctg caacccgact acacgaagct ggaatcgcta gtaatcgcga    960
atcagaatgt cgcggtgaat acgttcccgg gtcttgtaca caccgcccgt cacaccatgg   1020
gagtcagcaa cgcccgaagt cagtgaccca actcgcaaga gagggagcgc cgaagtcgtc   1080
at                                                                  1082
```

<210> SEQ ID NO 20
<211> LENGTH: 1426
<212> TYPE: DNA
<213> ORGANISM: Clostridium citroniae

<400> SEQUENCE: 20

```
ctggcgcggc taccatgcag tcgagcgaag cattacagcg gaagttttcg gatggaagct     60
ttaatgactg agcggcggac gggtgagtaa cgcgtggata acctgcctca tacaggggga    120
taacagttag aaatgactgc taataccgca taagcgcaca gtatcgcatg atacggtgtg    180
aaaaactccg gtggtatgag atggatccgc gtctgattag ttagttggcg gggtaaaggc    240
ccaccaagac gacgatcagt agccggcctg agagggtgaa cggccacatt gggactgaga    300
cacggcccaa actcctacgg gaggcagcag tggggaatat tgcacaatgg gggaaaccct    360
gatgcagcga cgccgcgtga gtgaagaagt atttcggtat gtaaagctct atcagcaggg    420
aagaaaatga cggtacctga ctaagaagcc ccggctaact acgtgccagc agccgcggta    480
atacgtaggg ggcaagcgtt atccggattt actgggtgta aagggagcgt agacggcaat    540
gcaagtctgg agtgaaaacc cagggctcaa ccctgggagt gctttggaaa ctgtatagct    600
agagtgctgg agaggtaagt ggaattccta gtgtagcggt gaaatgcgta gatattagga    660
ggaacaccag tggcgaaggc ggcttactgg acagtaactg acgttgaggc tcgaaagcgt    720
ggggagcaaa caggattaga taccctggta gtccacgccg taaacgatga atgctaggtg    780
ttgggggca aagcccttcg gtgccgtcgc aaacgcaata agcattccac ctggggagta    840
cgttcgcaag aatgaaactc aaaggaattg acggggaccc gcacaagcgg tggagcatgt    900
ggtttaattc gaagcaacgc gaagaacctt accaagtctt gacatcctcc tgaccggtcc    960
gtaacggggc ctttccttcg ggacaagaga gacaggtggt gcatggttgt cgtcagctcg   1020
tgtcgtgaga tgttgggtta agtcccgcaa cgagcgcaac ccttatcctt agtagccagc   1080
aggtagagct gggcactcta gggagactgc cagggataac ctggaggaag gtggggatga   1140
cgtcaaatca tcatgcccct tatgatttgg gctacacacg tgctacaatg gcgtaaacaa   1200
agggaggcga ccctgcgaag gcaagcaaat cccaaaaata acgtcccagt tcggactgta   1260
```

```
gtctgcaacc cgactacacg aagctggaat cgctagtaat cgcgaatcag aatgtcgcgg    1320
tgaatacgtt cccgggtctt gtacacaccg cccgtcacac catgggagtc agcaacgccc    1380
gaagtcagtg acccaactgc aggagaggga gcgccgaagt cgggct                   1426
```

```
<210> SEQ ID NO 21
<211> LENGTH: 30
<212> TYPE: DNA
<213> ORGANISM: Artificial Sequence
<220> FEATURE:
<223> OTHER INFORMATION: 454 adaptor sequence

<400> SEQUENCE: 21
ccatctcatc cctgcgtgtc tccgactcag                                       30

<210> SEQ ID NO 22
<211> LENGTH: 20
<212> TYPE: DNA
<213> ORGANISM: Artificial Sequence
<220> FEATURE:
<223> OTHER INFORMATION: partial sequence of modified primer 8F

<400> SEQUENCE: 22
agrgtttgat ymtggctcag                                                  20

<210> SEQ ID NO 23
<211> LENGTH: 30
<212> TYPE: DNA
<213> ORGANISM: Artificial Sequence
<220> FEATURE:
<223> OTHER INFORMATION: 454 adaptor sequence

<400> SEQUENCE: 23
cctatcccct gtgtgccttg gcagtctcag                                       30

<210> SEQ ID NO 24
<211> LENGTH: 19
<212> TYPE: DNA
<213> ORGANISM: Artificial Sequence
<220> FEATURE:
<223> OTHER INFORMATION: partial sequence of modified primer 338R

<400> SEQUENCE: 24
tgctgcctcc cgtaggagt                                                   19

<210> SEQ ID NO 25
<211> LENGTH: 20
<212> TYPE: DNA
<213> ORGANISM: Artificial Sequence
<220> FEATURE:
<223> OTHER INFORMATION: primer 8F

<400> SEQUENCE: 25
agagtttgat cmtggctcag                                                  20

<210> SEQ ID NO 26
<211> LENGTH: 19
<212> TYPE: DNA
<213> ORGANISM: Artificial Sequence
<220> FEATURE:
<223> OTHER INFORMATION: primer 1492R

<400> SEQUENCE: 26
ggytaccttg ttacgactt                                                   19
```